US011835519B2

(12) United States Patent
Miske et al.

(10) Patent No.: US 11,835,519 B2
(45) Date of Patent: Dec. 5, 2023

(54) AUTOANTIBODIES TO SEPTIN-7 AND DIAGNOSIS OF NEUROLOGICAL DISEASE

(71) Applicants: EUROIMMUN Medizinische Labordiagnostika AG, Luebeck (DE); Mayo Foundation for Medical Education and Research, Rochester, MN (US)

(72) Inventors: Ramona Miske, Luebeck (DE); Madeleine Scharf, Selmsdorf (DE); Lars Komorowski, Ratzeburg (DE); Yvonne Denno, Luebeck (DE); Stefanie Hahn, Reinfeld (DE); Christiane Radzimski, Reinfeld (DE); Mandy Unger, Hamburg (DE); Andrew McKeon, Rochester, MN (US); Sean Pittock, Rochester, MN (US); Thomas Kryzer, Mantorville, MN (US); Vanda Lennon, Rochester, MN (US); Josephe Honorat, Brooklyn, NY (US)

(73) Assignees: EUROIMMUN Medizinische Labordiagnostika AG, Luebeck (DE); Mayo Foundation for Medical Education and Research, Rochester, MN (US)

( * ) Notice: Subject to any disclaimer, the term of this patent is extended or adjusted under 35 U.S.C. 154(b) by 83 days.

(21) Appl. No.: 17/114,984

(22) Filed: Dec. 8, 2020

(65) Prior Publication Data
US 2021/0181196 A1    Jun. 17, 2021

(30) Foreign Application Priority Data
Dec. 17, 2019    (EP) .................................... 19217147

(51) Int. Cl.
*G01N 33/564*    (2006.01)
*A61K 38/17*    (2006.01)

(52) U.S. Cl.
CPC ....... *G01N 33/564* (2013.01); *A61K 38/1709* (2013.01); *G01N 2333/46* (2013.01); *G01N 2800/28* (2013.01)

(58) Field of Classification Search
CPC ............. G01N 33/564; G01N 2333/46; G01N 2333/47; G01N 2800/28
See application file for complete search history.

(56) References Cited

FOREIGN PATENT DOCUMENTS

| CN | 112147324 | 12/2020 |
|---|---|---|
| WO | 2013/138509 | 9/2013 |
| WO | 2016/125148 | 8/2016 |
| WO | 2019/226616 | 11/2019 |

OTHER PUBLICATIONS

Kobayashi M et al. Acquisition of useful sero-diagnostic autoantibodies using the same patients' sera and tumor tissues. Biomedical Research (Tokyo), 35(2), 133-143. (Year: 2014).*
Honorat JA et al. Autoimmune septin-5 cerebellar ataxia. Neurology: Neuroimmunology & Neuroinflammation, 5(5):1-6. (Year: 2018).*
Bahtz, et al., "Identification of septin complex as an autoantibody target in paraneoplastic cerebellar ataxia," Journal of Neuroimmunology, vol. 275, No. 1-2, Oct. 1, 2014, 2 pages.
Degroote, et al. "Unraveling the Equine Lymphocyte Proteome: Differential Septin 7 Expression Associates with Immune Cells in Equine Recurrent Uveitis", PLOS ONE, Mar. 2014, vol. 9, No. 3, 9 pages.
Honorat, et al. "Autoimmune septin-5 cerebellar ataxia," Neurology: Neuroimmunology & Neuroinflammation, vol. 5, No. 5, Sep. 2018, 6 pages.
Lefranc, et al., "Characterization of Discriminant Human Brain Antigenic Targets in Neuropsychiatric Systemic Lupus Erythematosus Using an Immunoproteomic Approach," Arthritis & Rheumatism, vol. 56, No. 10, Oct. 1, 2002, 13 pages.
Wang et al., "The role of septin 7 in physiology and pathological disease: A systematic review of current status," Journal of Cellular and Molecular Medicine, vol. 22, No. 7, Mar. 30, 2018, 10 pages.
Partial European Search Report dated Jul. 31, 2020, in European Application No. 19217147.8.
Extended European Search Report dated Nov. 2, 2020, in European Application No. 19217147.8.
The American Cancer Society, "What is Lung Cancer?—Types of Lung Cancer", Cancer.org, www.cancer.org/cancer/lung-cancer/about/what-is.html, last revised Jan. 12, 2023, 6 pages.
The American Cancer Society, "What are Lung Carcinoid Tumors?", Cancer.org, www.cancer.org/cancer/lung-carcinoid-tumor/about/what-is-lung-carcinoid-tumor.html, last revised Aug. 27, 2018, 5 pages.

* cited by examiner

*Primary Examiner* — Kimberly Ballard
(74) *Attorney, Agent, or Firm* — Grüneberg and Myers PLLC

(57) ABSTRACT

A method for diagnosing a disease can include detecting, in a sample from a patient, an autoantibody binding to Septin-7. A polypeptide comprising Septin-7 or a variant thereof can be used for the diagnosis of a disease. Preferably, the polypeptide is used to detect an autoantibody binding to Septin-7 in a sample. A kit is useful for the diagnosis of a disease. The kit may include a polypeptide that includes Septin-7 or a variant thereof or a medical device that includes a polypeptide that includes Septin-7 or a variant thereof and an autoantibody to Septin-7.

13 Claims, 9 Drawing Sheets

Specification includes a Sequence Listing.

| Pt/Age/Sex | IgGs | Clinical presentation | Syndrome | MRI | Neurophysiology | CSF | Treatment | Outcome |
|---|---|---|---|---|---|---|---|---|
| 1/60/F | Septin-5 | Vertigo, nausea, vomiting, | Ataxia | N | , | , | None | Resolved spontaneously |
| 2/59/F | Septin-5 | Spinocerebellar syndrome, tremor | Ataxia | N | , | , | Prednisone | No improvement, died |
| 3/62/M | Septin-5 | Eye movement disorder, tremor | Ataxia | , | , | , | , | , |
| 4/47/M | Septin-5 | Ataxia | Ataxia | Cerebellar vermis atrophy | , | Pro, 70 mg/dL; ↑ synth | IV methylprednisolone (improved) & IVIg (maintenance) | Cane, ambulated with residual ataxic signs |
| 5/40/M | Septin-5 & -7 | Ataxia, dysarthria, diplopia | Ataxia | Cerebellar FDG hyper-metabolism | , | WBCs, 144/μL, (lymphocyte predominant) | IV steroids with PO prednisone taper | Improved, then worsened on taper |
| 6/62/M | Septin-5 & -7 | Ataxia, oscillopsia (downbeat nystagmus plus periodic alternating nystagmus) dysarthria. | Ataxia | Normal brain | , | WBCs, 35/μL (93% lymph); pro, 47 mg/dL, OCBS, 14; ↑ synth. (23.8) | IVIg, no response; corticosteroids, response | No change |
| 7/73/F | Septin-7 | Encephalitis (HSV) followed by worsening, & subsequent transient global amnesia | Encephalitis | Left temporal changes c/w HSV-1 | , | , | Acyclovir | Recovery |
| 8/69/F | Septin-7 | Background cognitive decline, followed by subacute encephalopathy, hallucinations & aggression. History of RA. | Encephalopathy | Generalized cerebral atrophy | EEG, triphasic waves | Pro, 42mg/dL | , | Readmitted with worsening |

Fig. 5A

| Pt/Age/Sex | IgGs | Clinical presentation | Syndrome | MRI | Neurophysiology | CSF | Treatment | Outcome |
|---|---|---|---|---|---|---|---|---|
| 9/62/M | Septin-7 | Background 15 years psychiatric symptoms followed by agitation, psychosis, paranoia, agitated, then withdrawn, mute, anorexia, 40 lb weight loss | Encephalopathy | , | , | ' | ' | ' |
| 10/76/M | Septin-7 | Recurrent catatonia, bradykinesia with tremulousness. Right leg weakness & paresthesias, brisk reflexes. | Encephalo-myelopathy | Generalized cerebral atrophy | EEG, triphasic waves | Pro, 140 mg/dL | IV steroids | Rapid improvement |
| 11/58/F | Septin-7 | Left leg weakness, IVIg responsive, then relapse with right leg weakness & ptosis | Encephalo-myelopathy | Normal brain & whole spine | EMG: old L5 radiculopathy | Pro, 103 mg/dL | 1st episode: IVIg (recovered); 2nd episode: prednisone & mycophenolate mofetil (recovered) | Remission |
| 12/65/F | Septin-7 | Left facial droop, left grip weakness | Encephalopathy | - | ' | ' | NA | NA |
| 13/82/F | Septin-7 | Myelitis. Optic neuritis 10 years prior. (MOG, AQP4 Abs negative) | Myelopathy | ' | ' | Normal | ' | ' |
| 14/85/M | Septin-7 | Chronic neuropathy with foot-drop, presented with sudden worsening | Myelo-neuropathy | Normal thoracic & lumbar spine imaging | EMG: Lumbosacral polyradiculo-neuropathy | , | ' | ' |
| 15/72/F | Septin-7 | Developed encephalopathy, weakness, stopped eating, and lost 50 lbs over 1 year. Hx of thyroid disease, SLE. | Encephalopathy | ' | ' | , | ' | ' |

Fig. 5B

| Pt/Age/Sex | IgGs | Clinical presentation | Syndrome | MRI | Neurophysiology | CSF | Treatment | Outcome |
|---|---|---|---|---|---|---|---|---|
| 16/68/M | Septin-7 | Left upper & lower extremity weakness, progressed to L>R spastic quadriparesis, caudal to rostral gradient of severity | Myelopathy | Frontal atrophy, increased T2 signal over bilateral motor strips; Normal C-spine | EMG: axonal sensory neuropathy | - | - | - |
| 17/79/M | Septin-7 | Episodic ataxia | Episodic ataxia | - | - | - | - | - |
| 18/56/F | Septin-7 | Encephalopathy, apathy, poor insight | Encephalopathy | - | - | ↑WBCs (lymphocyte predominant) | - | - |
| 19/77/M | Septin-7 | Background cognitive decline, methamphetamine use, followed by subacute encephalopathy, agitation & aggression. | Encephalopathy | - | - | WBCs, 78/μL; pro 92 mg/dL | None | Spontaneously returned to baseline |

Fig. 5C

SEQUENCE LISTING

<160> NUMBER OF SEQ ID NOS: 23

<210> SEQ ID NO 1
<211> LENGTH: 437
<212> TYPE: PRT
<213> ORGANISM: Homo sapiens

<400> SEQUENCE: 1

```
Met Ser Val Ser Ala Arg Ser Ala Ala Glu Glu Arg Ser Val Asn
1               5                   10                  15

Ser Ser Thr Met Val Ala Gln Gln Lys Asn Leu Glu Gly Tyr Val Gly
            20                  25                  30

Phe Ala Asn Leu Pro Asn Gln Val Tyr Arg Lys Ser Val Lys Arg Gly
            35                  40                  45

Phe Glu Phe Thr Leu Met Val Val Gly Glu Ser Gly Leu Gly Lys Ser
        50                  55                  60

Thr Leu Ile Asn Ser Leu Phe Leu Thr Asp Leu Tyr Ser Pro Glu Tyr
65                  70                  75                  80

Pro Gly Pro Ser His Arg Ile Lys Lys Thr Val Gln Val Glu Gln Ser
                85                  90                  95

Lys Val Leu Ile Lys Glu Gly Gly Val Gln Leu Leu Leu Thr Ile Val
                100                 105                 110

Asp Thr Pro Gly Phe Gly Asp Ala Val Asp Asn Ser Asn Cys Trp Gln
            115                 120                 125

Pro Val Ile Asp Tyr Ile Asp Ser Lys Phe Glu Asp Tyr Leu Asn Ala
        130                 135                 140

Glu Ser Arg Val Asn Arg Arg Gln Met Pro Asp Asn Arg Val Gln Cys
145                 150                 155                 160

Cys Leu Tyr Phe Ile Ala Pro Ser Gly His Gly Leu Lys Pro Leu Asp
                165                 170                 175

Ile Glu Phe Met Lys Arg Leu His Glu Lys Val Asn Ile Ile Pro Leu
            180                 185                 190

Ile Ala Lys Ala Asp Thr Leu Thr Pro Glu Glu Cys Gln Gln Phe Lys
        195                 200                 205

Lys Gln Ile Met Lys Glu Ile Gln Glu His Lys Ile Lys Ile Tyr Glu
    210                 215                 220
```

```
Phe Pro Glu Thr Asp Asp Glu Glu Asn Lys Leu Val Lys Lys Ile
225                 230                 235                 240

Lys Asp Arg Leu Pro Leu Ala Val Val Gly Ser Asn Thr Ile Ile Glu
            245                 250                 255

Val Asn Gly Lys Arg Val Arg Gly Arg Gln Tyr Pro Trp Gly Val Ala
        260                 265                 270

Glu Val Glu Asn Gly Glu His Cys Asp Phe Thr Ile Leu Arg Asn Met
    275                 280                 285

Leu Ile Arg Thr His Met Gln Asp Leu Lys Asp Val Thr Asn Asn Val
290                 295                 300

His Tyr Glu Asn Tyr Arg Ser Arg Lys Leu Ala Ala Val Thr Tyr Asn
305                 310                 315                 320

Gly Val Asp Asn Asn Lys Asn Lys Gly Gln Leu Thr Lys Ser Pro Leu
                325                 330                 335

Ala Gln Met Glu Glu Arg Arg Glu His Val Ala Lys Met Lys Lys
            340                 345                 350

Met Glu Met Glu Met Glu Gln Val Phe Glu Met Lys Val Lys Glu Lys
            355                 360                 365

Val Gln Lys Leu Lys Asp Ser Glu Ala Glu Leu Gln Arg Arg His Glu
370                 375                 380

Gln Met Lys Lys Asn Leu Glu Ala Gln His Lys Glu Leu Glu Glu Lys
385                 390                 395                 400

Arg Arg Gln Phe Glu Asp Glu Lys Ala Asn Trp Glu Ala Gln Gln Arg
                405                 410                 415

Ile Leu Glu Gln Gln Asn Ser Ser Arg Thr Leu Glu Lys Asn Lys Lys
            420                 425                 430

Lys Gly Lys Ile Phe
            435

<210> SEQ ID NO 2
<211> LENGTH: 436
<212> TYPE: PRT
<213> ORGANISM: Mus musculus

<400> SEQUENCE: 2

Met Ser Val Ser Ala Arg Ser Ala Ala Glu Glu Arg Ser Val Asn
1               5                   10                  15

Cys Gly Thr Met Ala Gln Pro Lys Asn Leu Glu Gly Tyr Val Gly Phe
            20                  25                  30

Ala Asn Leu Pro Asn Gln Val Tyr Arg Lys Ser Val Lys Arg Gly Phe
        35                  40                  45

Glu Phe Thr Leu Met Val Val Gly Glu Ser Gly Leu Gly Lys Ser Thr
50                  55                  60

Leu Ile Asn Ser Leu Phe Leu Thr Asp Leu Tyr Ser Pro Glu Tyr Pro
65                  70                  75                  80

Gly Pro Ser His Arg Ile Lys Lys Thr Val Gln Val Glu Gln Ser Lys
                85                  90                  95

Val Leu Ile Lys Glu Gly Gly Val Gln Leu Leu Leu Thr Ile Val Asp
            100                 105                 110

Thr Pro Gly Phe Gly Asp Ala Val Asp Asn Ser Asn Cys Trp Gln Pro
        115                 120                 125

Val Ile Asp Tyr Ile Asp Ser Lys Phe Glu Asp Tyr Leu Asn Ala Glu
    130                 135                 140

Ser Arg Val Asn Arg Arg Gln Met Pro Asp Asn Arg Val Gln Cys Cys
145                 150                 155                 160
```

```
Leu Tyr Phe Ile Ala Pro Ser Gly His Gly Leu Lys Pro Leu Asp Ile
                165                 170                 175

Glu Phe Met Lys Arg Leu His Glu Lys Val Asn Ile Ile Pro Leu Ile
            180                 185                 190

Ala Lys Ala Asp Thr Leu Thr Pro Glu Glu Cys Gln Gln Phe Lys Lys
        195                 200                 205

Gln Ile Met Lys Glu Ile Gln Glu His Lys Ile Lys Ile Tyr Glu Phe
    210                 215                 220

Pro Glu Thr Asp Asp Glu Glu Asn Lys Leu Val Lys Ile Lys
225                 230                 235                 240

Asp Arg Leu Pro Leu Ala Val Val Gly Ser Asn Thr Ile Ile Glu Val
                245                 250                 255

Asn Gly Lys Arg Val Arg Gly Arg Gln Tyr Pro Trp Gly Val Ala Glu
            260                 265                 270

Val Glu Asn Gly Glu His Cys Asp Phe Thr Ile Leu Arg Asn Met Leu
        275                 280                 285

Ile Arg Thr His Met Gln Asp Leu Lys Asp Val Thr Asn Asn Val His
    290                 295                 300

Tyr Glu Asn Tyr Arg Ser Arg Lys Leu Ala Ala Val Thr Tyr Asn Gly
305                 310                 315                 320

Val Asp Asn Asn Lys Asn Lys Gly Gln Leu Thr Lys Ser Pro Leu Ala
                325                 330                 335

Gln Met Glu Glu Arg Arg Glu His Val Ala Lys Met Lys Lys Met
            340                 345                 350

Glu Met Glu Met Glu Gln Val Phe Glu Met Lys Val Lys Glu Lys Val
        355                 360                 365

Gln Lys Leu Lys Asp Ser Glu Ala Glu Leu Gln Arg Arg His Glu Gln
    370                 375                 380

Met Lys Lys Asn Leu Glu Ala Gln His Lys Glu Leu Glu Glu Lys Arg
385                 390                 395                 400

Arg Gln Phe Glu Glu Glu Lys Ala Asn Trp Glu Ala Gln Gln Arg Ile
                405                 410                 415

Leu Glu Gln Gln Asn Ser Ser Arg Thr Leu Glu Lys Asn Lys Lys Lys
            420                 425                 430

Gly Lys Ile Phe
        435

<210> SEQ ID NO 3
<211> LENGTH: 436
<212> TYPE: PRT
<213> ORGANISM: Rattus norvegicus

<400> SEQUENCE: 3

Met Ser Val Ser Ala Arg Ser Ala Ala Glu Glu Arg Ser Val Asn
1               5                   10                  15

Cys Ser Thr Met Ala Gln Pro Lys Asn Leu Glu Gly Tyr Val Gly Phe
            20                  25                  30

Ala Asn Leu Pro Asn Gln Val Tyr Arg Lys Ser Val Lys Arg Gly Phe
        35                  40                  45

Glu Phe Thr Leu Met Val Val Gly Glu Ser Gly Leu Gly Lys Ser Thr
    50                  55                  60

Leu Ile Asn Ser Leu Phe Leu Thr Asp Leu Tyr Ser Pro Glu Tyr Pro
65                  70                  75                  80

Gly Pro Ser His Arg Ile Lys Lys Thr Val Gln Val Glu Gln Ser Lys
```

```
            85                  90                  95
Val Leu Ile Lys Glu Gly Gly Val Gln Leu Leu Thr Ile Val Asp
            100                 105                 110

Thr Pro Gly Phe Gly Asp Ala Val Asp Asn Ser Asn Cys Trp Gln Pro
            115                 120                 125

Val Ile Asp Tyr Ile Asp Ser Lys Phe Glu Asp Tyr Leu Asn Ala Glu
            130                 135                 140

Ser Arg Val Asn Arg Arg Gln Met Pro Asp Asn Arg Val Gln Cys Cys
145                 150                 155                 160

Leu Tyr Phe Ile Ala Pro Ser Gly His Gly Leu Lys Pro Leu Asp Ile
                165                 170                 175

Glu Phe Met Lys Arg Leu His Glu Lys Val Asn Ile Ile Pro Leu Ile
                180                 185                 190

Ala Lys Ala Asp Thr Leu Thr Pro Glu Glu Cys Gln Gln Phe Lys Lys
                195                 200                 205

Gln Ile Met Lys Glu Ile Gln Gly His Lys Ile Lys Ile Tyr Glu Phe
            210                 215                 220

Pro Glu Thr Asp Asp Glu Glu Asn Lys Leu Val Lys Lys Ile Lys
225                 230                 235                 240

Asp Arg Leu Pro Leu Ala Val Val Gly Ser Asn Thr Ile Ile Glu Val
                245                 250                 255

Asn Gly Lys Arg Val Arg Gly Arg Gln Tyr Pro Trp Gly Val Ala Glu
                260                 265                 270

Val Glu Asn Gly Glu His Cys Asp Phe Thr Ile Leu Arg Asn Met Leu
            275                 280                 285

Ile Arg Thr His Met Gln Asp Leu Lys Asp Val Thr Asn Asn Val His
            290                 295                 300

Tyr Glu Asn Tyr Arg Ser Arg Lys Leu Ala Ala Val Thr Tyr Asn Gly
305                 310                 315                 320

Val Asp Asn Asn Lys Asn Lys Gly Gln Leu Thr Lys Ser Pro Leu Ala
                325                 330                 335

Gln Met Glu Glu Arg Arg Glu His Val Ala Lys Met Lys Lys Met
                340                 345                 350

Glu Met Glu Met Glu Gln Val Phe Glu Met Lys Val Lys Glu Lys Val
            355                 360                 365

Gln Lys Leu Lys Asp Ser Glu Ala Glu Leu Gln Arg Arg His Glu Gln
            370                 375                 380

Met Lys Lys Asn Leu Glu Ala Gln His Lys Glu Leu Glu Glu Lys Arg
385                 390                 395                 400

Arg Gln Phe Glu Glu Glu Lys Ala Asn Trp Glu Ala Gln Gln Arg Ile
                405                 410                 415

Leu Glu Gln Gln Asn Ser Ser Arg Thr Leu Glu Lys Asn Lys Lys Lys
                420                 425                 430

Gly Lys Ile Phe
            435

<210> SEQ ID NO 4
<211> LENGTH: 358
<212> TYPE: PRT
<213> ORGANISM: Homo sapiens

<400> SEQUENCE: 4

Met Ser Lys Gly Leu Pro Glu Thr Arg Thr Asp Ala Ala Met Ser Glu
1               5                   10                  15
```

```
Leu Val Pro Glu Pro Arg Pro Lys Pro Ala Val Pro Met Lys Pro Met
                 20                  25                  30

Ser Ile Asn Ser Asn Leu Leu Gly Tyr Ile Gly Ile Asp Thr Ile Ile
             35                  40                  45

Glu Gln Met Arg Lys Lys Thr Met Lys Thr Gly Phe Asp Phe Asn Ile
         50                  55                  60

Met Val Val Gly Gln Ser Gly Leu Gly Lys Ser Thr Leu Val Asn Thr
65                  70                  75                  80

Leu Phe Lys Ser Gln Val Ser Arg Lys Ala Ser Ser Trp Asn Arg Glu
                 85                  90                  95

Glu Lys Ile Pro Lys Thr Val Glu Ile Lys Ala Ile Gly His Val Ile
            100                 105                 110

Glu Glu Gly Gly Val Lys Met Lys Leu Thr Val Ile Asp Thr Pro Gly
        115                 120                 125

Phe Gly Asp Gln Ile Asn Asn Glu Asn Cys Trp Glu Pro Ile Glu Lys
    130                 135                 140

Tyr Ile Asn Glu Gln Tyr Glu Lys Phe Leu Lys Glu Glu Val Asn Ile
145                 150                 155                 160

Ala Arg Lys Lys Arg Ile Pro Asp Thr Arg Val His Cys Cys Leu Tyr
                165                 170                 175

Phe Ile Ser Pro Thr Gly His Ser Leu Arg Pro Leu Asp Leu Glu Phe
            180                 185                 190

Met Lys His Leu Ser Lys Val Val Asn Ile Ile Pro Val Ile Ala Lys
        195                 200                 205

Ala Asp Thr Met Thr Leu Glu Glu Lys Ser Glu Phe Lys Gln Arg Val
    210                 215                 220

Arg Lys Glu Leu Glu Val Asn Gly Ile Glu Phe Tyr Pro Gln Lys Glu
225                 230                 235                 240

Phe Asp Glu Asp Leu Glu Asp Lys Thr Glu Asn Asp Lys Ile Arg Gln
                245                 250                 255

Glu Ser Met Pro Phe Ala Val Val Gly Ser Asp Lys Glu Tyr Gln Val
            260                 265                 270

Asn Gly Lys Arg Val Leu Gly Arg Lys Thr Pro Trp Gly Ile Ile Glu
        275                 280                 285

Val Glu Asn Leu Asn His Cys Glu Phe Ala Leu Leu Arg Asp Phe Val
    290                 295                 300

Ile Arg Thr His Leu Gln Asp Leu Lys Glu Val Thr His Asn Ile His
305                 310                 315                 320

Tyr Glu Thr Tyr Arg Ala Lys Arg Leu Asn Asp Asn Gly Gly Leu Pro
                325                 330                 335

Pro Gly Glu Gly Leu Leu Gly Thr Val Leu Pro Pro Val Pro Ala Thr
            340                 345                 350

Pro Cys Pro Thr Ala Glu
        355

<210> SEQ ID NO 5
<211> LENGTH: 369
<212> TYPE: PRT
<213> ORGANISM: Homo sapiens

<400> SEQUENCE: 5

Met Ser Thr Gly Leu Arg Tyr Lys Ser Lys Leu Ala Thr Pro Glu Asp
1               5                   10                  15

Lys Gln Asp Ile Asp Lys Gln Tyr Val Gly Phe Ala Thr Leu Pro Asn
             20                  25                  30
```

```
Gln Val His Arg Lys Ser Val Lys Gly Phe Asp Phe Thr Leu Met
             35                  40                  45

Val Ala Gly Glu Ser Gly Leu Gly Lys Ser Thr Leu Val His Ser Leu
 50                  55                  60

Phe Leu Thr Asp Leu Tyr Lys Asp Arg Lys Leu Leu Ser Ala Glu Glu
 65                  70                  75                  80

Arg Ile Ser Gln Thr Val Glu Ile Leu Lys His Thr Val Asp Ile Glu
                 85                  90                  95

Glu Lys Gly Val Lys Leu Lys Leu Thr Ile Val Asp Thr Pro Gly Phe
                100                 105                 110

Gly Asp Ala Val Asn Asn Thr Glu Cys Trp Lys Pro Ile Thr Asp Tyr
            115                 120                 125

Val Asp Gln Gln Phe Glu Gln Tyr Phe Arg Asp Glu Ser Gly Leu Asn
130                 135                 140

Arg Lys Asn Ile Gln Asp Asn Arg Val His Cys Cys Leu Tyr Phe Ile
145                 150                 155                 160

Ser Pro Phe Gly His Gly Leu Arg Pro Val Asp Val Gly Phe Met Lys
                165                 170                 175

Ala Leu His Glu Lys Val Asn Ile Val Pro Leu Ile Ala Lys Ala Asp
            180                 185                 190

Cys Leu Val Pro Ser Glu Ile Arg Lys Leu Lys Glu Arg Ile Arg Glu
            195                 200                 205

Glu Ile Asp Lys Phe Gly Ile His Val Tyr Gln Phe Pro Glu Cys Asp
210                 215                 220

Ser Asp Glu Asp Glu Asp Phe Lys Gln Gln Asp Arg Glu Leu Lys Glu
225                 230                 235                 240

Ser Ala Pro Phe Ala Val Ile Gly Ser Asn Thr Val Val Glu Ala Lys
                245                 250                 255

Gly Gln Arg Val Arg Gly Arg Leu Tyr Pro Trp Gly Ile Val Glu Val
            260                 265                 270

Glu Asn Gln Ala His Cys Asp Phe Val Lys Leu Arg Asn Met Leu Ile
            275                 280                 285

Arg Thr His Met His Asp Leu Lys Asp Val Thr Cys Asp Val His Tyr
290                 295                 300

Glu Asn Tyr Arg Ala His Cys Ile Gln Gln Met Thr Ser Lys Leu Thr
305                 310                 315                 320

Gln Asp Ser Arg Met Glu Ser Pro Ile Pro Ile Leu Pro Leu Pro Thr
                325                 330                 335

Pro Asp Ala Glu Thr Glu Lys Leu Ile Arg Met Lys Asp Glu Glu Leu
            340                 345                 350

Arg Arg Met Gln Glu Met Leu Gln Arg Met Lys Gln Gln Met Gln Asp
            355                 360                 365

Gln

<210> SEQ ID NO 6
<211> LENGTH: 434
<212> TYPE: PRT
<213> ORGANISM: Homo sapiens

<400> SEQUENCE: 6

Met Ala Ala Thr Asp Ile Ala Arg Gln Val Gly Glu Gly Cys Arg Thr
 1               5                  10                  15

Val Pro Leu Ala Gly His Val Gly Phe Asp Ser Leu Pro Asp Gln Leu
                20                  25                  30
```

-continued

```
Val Asn Lys Ser Val Ser Gln Gly Phe Cys Phe Asn Ile Leu Cys Val
            35                  40                  45
Gly Glu Thr Gly Leu Gly Lys Ser Thr Leu Met Asp Thr Leu Phe Asn
 50                  55                  60
Thr Lys Phe Glu Gly Glu Pro Ala Thr His Thr Gln Pro Gly Val Gln
 65                  70                  75                  80
Leu Gln Ser Asn Thr Tyr Asp Leu Gln Glu Ser Asn Val Arg Leu Lys
                85                  90                  95
Leu Thr Ile Val Ser Thr Val Gly Phe Gly Asp Gln Ile Asn Lys Glu
                100                 105                 110
Asp Ser Tyr Lys Pro Ile Val Glu Phe Ile Asp Ala Gln Phe Glu Ala
                115                 120                 125
Tyr Leu Gln Glu Glu Leu Lys Ile Arg Arg Val Leu His Thr Tyr His
                130                 135                 140
Asp Ser Arg Ile His Val Cys Leu Tyr Phe Ile Ala Pro Thr Gly His
145                 150                 155                 160
Ser Leu Lys Ser Leu Asp Leu Val Thr Met Lys Lys Leu Asp Ser Lys
                165                 170                 175
Val Asn Ile Ile Pro Ile Ile Ala Lys Ala Asp Ala Ile Ser Lys Ser
                180                 185                 190
Glu Leu Thr Lys Phe Lys Ile Lys Ile Thr Ser Glu Leu Val Ser Asn
                195                 200                 205
Gly Val Gln Ile Tyr Gln Phe Pro Thr Asp Asp Glu Ser Val Ala Glu
                210                 215                 220
Ile Asn Gly Thr Met Asn Ala His Leu Pro Phe Ala Val Ile Gly Ser
225                 230                 235                 240
Thr Glu Glu Leu Lys Ile Gly Asn Lys Met Met Arg Ala Arg Gln Tyr
                245                 250                 255
Pro Trp Gly Thr Val Gln Val Glu Asn Glu Ala His Cys Asp Phe Val
                260                 265                 270
Lys Leu Arg Glu Met Leu Ile Arg Val Asn Met Glu Asp Leu Arg Glu
                275                 280                 285
Gln Thr His Thr Arg His Tyr Glu Leu Tyr Arg Arg Cys Lys Leu Glu
                290                 295                 300
Glu Met Gly Phe Lys Asp Thr Asp Pro Asp Ser Lys Pro Phe Ser Leu
305                 310                 315                 320
Gln Glu Thr Tyr Glu Ala Lys Arg Asn Glu Phe Leu Gly Glu Leu Gln
                325                 330                 335
Lys Lys Glu Glu Met Arg Gln Met Phe Val Gln Arg Val Lys Glu
                340                 345                 350
Lys Glu Ala Glu Leu Lys Glu Ala Glu Lys Glu Leu His Glu Lys Phe
                355                 360                 365
Asp Arg Leu Lys Lys Leu His Gln Asp Glu Lys Lys Leu Glu Asp
                370                 375                 380
Lys Lys Lys Ser Leu Asp Asp Glu Val Asn Ala Phe Lys Gln Arg Lys
385                 390                 395                 400
Thr Ala Ala Glu Leu Leu Gln Ser Gln Gly Ser Gln Ala Gly Gly Ser
                405                 410                 415
Gln Thr Leu Lys Arg Asp Lys Glu Lys Lys Asn Asn Pro Trp Leu Cys
                420                 425                 430
Thr Glu
```

```
<210> SEQ ID NO 7
<211> LENGTH: 429
<212> TYPE: PRT
<213> ORGANISM: Homo sapiens

<400> SEQUENCE: 7
```

| Met | Ala | Val | Ala | Val | Gly | Arg | Pro | Ser | Asn | Glu | Glu | Leu | Arg | Asn | Leu |
|---|---|---|---|---|---|---|---|---|---|---|---|---|---|---|---|
| 1 | | | | 5 | | | | | 10 | | | | | 15 | |

| Ser | Leu | Ser | Gly | His | Val | Gly | Phe | Asp | Ser | Leu | Pro | Asp | Gln | Leu | Val |
|---|---|---|---|---|---|---|---|---|---|---|---|---|---|---|---|
| | | | 20 | | | | | 25 | | | | | 30 | | |

| Asn | Lys | Ser | Thr | Ser | Gln | Gly | Phe | Cys | Phe | Asn | Ile | Leu | Cys | Val | Gly |
|---|---|---|---|---|---|---|---|---|---|---|---|---|---|---|---|
| | | | 35 | | | | | 40 | | | | | 45 | | |

| Glu | Thr | Gly | Ile | Gly | Lys | Ser | Thr | Leu | Met | Asp | Thr | Leu | Phe | Asn | Thr |
|---|---|---|---|---|---|---|---|---|---|---|---|---|---|---|---|
| | 50 | | | | | 55 | | | | | 60 | | | | |

| Lys | Phe | Glu | Ser | Asp | Pro | Ala | Thr | His | Asn | Glu | Pro | Gly | Val | Arg | Leu |
|---|---|---|---|---|---|---|---|---|---|---|---|---|---|---|---|
| 65 | | | | | 70 | | | | | 75 | | | | | 80 |

| Lys | Ala | Arg | Ser | Tyr | Glu | Leu | Gln | Glu | Ser | Asn | Val | Arg | Leu | Lys | Leu |
|---|---|---|---|---|---|---|---|---|---|---|---|---|---|---|---|
| | | | | 85 | | | | | 90 | | | | | 95 | |

| Thr | Ile | Val | Asp | Thr | Val | Gly | Phe | Gly | Asp | Gln | Ile | Asn | Lys | Asp | Asp |
|---|---|---|---|---|---|---|---|---|---|---|---|---|---|---|---|
| | | | 100 | | | | | 105 | | | | | 110 | | |

| Ser | Tyr | Lys | Pro | Ile | Val | Glu | Tyr | Ile | Asp | Ala | Gln | Phe | Glu | Ala | Tyr |
|---|---|---|---|---|---|---|---|---|---|---|---|---|---|---|---|
| | | | 115 | | | | | 120 | | | | | 125 | | |

| Leu | Gln | Glu | Glu | Leu | Lys | Ile | Lys | Arg | Ser | Leu | Phe | Asn | Tyr | His | Asp |
|---|---|---|---|---|---|---|---|---|---|---|---|---|---|---|---|
| | 130 | | | | | 135 | | | | | 140 | | | | |

| Thr | Arg | Ile | His | Ala | Cys | Leu | Tyr | Phe | Ile | Ala | Pro | Thr | Gly | His | Ser |
|---|---|---|---|---|---|---|---|---|---|---|---|---|---|---|---|
| 145 | | | | | 150 | | | | | 155 | | | | | 160 |

| Leu | Lys | Ser | Leu | Asp | Leu | Val | Thr | Met | Lys | Lys | Leu | Asp | Ser | Lys | Val |
|---|---|---|---|---|---|---|---|---|---|---|---|---|---|---|---|
| | | | | 165 | | | | | 170 | | | | | 175 | |

| Asn | Ile | Ile | Pro | Ile | Ile | Ala | Lys | Ala | Asp | Thr | Ile | Ala | Lys | Asn | Glu |
|---|---|---|---|---|---|---|---|---|---|---|---|---|---|---|---|
| | | | 180 | | | | | 185 | | | | | 190 | | |

| Leu | His | Lys | Phe | Lys | Ser | Lys | Ile | Met | Ser | Glu | Leu | Val | Ser | Asn | Gly |
|---|---|---|---|---|---|---|---|---|---|---|---|---|---|---|---|
| | | | 195 | | | | | 200 | | | | | 205 | | |

| Val | Gln | Ile | Tyr | Gln | Phe | Pro | Thr | Asp | Glu | Glu | Thr | Val | Ala | Glu | Ile |
|---|---|---|---|---|---|---|---|---|---|---|---|---|---|---|---|
| | 210 | | | | | 215 | | | | | 220 | | | | |

| Asn | Ala | Thr | Met | Ser | Val | His | Leu | Pro | Phe | Ala | Val | Val | Gly | Ser | Thr |
|---|---|---|---|---|---|---|---|---|---|---|---|---|---|---|---|
| 225 | | | | | 230 | | | | | 235 | | | | | 240 |

| Glu | Glu | Val | Lys | Ile | Gly | Asn | Lys | Met | Ala | Lys | Ala | Arg | Gln | Tyr | Pro |
|---|---|---|---|---|---|---|---|---|---|---|---|---|---|---|---|
| | | | | 245 | | | | | 250 | | | | | 255 | |

| Trp | Gly | Val | Val | Gln | Val | Glu | Asn | Glu | Asn | His | Cys | Asp | Phe | Val | Lys |
|---|---|---|---|---|---|---|---|---|---|---|---|---|---|---|---|
| | | | 260 | | | | | 265 | | | | | 270 | | |

| Leu | Arg | Glu | Met | Leu | Ile | Arg | Val | Asn | Met | Glu | Asp | Leu | Arg | Glu | Gln |
|---|---|---|---|---|---|---|---|---|---|---|---|---|---|---|---|
| | | | 275 | | | | | 280 | | | | | 285 | | |

| Thr | His | Thr | Arg | His | Tyr | Glu | Leu | Tyr | Arg | Arg | Cys | Lys | Leu | Glu | Glu |
|---|---|---|---|---|---|---|---|---|---|---|---|---|---|---|---|
| | 290 | | | | | 295 | | | | | 300 | | | | |

| Met | Gly | Phe | Lys | Asp | Thr | Asp | Pro | Asp | Ser | Lys | Pro | Phe | Ser | Leu | Gln |
|---|---|---|---|---|---|---|---|---|---|---|---|---|---|---|---|
| 305 | | | | | 310 | | | | | 315 | | | | | 320 |

| Glu | Thr | Tyr | Glu | Ala | Lys | Arg | Asn | Glu | Phe | Leu | Gly | Glu | Leu | Gln | Lys |
|---|---|---|---|---|---|---|---|---|---|---|---|---|---|---|---|
| | | | | 325 | | | | | 330 | | | | | 335 | |

| Lys | Glu | Glu | Glu | Met | Arg | Gln | Met | Phe | Val | Met | Arg | Val | Lys | Glu | Lys |
|---|---|---|---|---|---|---|---|---|---|---|---|---|---|---|---|
| | | | 340 | | | | | 345 | | | | | 350 | | |

| Glu | Ala | Glu | Leu | Lys | Glu | Ala | Glu | Lys | Glu | Leu | His | Glu | Lys | Phe | Asp |
|---|---|---|---|---|---|---|---|---|---|---|---|---|---|---|---|
| | | | 355 | | | | | 360 | | | | | 365 | | |

| Leu | Leu | Lys | Arg | Thr | His | Gln | Glu | Glu | Lys | Lys | Val | Glu | Asp | Lys |
|---|---|---|---|---|---|---|---|---|---|---|---|---|---|---|
| | 370 | | | | | 375 | | | | | 380 | | | |

```
Lys Lys Glu Leu Glu Glu Val Asn Asn Phe Gln Lys Lys Lys Ala
385                 390                 395                 400

Ala Ala Gln Leu Leu Gln Ser Gln Ala Gln Gln Ser Gly Ala Gln Gln
            405                 410                 415

Thr Lys Lys Asp Lys Asp Lys Lys Asn Ala Ser Phe Thr
        420                 425

<210> SEQ ID NO 8
<211> LENGTH: 447
<212> TYPE: PRT
<213> ORGANISM: Artificial Sequence
<220> FEATURE:
<223> OTHER INFORMATION: human Septin-7, His tagged

<400> SEQUENCE: 8

Met Ser Val Ser Ala Arg Ser Ala Ala Glu Glu Arg Ser Val Asn
1               5                   10                  15

Ser Ser Thr Met Val Ala Gln Gln Lys Asn Leu Glu Gly Tyr Val Gly
            20                  25                  30

Phe Ala Asn Leu Pro Asn Gln Val Tyr Arg Lys Ser Val Lys Arg Gly
            35                  40                  45

Phe Glu Phe Thr Leu Met Val Val Gly Glu Ser Gly Leu Gly Lys Ser
50                  55                  60

Thr Leu Ile Asn Ser Leu Phe Leu Thr Asp Leu Tyr Ser Pro Glu Tyr
65                  70                  75                  80

Pro Gly Pro Ser His Arg Ile Lys Lys Thr Val Gln Val Glu Gln Ser
                85                  90                  95

Lys Val Leu Ile Lys Glu Gly Gly Val Gln Leu Leu Leu Thr Ile Val
            100                 105                 110

Asp Thr Pro Gly Phe Gly Asp Ala Val Asp Asn Ser Asn Cys Trp Gln
            115                 120                 125

Pro Val Ile Asp Tyr Ile Asp Ser Lys Phe Glu Asp Tyr Leu Asn Ala
            130                 135                 140

Glu Ser Arg Val Asn Arg Arg Gln Met Pro Asp Asn Arg Val Gln Cys
145                 150                 155                 160

Cys Leu Tyr Phe Ile Ala Pro Ser Gly His Gly Leu Lys Pro Leu Asp
                165                 170                 175

Ile Glu Phe Met Lys Arg Leu His Glu Lys Val Asn Ile Ile Pro Leu
            180                 185                 190

Ile Ala Lys Ala Asp Thr Leu Thr Pro Glu Glu Cys Gln Gln Phe Lys
            195                 200                 205

Lys Gln Ile Met Lys Glu Ile Gln Glu His Lys Ile Lys Ile Tyr Glu
            210                 215                 220

Phe Pro Glu Thr Asp Asp Glu Glu Asn Lys Leu Val Lys Lys Ile
225                 230                 235                 240

Lys Asp Arg Leu Pro Leu Ala Val Val Gly Ser Asn Thr Ile Ile Glu
                245                 250                 255

Val Asn Gly Lys Arg Val Arg Gly Arg Gln Tyr Pro Trp Gly Val Ala
            260                 265                 270

Glu Val Glu Asn Gly Glu His Cys Asp Phe Thr Ile Leu Arg Asn Met
            275                 280                 285

Leu Ile Arg Thr His Met Gln Asp Leu Lys Asp Val Thr Asn Asn Val
            290                 295                 300

His Tyr Glu Asn Tyr Arg Ser Arg Lys Leu Ala Ala Val Thr Tyr Asn
305                 310                 315                 320
```

```
Gly Val Asp Asn Asn Lys Asn Lys Gly Gln Leu Thr Lys Ser Pro Leu
            325                 330                 335

Ala Gln Met Glu Glu Arg Arg Glu His Val Ala Lys Met Lys Lys
        340                 345                 350

Met Glu Met Glu Met Glu Gln Val Phe Glu Met Lys Val Lys Glu Lys
        355                 360                 365

Val Gln Lys Leu Lys Asp Ser Glu Ala Glu Leu Gln Arg Arg His Glu
    370                 375                 380

Gln Met Lys Lys Asn Leu Glu Ala Gln His Lys Glu Leu Glu Glu Lys
385                 390                 395                 400

Arg Arg Gln Phe Glu Asp Glu Lys Ala Asn Trp Glu Ala Gln Gln Arg
                405                 410                 415

Ile Leu Glu Gln Gln Asn Ser Ser Arg Thr Leu Glu Lys Asn Lys Lys
            420                 425                 430

Lys Gly Lys Ile Phe Leu Glu His His His His His His
            435                 440                 445

<210> SEQ ID NO 9
<211> LENGTH: 368
<212> TYPE: PRT
<213> ORGANISM: Artificial Sequence
<220> FEATURE:
<223> OTHER INFORMATION: human Septin-3, His tagged

<400> SEQUENCE: 9

Met Ser Lys Gly Leu Pro Glu Thr Arg Thr Asp Ala Ala Met Ser Glu
1               5                   10                  15

Leu Val Pro Glu Pro Arg Pro Lys Pro Ala Val Pro Met Lys Pro Met
            20                  25                  30

Ser Ile Asn Ser Asn Leu Leu Gly Tyr Ile Gly Ile Asp Thr Ile Ile
        35                  40                  45

Glu Gln Met Arg Lys Lys Thr Met Lys Thr Gly Phe Asp Phe Asn Ile
    50                  55                  60

Met Val Val Gly Gln Ser Gly Leu Gly Lys Ser Thr Leu Val Asn Thr
65                  70                  75                  80

Leu Phe Lys Ser Gln Val Ser Arg Lys Ala Ser Ser Trp Asn Arg Glu
            85                  90                  95

Glu Lys Ile Pro Lys Thr Val Glu Ile Lys Ala Ile Gly His Val Ile
            100                 105                 110

Glu Glu Gly Gly Val Lys Met Lys Leu Thr Val Ile Asp Thr Pro Gly
        115                 120                 125

Phe Gly Asp Gln Ile Asn Asn Glu Asn Cys Trp Glu Pro Ile Glu Lys
            130                 135                 140

Tyr Ile Asn Glu Gln Tyr Glu Lys Phe Leu Lys Glu Glu Val Asn Ile
145                 150                 155                 160

Ala Arg Lys Lys Arg Ile Pro Asp Thr Arg Val His Cys Cys Leu Tyr
                165                 170                 175

Phe Ile Ser Pro Thr Gly His Ser Leu Arg Pro Leu Asp Leu Glu Phe
            180                 185                 190

Met Lys His Leu Ser Lys Val Val Asn Ile Ile Pro Val Ile Ala Lys
        195                 200                 205

Ala Asp Thr Met Thr Leu Glu Glu Lys Ser Glu Phe Lys Gln Arg Val
    210                 215                 220

Arg Lys Glu Leu Glu Val Asn Gly Ile Glu Phe Tyr Pro Gln Lys Glu
225                 230                 235                 240
```

-continued

```
Phe Asp Glu Asp Leu Glu Asp Lys Thr Glu Asn Asp Lys Ile Arg Gln
                245                 250                 255

Glu Ser Met Pro Phe Ala Val Val Gly Ser Lys Glu Tyr Gln Val
        260                 265                 270

Asn Gly Lys Arg Val Leu Gly Arg Lys Thr Pro Trp Gly Ile Ile Glu
            275                 280                 285

Val Glu Asn Leu Asn His Cys Glu Phe Ala Leu Leu Arg Asp Phe Val
290                 295                 300

Ile Arg Thr His Leu Gln Asp Leu Lys Glu Val Thr His Asn Ile His
305                 310                 315                 320

Tyr Glu Thr Tyr Arg Ala Lys Arg Leu Asn Asp Asn Gly Gly Leu Pro
                325                 330                 335

Pro Gly Glu Gly Leu Leu Gly Thr Val Leu Pro Pro Val Pro Ala Thr
            340                 345                 350

Pro Cys Pro Thr Ala Glu Leu Glu His His His His His His
            355                 360                 365
```

```
<210> SEQ ID NO 10
<211> LENGTH: 379
<212> TYPE: PRT
<213> ORGANISM: Artificial Sequence
<220> FEATURE:
<223> OTHER INFORMATION: human Septin-5, His tagged

<400> SEQUENCE: 10

Met Ser Thr Gly Leu Arg Tyr Lys Ser Lys Leu Ala Thr Pro Glu Asp
1               5                   10                  15

Lys Gln Asp Ile Asp Lys Gln Tyr Val Gly Phe Ala Thr Leu Pro Asn
                20                  25                  30

Gln Val His Arg Lys Ser Val Lys Lys Gly Phe Asp Phe Thr Leu Met
            35                  40                  45

Val Ala Gly Glu Ser Gly Leu Gly Lys Ser Thr Leu Val His Ser Leu
50                  55                  60

Phe Leu Thr Asp Leu Tyr Lys Asp Arg Lys Leu Leu Ser Ala Glu Glu
65                  70                  75                  80

Arg Ile Ser Gln Thr Val Glu Ile Leu Lys His Thr Val Asp Ile Glu
                85                  90                  95

Glu Lys Gly Val Lys Leu Lys Leu Thr Ile Val Asp Thr Pro Gly Phe
            100                 105                 110

Gly Asp Ala Val Asn Asn Thr Glu Cys Trp Lys Pro Ile Thr Asp Tyr
        115                 120                 125

Val Asp Gln Gln Phe Glu Gln Tyr Phe Arg Asp Glu Ser Gly Leu Asn
130                 135                 140

Arg Lys Asn Ile Gln Asp Asn Arg Val His Cys Cys Leu Tyr Phe Ile
145                 150                 155                 160

Ser Pro Phe Gly His Gly Leu Arg Pro Val Asp Val Gly Phe Met Lys
                165                 170                 175

Ala Leu His Glu Lys Val Asn Ile Val Pro Leu Ile Ala Lys Ala Asp
            180                 185                 190

Cys Leu Val Pro Ser Glu Ile Arg Lys Leu Lys Glu Arg Ile Arg Glu
        195                 200                 205

Glu Ile Asp Lys Phe Gly Ile His Val Tyr Gln Phe Pro Glu Cys Asp
210                 215                 220

Ser Asp Glu Asp Glu Asp Phe Lys Gln Gln Asp Arg Glu Leu Lys Glu
225                 230                 235                 240
```

-continued

Ser Ala Pro Phe Ala Val Ile Gly Ser Asn Thr Val Val Glu Ala Lys
                245                 250                 255

Gly Gln Arg Val Arg Gly Arg Leu Tyr Pro Trp Gly Ile Val Glu Val
            260                 265                 270

Glu Asn Gln Ala His Cys Asp Phe Val Lys Leu Arg Asn Met Leu Ile
        275                 280                 285

Arg Thr His Met His Asp Leu Lys Asp Val Thr Cys Asp Val His Tyr
    290                 295                 300

Glu Asn Tyr Arg Ala His Cys Ile Gln Gln Met Thr Ser Lys Leu Thr
305                 310                 315                 320

Gln Asp Ser Arg Met Glu Ser Pro Ile Pro Ile Leu Pro Leu Pro Thr
                325                 330                 335

Pro Asp Ala Glu Thr Glu Lys Leu Ile Arg Met Lys Asp Glu Glu Leu
            340                 345                 350

Arg Arg Met Gln Glu Met Leu Gln Arg Met Lys Gln Gln Met Gln Asp
        355                 360                 365

Gln Leu Glu His His His His His His
    370                 375

<210> SEQ ID NO 11
<211> LENGTH: 444
<212> TYPE: PRT
<213> ORGANISM: Artificial Sequence
<220> FEATURE:
<223> OTHER INFORMATION: human Septin-6, His tagged

<400> SEQUENCE: 11

Met Ala Ala Thr Asp Ile Ala Arg Gln Val Gly Glu Gly Cys Arg Thr
1               5                   10                  15

Val Pro Leu Ala Gly His Val Gly Phe Asp Ser Leu Pro Asp Gln Leu
                20                  25                  30

Val Asn Lys Ser Val Ser Gln Gly Phe Cys Phe Asn Ile Leu Cys Val
            35                  40                  45

Gly Glu Thr Gly Leu Gly Lys Ser Thr Leu Met Asp Thr Leu Phe Asn
        50                  55                  60

Thr Lys Phe Glu Gly Glu Pro Ala Thr His Thr Gln Pro Gly Val Gln
65                  70                  75                  80

Leu Gln Ser Asn Thr Tyr Asp Leu Gln Glu Ser Asn Val Arg Leu Lys
                85                  90                  95

Leu Thr Ile Val Ser Thr Val Gly Phe Gly Asp Gln Ile Asn Lys Glu
            100                 105                 110

Asp Ser Tyr Lys Pro Ile Val Glu Phe Ile Asp Ala Gln Phe Glu Ala
        115                 120                 125

Tyr Leu Gln Glu Glu Leu Lys Ile Arg Arg Val Leu His Thr Tyr His
130                 135                 140

Asp Ser Arg Ile His Val Cys Leu Tyr Phe Ile Ala Pro Thr Gly His
145                 150                 155                 160

Ser Leu Lys Ser Leu Asp Leu Val Thr Met Lys Lys Leu Asp Ser Lys
                165                 170                 175

Val Asn Ile Ile Pro Ile Ile Ala Lys Ala Asp Ala Ile Ser Lys Ser
            180                 185                 190

Glu Leu Thr Lys Phe Lys Ile Lys Ile Thr Ser Glu Leu Val Ser Asn
        195                 200                 205

Gly Val Gln Ile Tyr Gln Phe Pro Thr Asp Asp Glu Ser Val Ala Glu
    210                 215                 220

```
Ile Asn Gly Thr Met Asn Ala His Leu Pro Phe Ala Val Ile Gly Ser
225                 230                 235                 240

Thr Glu Glu Leu Lys Ile Gly Asn Lys Met Met Arg Ala Arg Gln Tyr
            245                 250                 255

Pro Trp Gly Thr Val Gln Val Glu Asn Glu Ala His Cys Asp Phe Val
        260                 265                 270

Lys Leu Arg Glu Met Leu Ile Arg Val Asn Met Glu Asp Leu Arg Glu
    275                 280                 285

Gln Thr His Thr Arg His Tyr Glu Leu Tyr Arg Arg Cys Lys Leu Glu
290                 295                 300

Glu Met Gly Phe Lys Asp Thr Asp Pro Asp Ser Lys Pro Phe Ser Leu
305                 310                 315                 320

Gln Glu Thr Tyr Glu Ala Lys Arg Asn Glu Phe Leu Gly Leu Gln
            325                 330                 335

Lys Lys Glu Glu Glu Met Arg Gln Met Phe Val Gln Arg Val Lys Glu
                340                 345                 350

Lys Glu Ala Glu Leu Lys Glu Ala Glu Lys Glu Leu His Glu Lys Phe
            355                 360                 365

Asp Arg Leu Lys Lys Leu His Gln Asp Glu Lys Lys Lys Leu Glu Asp
370                 375                 380

Lys Lys Lys Ser Leu Asp Asp Glu Val Asn Ala Phe Lys Gln Arg Lys
385                 390                 395                 400

Thr Ala Ala Glu Leu Pro Gln Ser Gln Gly Ser Gln Ala Gly Gly Ser
                405                 410                 415

Gln Thr Leu Lys Arg Asp Lys Lys Asn Asn Pro Trp Leu Cys
            420                 425                 430

Thr Glu Leu Glu His His His His His His His
            435                 440

<210> SEQ ID NO 12
<211> LENGTH: 439
<212> TYPE: PRT
<213> ORGANISM: Artificial Sequence
<220> FEATURE:
<223> OTHER INFORMATION: human Septin-11, His tagged

<400> SEQUENCE: 12

Met Ala Val Ala Val Gly Arg Pro Ser Asn Glu Glu Leu Arg Asn Leu
1               5                   10                  15

Ser Leu Ser Gly His Val Gly Phe Asp Ser Leu Pro Asp Gln Leu Val
            20                  25                  30

Asn Lys Ser Thr Ser Gln Gly Phe Cys Phe Asn Ile Leu Cys Val Gly
        35                  40                  45

Glu Thr Gly Ile Gly Lys Ser Thr Leu Met Asp Thr Leu Phe Asn Thr
    50                  55                  60

Lys Phe Glu Ser Asp Pro Ala Thr His Asn Glu Pro Gly Val Arg Leu
65                  70                  75                  80

Lys Ala Arg Ser Tyr Glu Leu Gln Glu Ser Asn Val Arg Leu Lys Leu
                85                  90                  95

Thr Ile Val Asp Thr Val Gly Phe Gly Asp Gln Ile Asn Lys Asp Asp
            100                 105                 110

Ser Tyr Lys Pro Ile Val Glu Tyr Ile Asp Ala Gln Phe Glu Ala Tyr
        115                 120                 125

Leu Gln Glu Glu Leu Lys Ile Lys Arg Ser Leu Phe Asn Tyr His Asp
    130                 135                 140
```

Thr Arg Ile His Ala Cys Leu Tyr Phe Ile Ala Pro Thr Gly His Ser
145                 150                 155                 160

Leu Lys Ser Leu Asp Leu Val Thr Met Lys Lys Leu Asp Ser Lys Val
            165                 170                 175

Asn Ile Ile Pro Ile Ile Ala Lys Ala Asp Thr Ile Ala Lys Asn Glu
            180                 185                 190

Leu His Lys Phe Lys Ser Lys Ile Met Ser Glu Leu Val Ser Asn Gly
            195                 200                 205

Val Gln Ile Tyr Gln Phe Pro Thr Asp Glu Glu Thr Val Ala Glu Ile
210                 215                 220

Asn Ala Thr Met Ser Val His Leu Pro Phe Ala Val Val Gly Ser Thr
225                 230                 235                 240

Glu Glu Val Lys Ile Gly Asn Lys Met Ala Lys Ala Arg Gln Tyr Pro
            245                 250                 255

Trp Gly Val Val Gln Val Glu Asn Glu Asn His Cys Asp Phe Val Lys
            260                 265                 270

Leu Arg Glu Met Leu Ile Arg Val Asn Met Glu Asp Leu Arg Glu Gln
            275                 280                 285

Thr His Thr Arg His Tyr Glu Leu Tyr Arg Arg Cys Lys Leu Glu Glu
290                 295                 300

Met Gly Phe Lys Asp Thr Asp Pro Asp Ser Lys Pro Phe Ser Leu Gln
305                 310                 315                 320

Glu Thr Tyr Glu Ala Lys Arg Asn Glu Phe Leu Gly Glu Leu Gln Lys
            325                 330                 335

Lys Glu Glu Glu Met Arg Gln Met Phe Val Met Arg Val Lys Glu Lys
            340                 345                 350

Glu Ala Glu Leu Lys Glu Ala Glu Lys Glu Leu His Glu Lys Phe Asp
            355                 360                 365

Leu Leu Lys Arg Thr His Gln Glu Lys Lys Lys Val Glu Asp Lys
370                 375                 380

Lys Lys Glu Leu Glu Glu Val Asn Asn Phe Gln Lys Lys Ala
385                 390                 395                 400

Ala Ala Gln Leu Leu Gln Ser Gln Ala Gln Gln Ser Gly Ala Gln Gln
            405                 410                 415

Thr Lys Lys Asp Lys Asp Lys Lys Asn Ala Ser Phe Thr Leu Glu His
            420                 425                 430

His His His His His His
        435

<210> SEQ ID NO 13
<211> LENGTH: 6925
<212> TYPE: DNA
<213> ORGANISM: Artificial Sequence
<220> FEATURE:
<223> OTHER INFORMATION: pTriEx-1-Septin-7, His tagged

<400> SEQUENCE: 13
ggggaattgt gagcggataa caattccccg gagttaatcc gggacccttta attcaaccca     60 acacaatata ttatagttaa ataagaatta ttatcaaatc atttgtatat taattaaaat    120
actatactgt aaattacatt ttatttacaa tcaaaggaga tataccatgt cggtcagtgc    180
gagatccgct gctgctgagg agaggagcgt caacagcagc accatggtag ctcaacagaa    240
gaaccttgaa ggctatgtgg gatttgccaa tctcccaaat caagtataca gaaaatcggt    300
gaagagaggt tttgaattca cgcttatggt agtgggtgaa tctggattgg gaaagtcgac    360

| | |
|---|---|
| attaatcaac tcattattcc tcacagattt gtattctcca gagtatccag gtccttctca | 420 |
| tagaattaaa aagactgtac aggtggaaca atccaaagtt ttaatcaaag aaggtggtgt | 480 |
| tcagttgctg ctcacaatag ttgatacccc aggatttgga gatgcagtgg ataatagtaa | 540 |
| ttgctggcag cctgttatcg actacattga tagtaaattt gaggactacc taaatgcaga | 600 |
| atcacgagtg aacagacgtc agatgcctga taacagggtg cagtgttgtt tatacttcat | 660 |
| tgctccttca ggacatggac ttaaaccatt ggatattgag tttatgaagc gtttgcatga | 720 |
| aaaagtgaat atcatcccac ttattgccaa agcagacaca ctcacaccag ggaatgcca | 780 |
| acagtttaaa aaacagataa tgaaagaaat ccaagaacat aaaattaaaa tatacgaatt | 840 |
| tccagaaaca gatgatgaag aagaaaataa acttgttaaa aagataaagg accgtttacc | 900 |
| tcttgctgtg gtaggtagta atactatcat tgaagttaat ggcaaaaggg tcagaggaag | 960 |
| gcagtatcct tggggtgttg ctgaagttga aaatggtgaa cattgtgatt ttacaatcct | 1020 |
| aagaaatatg ttgataagaa cacacatgca ggacttgaaa gatgttacta ataatgtcca | 1080 |
| ctatgagaac tacagaagca gaaaacttgc agctgtgact tataatggag ttgataacaa | 1140 |
| caagaataaa gggcagctga ctaagagccc tctggcacaa atggaagaag aaagaaggga | 1200 |
| gcatgtagct aaaatgaaga agatggagat ggagatggag caggtgtttg agatgaaggt | 1260 |
| caaagaaaaa gttcaaaaac tgaaggactc tgaagctgag ctccagcggc gccatgagca | 1320 |
| aatgaaaaag aatttggaag cacagcacaa agaattggag gaaaaacgtc gtcagttcga | 1380 |
| ggatgagaaa gcaaactggg aagctcaaca acgtatttta gaacaacaga actcttcaag | 1440 |
| aaccttggaa aagaacaaga agaaagggaa gatctttctc gagcaccacc atcaccatca | 1500 |
| ccatcactaa gtgattaacc tcaggtgcag gctgcctatc agaaggtggt ggctggtgtg | 1560 |
| gccaatgccc tggctcacaa ataccactga gatcgatctt tttccctctg ccaaaaatta | 1620 |
| tggggacatc atgaagcccc ttgagcatct gacttctggc taataaagga aatttatttt | 1680 |
| cattgcaata gtgtgttgga atttttttgtg tctctcactc ggaaggacat atgggagggc | 1740 |
| aaatcattta aaacatcaga atgagtattt ggtttagagt ttggcaacat atgcccatat | 1800 |
| gtaactagca taacccccttg gggcctctaa acgggtcttg aggggttttt tgctgaaagc | 1860 |
| atgcggagga aattctcctt gaagtttccc tggtgttcaa agtaaaggag tttgcaccag | 1920 |
| acgcacctct gttcactggt ccggcgtatt aaaacgat acattgttat tagtacattt | 1980 |
| attaagcgct agattctgtg cgttgttgat ttacagacaa ttgttgtacg tattttaata | 2040 |
| attcattaaa tttataatct ttagggtggt atgttagagc gaaaatcaaa tgattttcag | 2100 |
| cgtctttata tctgaattta aatattaaat cctcaataga tttgtaaaat aggtttcgat | 2160 |
| tagtttcaaa caagggttgt ttttccgaac cgatggctgg actatctaat ggattttcgc | 2220 |
| tcaacgccac aaaacttgcc aaatcttgta gcagcaatct agctttgtcg atattcgttt | 2280 |
| gtgttttgtt ttgtaataaa ggttcgacgt cgttcaaaat attatgcgct tttgtatttc | 2340 |
| tttcatcact gtcgttagtg tacaattgac tcgacgtaaa cacgttaaat agagcttgga | 2400 |
| catatttaac atcgggcgtg ttagctttat taggccgatt atcgtcgtcg tcccaaccct | 2460 |
| cgtcgttaga agttgcttcc gaagacgatt ttgccatagc cacacgacgc ctattaattg | 2520 |
| tgtcggctaa cacgtccgcg atcaaatttg tagttgagct ttttggaatt atttctgatt | 2580 |
| gcgggcgttt ttgggcgggt ttcaatctaa ctgtgcccga ttttaattca gacaacacgt | 2640 |
| tagaaagcga tggtgcaggc ggtggtaaca tttcagacgg caaatctact aatgcgggcg | 2700 |
| gtggtggagc tgatgataaa tctaccatcg gtggaggcgc aggcggggct ggcggcggag | 2760 |

```
gcggaggcgg aggtggtggc ggtgatgcag acggcggttt aggctcaaat gtctctttag    2820
gcaacacagt cggcacctca actattgtac tggtttcggg cgccgttttt ggtttgaccg    2880
gtctgagacg agtgcgattt ttttcgtttc taatagcttc caacaattgt tgtctgtcgt    2940
ctaaaggtgc agcgggttga ggttccgtcg gcattggtgg agcgggcggc aattcagaca    3000
tcgatggtgg tggtggtggt ggaggcgctg gaatgttagg cacgggagaa ggtggtggcg    3060
gcggtgccgc cggtataatt tgttctggtt tagtttgttc gcgcacgatt gtgggcaccg    3120
gcgcaggcgc cgctggctgc acaacggaag gtcgtctgct tcgaggcagc gcttggggtg    3180
gtggcaattc aatattataa ttggaataca aatcgtaaaa atctgctata agcattgtaa    3240
tttcgctatc gtttaccgtg ccgatattta acaaccgctc aatgtaagca attgtattgt    3300
aaagagattg tctcaagctc ggaacgctgc gctcggtcgt tcggctgcgg cgagcggtat    3360
cagctcactc aaaggcggta atacggttat ccacagaatc aggggataac gcaggaaaga    3420
acatgtgagc aaaaggccag caaaaggcca ggaaccgtaa aaaggccgcg ttgctggcgt    3480
ttttccatag gctccgcccc cctgacgagc atcacaaaaa tcgacgctca agtcagaggt    3540
ggcgaaaccc gacaggacta taaagatacc aggcgtttcc ccctggaagc tccctcgtgc    3600
gctctcctgt tccgaccctg ccgcttaccg gatacctgtc cgcctttctc ccttcgggaa    3660
gcgtggcgct ttctcaatgc tcacgctgta ggtatctcag ttcggtgtag gtcgttcgct    3720
ccaagctggg ctgtgtgcac gaaccccccg ttcagcccga ccgctgcgcc ttatccggta    3780
actatcgtct tgagtccaac ccggtaagac acgacttatc gccactggca gcagccactg    3840
gtaacaggat tagcagagcg aggtatgtag gcggtgctac agagttcttg aagtggtggc    3900
ctaactacgg ctacactaga aggacagtat ttggtatctg cgctctgctg aagccagtta    3960
ccttcggaaa aagagttggt agctcttgat ccggcaaaca aaccaccgct ggtagcggtg    4020
gtttttttgt ttgcaagcag cagattacgc gcagaaaaaa aggatctcaa gaagatcctt    4080
tgttaccaat gcttaatcag tgaggcacct atctcagcga tctgtctatt tcgttcatcc    4140
atagttgcct gactccccgt cgtgtagata actacgatac gggagggctt accatctggc    4200
cccagtgctg caatgatacc gcgagaccca cgctcaccgg ctccagattt atcagcaata    4260
aaccagccag ccggaagggc cgagcgcaga agtggtcctg caactttatc cgcctccatc    4320
cagtctatta attgttgccg ggaagctaga gtaagtagtt cgccagttaa tagtttgcgc    4380
aacgttgttg ccattgctac aggcatcgtg gtgtcacgct cgtcgtttgg tatggcttca    4440
ttcagctccg gttcccaacg atcaaggcga gttacatgat cccccatgtt gtgcaaaaaa    4500
gcggttagct ccttcggtcc tccgatcgtt gtcagaagta agttggccgc agtgttatca    4560
ctcatggtta tggcagcact gcataattct cttactgtca tgccatccgt aagatgcttt    4620
tctgtgactg gtgagtactc aaccaagtca ttctgagaat agtgtatgcg gcgaccgagt    4680
tgctcttgcc cggcgtcaat acgggataat accgcgccac atagcagaac tttaaaagtg    4740
ctcatcattg gaaaacgttc ttcggggcga aaactctcaa ggatcttacc gctgttgaga    4800
tccagttcga tgtaacccac tcgtgcaccc aactgatctt cagcatcttt tactttcacc    4860
agcgtttctg ggtgagcaaa aacaggaagg caaaatgccg caaaaaaggg aataagggcg    4920
acacggaaat gttgaatact catactcttc ctttttcaat attattgaag catttatcag    4980
ggttattgtc tcatgtccgc gcgtttcctg catcttttaa tcaaatccca agatgtgtat    5040
aaaccaccaa actgccaaaa aatgaaaact gtcgacaagc tctgtccgtt tgctggcaac    5100
```

|  |  |  |  |  |  |
|---|---|---|---|---|---|
| tgcaagggtc | tcaatcctat | ttgtaattat | tgaataataa | aacaattata | aatgtcaaat | 5160 |
| ttgtttttta | ttaacgatac | aaaccaaacg | caacaagaac | atttgtagta | ttatctataa | 5220 |
| ttgaaaacgc | gtagttataa | tcgctgaggt | aatatttaaa | atcattttca | aatgattcac | 5280 |
| agttaatttg | cgacaatata | attttatttt | cacataaact | agacgccttg | tcgtcttctt | 5340 |
| cttcgtattc | cttctctttt | tcattttct | cttcataaaa | attaacatag | ttattatcgt | 5400 |
| atccatatat | gtatctatcg | tatagagtaa | attttttgtt | gtcataaata | tatatgtctt | 5460 |
| ttttaatggg | gtgtatagta | ccgctgcgca | tagttttct | gtaatttaca | acagtgctat | 5520 |
| tttctggtag | ttcttcggag | tgtgttgctt | taattattaa | atttatataa | tcaatgaatt | 5580 |
| tgggatcgtc | ggttttgtac | aatatgttgc | cggcatagta | cgcagcttct | tctagttcaa | 5640 |
| ttacaccatt | ttttagcagc | accggattaa | cataactttc | caaaatgttg | tacgaaccgt | 5700 |
| taaacaaaaa | cagttcacct | cccttttcta | tactattgtc | tgcgagcagt | tgtttgttgt | 5760 |
| taaaaataac | agccattgta | atgagacgca | caaactaata | tcacaaactg | gaaatgtcta | 5820 |
| tcaatatata | gttgctctag | ttattaatag | taatcaatta | cggggtcatt | agttcatagc | 5880 |
| ccatatatgg | agttccgcgt | tacataactt | acggtaaatg | gcccgcctgg | ctgaccgccc | 5940 |
| aacgacccc | gcccattgac | gtcaataatg | acgtatgttc | ccatagtaac | gccaataggg | 6000 |
| actttccatt | gacgtcaatg | ggtggactat | ttacggtaaa | ctgcccactt | ggcagtacat | 6060 |
| caagtgtatc | atatgccaag | tacgcccct | attgacgtca | atgacggtaa | atggcccgcc | 6120 |
| tggcattatg | cccagtacat | gaccttatgg | gactttccta | cttggcagta | catctacgta | 6180 |
| ttagtcatcg | ctattaccat | gcatggtcga | ggtgagcccc | acgttctgct | tcactctccc | 6240 |
| catctccccc | cctccccac | ccccaatttt | gtatttattt | attttttaat | tattttgtgc | 6300 |
| agcgatgggg | gcgggggggg | ggggggggcg | cgcgccaggc | ggggcggggc | ggggcgaggg | 6360 |
| gcggggcggg | gcgaggcgga | gaggtgcggc | ggcagccaat | cagagcggcg | cgctccgaaa | 6420 |
| gtttcctttt | atggcgaggc | ggcggcggcg | cggccctat | aaaaagcgaa | gcgcgcggcg | 6480 |
| ggcgggagtc | gctgcgacgc | tgccttcgcc | ccgtgccccg | ctccgccgcc | gcctcgcgcc | 6540 |
| gcccgccccg | gctctgactg | accgcgttac | tcccacaggt | gagcgggcgg | gacggccctt | 6600 |
| ctccttcggg | ctgtaattag | cgcttggttt | aatgacggct | tgtttctttt | ctgtggctgc | 6660 |
| gtgaaagcct | tgaggggctc | cgggagggcc | ctttgtgcgg | gggagcggc | tcggggctgt | 6720 |
| ccgcgggggg | acggctgcct | tcgggggga | cgggcaggg | cggggttcgg | cttctggcgt | 6780 |
| gtgaccggcg | gctctagagc | ctctgctaac | catgttcatg | ccttcttctt | tttcctacag | 6840 |
| ctcctgggca | acgtgctggt | tattgtgctg | tctcatcatt | ttggcaaaga | attggatcgg | 6900 |
| accgaaatta | atacgactca | ctata |  |  |  | 6925 |

<210> SEQ ID NO 14
<211> LENGTH: 367
<212> TYPE: PRT
<213> ORGANISM: Homo sapiens

<400> SEQUENCE: 14

Met Asp Lys Glu Tyr Val Gly Phe Ala Ala Leu Pro Asn Gln Leu His
1               5                   10                  15

Arg Lys Ser Val Lys Lys Gly Phe Asp Phe Thr Leu Met Val Ala Gly
            20                  25                  30

Glu Ser Gly Leu Gly Lys Ser Thr Leu Ile Asn Ser Leu Phe Leu Thr
        35                  40                  45

```
Asn Leu Tyr Glu Asp Arg Gln Val Pro Glu Ala Ser Ala Arg Leu Thr
 50                  55                  60

Gln Thr Leu Ala Ile Glu Arg Arg Gly Val Glu Ile Glu Glu Gly Gly
 65                  70                  75                  80

Val Lys Val Lys Leu Thr Leu Val Asp Thr Pro Gly Phe Gly Asp Ser
                 85                  90                  95

Val Asp Cys Ser Asp Cys Trp Leu Pro Val Val Lys Phe Ile Glu Glu
            100                 105                 110

Gln Phe Glu Gln Tyr Leu Arg Asp Glu Ser Gly Leu Asn Arg Lys Asn
        115                 120                 125

Ile Gln Asp Ser Arg Val His Cys Cys Leu Tyr Phe Ile Ser Pro Phe
130                 135                 140

Gly Arg Gly Leu Arg Pro Leu Asp Val Ala Phe Leu Arg Ala Val His
145                 150                 155                 160

Glu Lys Val Asn Ile Ile Pro Val Ile Gly Lys Ala Asp Ala Leu Met
                165                 170                 175

Pro Gln Glu Thr Gln Ala Leu Lys Gln Lys Ile Arg Asp Gln Leu Lys
            180                 185                 190

Glu Glu Glu Ile His Ile Tyr Gln Phe Pro Glu Cys Asp Ser Asp Glu
        195                 200                 205

Asp Glu Asp Phe Lys Arg Gln Asp Ala Glu Met Lys Glu Ser Ile Pro
210                 215                 220

Phe Ala Val Val Gly Ser Cys Glu Val Val Arg Asp Gly Gly Asn Arg
225                 230                 235                 240

Pro Val Arg Gly Arg Arg Tyr Ser Trp Gly Thr Val Glu Val Glu Asn
                245                 250                 255

Pro His His Cys Asp Phe Leu Asn Leu Arg Arg Met Leu Val Gln Thr
            260                 265                 270

His Leu Gln Asp Leu Lys Glu Val Thr His Asp Leu Leu Tyr Glu Gly
        275                 280                 285

Tyr Arg Ala Arg Cys Leu Gln Ser Leu Ala Arg Pro Gly Ala Arg Asp
290                 295                 300

Arg Ala Ser Arg Ser Lys Leu Ser Arg Gln Ser Ala Thr Glu Ile Pro
305                 310                 315                 320

Leu Pro Met Leu Pro Leu Ala Asp Thr Glu Lys Leu Ile Arg Glu Lys
                325                 330                 335

Asp Glu Glu Leu Arg Arg Met Gln Glu Met Leu Glu Lys Met Gln Ala
            340                 345                 350

Gln Met Gln Gln Ser Gln Ala Gln Gly Glu Gln Ser Asp Ala Leu
        355                 360                 365

<210> SEQ ID NO 15
<211> LENGTH: 361
<212> TYPE: PRT
<213> ORGANISM: Homo sapiens

<400> SEQUENCE: 15

Met Ser Lys Gln Gln Pro Thr Gln Phe Ile Asn Pro Glu Thr Pro Gly
  1               5                  10                  15

Tyr Val Gly Phe Ala Asn Leu Pro Asn Gln Val His Arg Lys Ser Val
                 20                  25                  30

Lys Lys Gly Phe Glu Phe Thr Leu Met Val Val Gly Glu Ser Gly Leu
            35                  40                  45

Gly Lys Ser Thr Leu Ile Asn Ser Leu Phe Leu Thr Asp Leu Tyr Pro
        50                  55                  60
```

```
Glu Arg Val Ile Pro Gly Ala Ala Glu Lys Ile Glu Arg Thr Val Gln
 65                  70                  75                  80

Ile Glu Ala Ser Thr Val Glu Ile Glu Arg Gly Val Lys Leu Arg
                 85                  90                  95

Leu Thr Val Val Asp Thr Pro Gly Tyr Gly Asp Ala Ile Asn Cys Arg
                100                 105                 110

Asp Cys Phe Lys Thr Ile Ile Ser Tyr Ile Asp Glu Gln Phe Glu Arg
                115                 120                 125

Tyr Leu His Asp Glu Ser Gly Leu Asn Arg Arg His Ile Ile Asp Asn
            130                 135                 140

Arg Val His Cys Cys Phe Tyr Phe Ile Ser Pro Phe Gly His Gly Leu
145                 150                 155                 160

Lys Pro Leu Asp Val Ala Phe Met Lys Ala Ile His Asn Lys Val Asn
                165                 170                 175

Ile Val Pro Val Ile Ala Lys Ala Asp Thr Leu Thr Leu Lys Glu Arg
                180                 185                 190

Glu Arg Leu Lys Lys Arg Ile Leu Asp Glu Ile Glu His Asn Ile
            195                 200                 205

Lys Ile Tyr His Leu Pro Asp Ala Glu Ser Asp Glu Asp Phe
210                 215                 220

Lys Glu Gln Thr Arg Leu Leu Lys Ala Ser Ile Pro Phe Ser Val Val
225                 230                 235                 240

Gly Ser Asn Gln Leu Ile Glu Ala Lys Gly Lys Lys Val Arg Gly Arg
                245                 250                 255

Leu Tyr Pro Trp Gly Val Val Glu Val Glu Asn Pro Glu His Asn Asp
                260                 265                 270

Phe Leu Lys Leu Arg Thr Met Leu Ile Thr His Met Gln Asp Leu Gln
            275                 280                 285

Glu Val Thr Gln Asp Leu His Tyr Glu Asn Phe Arg Ser Glu Arg Leu
            290                 295                 300

Lys Arg Gly Gly Arg Lys Val Glu Asn Glu Asp Met Asn Lys Asp Gln
305                 310                 315                 320

Ile Leu Leu Glu Lys Glu Ala Glu Leu Arg Arg Met Gln Glu Met Ile
                325                 330                 335

Ala Arg Met Gln Ala Gln Met Gln Met Gln Gly Gly Asp Gly
            340                 345                 350

Asp Gly Gly Ala Leu Gly His His Val
            355                 360

<210> SEQ ID NO 16
<211> LENGTH: 478
<212> TYPE: PRT
<213> ORGANISM: Homo sapiens

<400> SEQUENCE: 16

Met Asp Arg Ser Leu Gly Trp Gln Gly Asn Ser Val Pro Glu Asp Arg
  1               5                  10                  15

Thr Glu Ala Gly Ile Lys Arg Phe Leu Glu Asp Thr Thr Asp Asp Gly
                 20                  25                  30

Glu Leu Ser Lys Phe Val Lys Asp Phe Ser Gly Asn Ala Ser Cys His
             35                  40                  45

Pro Pro Glu Ala Lys Thr Trp Ala Ser Arg Pro Gln Val Pro Glu Pro
 50                  55                  60

Arg Pro Gln Ala Pro Asp Leu Tyr Asp Asp Asp Leu Glu Phe Arg Pro
```

```
            65                  70                  75                  80
        Pro Ser Arg Pro Gln Ser Ser Asp Asn Gln Gln Tyr Phe Cys Ala Pro
                        85                  90                  95

Ala Pro Leu Ser Pro Ser Ala Arg Pro Arg Ser Pro Trp Gly Lys Leu
                    100                 105                 110

Asp Pro Tyr Asp Ser Ser Glu Asp Lys Glu Tyr Val Gly Phe Ala
                115                 120                 125

Thr Leu Pro Asn Gln Val His Arg Lys Ser Val Lys Lys Gly Phe Asp
        130                 135                 140

Phe Thr Leu Met Val Ala Gly Glu Ser Gly Leu Gly Lys Ser Thr Leu
        145                 150                 155                 160

Val Asn Ser Leu Phe Leu Thr Asp Leu Tyr Arg Asp Arg Lys Leu Leu
                        165                 170                 175

Gly Ala Glu Glu Arg Ile Met Gln Thr Val Glu Ile Thr Lys His Ala
                    180                 185                 190

Val Asp Ile Glu Glu Lys Gly Val Arg Leu Arg Leu Thr Ile Val Asp
                195                 200                 205

Thr Pro Gly Phe Gly Asp Ala Val Asn Asn Thr Glu Cys Trp Lys Pro
        210                 215                 220

Val Ala Glu Tyr Ile Asp Gln Gln Phe Glu Gln Tyr Phe Arg Asp Glu
        225                 230                 235                 240

Ser Gly Leu Asn Arg Lys Asn Ile Gln Asp Asn Arg Val His Cys Cys
                        245                 250                 255

Leu Tyr Phe Ile Ser Pro Phe Gly His Gly Leu Arg Pro Leu Asp Val
                    260                 265                 270

Glu Phe Met Lys Ala Leu His Gln Arg Val Asn Ile Val Pro Ile Leu
                275                 280                 285

Ala Lys Ala Asp Thr Leu Thr Pro Pro Glu Val Asp His Lys Lys Arg
        290                 295                 300

Lys Ile Arg Glu Glu Ile Glu His Phe Gly Ile Lys Ile Tyr Gln Phe
        305                 310                 315                 320

Pro Asp Cys Asp Ser Asp Glu Asp Glu Asp Phe Lys Leu Gln Asp Gln
                        325                 330                 335

Ala Leu Lys Glu Ser Ile Pro Phe Ala Val Ile Gly Ser Asn Thr Val
                    340                 345                 350

Val Glu Ala Arg Gly Arg Arg Val Arg Gly Arg Leu Tyr Pro Trp Gly
                355                 360                 365

Ile Val Glu Val Glu Asn Pro Gly His Cys Asp Phe Val Lys Leu Arg
        370                 375                 380

Thr Met Leu Val Arg Thr His Met Gln Asp Leu Lys Asp Val Thr Arg
        385                 390                 395                 400

Glu Thr His Tyr Glu Asn Tyr Arg Ala Gln Cys Ile Gln Ser Met Thr
                        405                 410                 415

Arg Leu Val Val Lys Glu Arg Asn Arg Asn Lys Leu Thr Arg Glu Ser
                    420                 425                 430

Gly Thr Asp Phe Pro Ile Pro Ala Val Pro Pro Gly Thr Asp Pro Glu
                435                 440                 445

Thr Glu Lys Leu Ile Arg Glu Lys Asp Glu Leu Arg Arg Met Gln
        450                 455                 460

Glu Met Leu His Lys Ile Gln Lys Gln Met Lys Glu Asn Tyr
        465                 470                 475

<210> SEQ ID NO 17
```

```
<211> LENGTH: 483
<212> TYPE: PRT
<213> ORGANISM: Homo sapiens

<400> SEQUENCE: 17

Met Ala Ala Thr Asp Leu Glu Arg Phe Ser Asn Ala Glu Pro Glu Pro
1               5                   10                  15

Arg Ser Leu Ser Leu Gly Gly His Val Gly Phe Asp Ser Leu Pro Asp
            20                  25                  30

Gln Leu Val Ser Lys Ser Val Thr Gln Gly Phe Ser Phe Asn Ile Leu
        35                  40                  45

Cys Val Gly Glu Thr Gly Ile Gly Lys Ser Thr Leu Met Asn Thr Leu
50                  55                  60

Phe Asn Thr Thr Phe Glu Thr Glu Glu Ala Ser His His Glu Ala Cys
65                  70                  75                  80

Val Arg Leu Arg Pro Gln Thr Tyr Asp Leu Gln Glu Ser Asn Val Gln
                85                  90                  95

Leu Lys Leu Thr Ile Val Asp Ala Val Gly Phe Gly Asp Gln Ile Asn
            100                 105                 110

Lys Asp Glu Ser Tyr Arg Pro Ile Val Asp Tyr Ile Asp Ala Gln Phe
        115                 120                 125

Glu Asn Tyr Leu Gln Glu Leu Lys Ile Arg Arg Ser Leu Phe Asp
130                 135                 140

Tyr His Asp Thr Arg Ile His Val Cys Leu Tyr Phe Ile Thr Pro Thr
145                 150                 155                 160

Gly His Ser Leu Lys Ser Leu Asp Leu Val Thr Met Lys Lys Leu Asp
                165                 170                 175

Ser Lys Val Asn Ile Ile Pro Ile Ile Ala Lys Ala Asp Thr Ile Ser
            180                 185                 190

Lys Ser Glu Leu His Lys Phe Lys Ile Lys Ile Met Gly Glu Leu Val
        195                 200                 205

Ser Asn Gly Val Gln Ile Tyr Gln Phe Pro Thr Asp Asp Glu Ala Val
210                 215                 220

Ala Glu Ile Asn Ala Val Met Asn Ala His Leu Pro Phe Ala Val Val
225                 230                 235                 240

Gly Ser Thr Glu Glu Val Lys Val Gly Asn Lys Leu Val Arg Ala Arg
                245                 250                 255

Gln Tyr Pro Trp Gly Val Val Gln Val Glu Asn Glu Asn His Cys Asp
            260                 265                 270

Phe Val Lys Leu Arg Glu Met Leu Ile Arg Val Asn Met Glu Asp Leu
        275                 280                 285

Arg Glu Gln Thr His Ser Arg His Tyr Glu Leu Tyr Arg Arg Cys Lys
290                 295                 300

Leu Glu Glu Met Gly Phe Gln Asp Ser Asp Gly Asp Ser Gln Pro Phe
305                 310                 315                 320

Ser Leu Gln Glu Thr Tyr Glu Ala Lys Arg Lys Glu Phe Leu Ser Glu
                325                 330                 335

Leu Gln Arg Lys Glu Glu Met Arg Gln Met Phe Val Asn Lys Val
            340                 345                 350

Lys Glu Thr Glu Leu Glu Leu Lys Glu Arg Glu Leu His Glu
        355                 360                 365

Lys Phe Glu His Leu Lys Arg Val His Gln Glu Lys Arg Lys Val
370                 375                 380

Glu Glu Lys Arg Arg Glu Leu Glu Glu Glu Thr Asn Ala Phe Asn Arg
```

```
            385                 390                 395                 400
Arg Lys Ala Ala Val Glu Ala Leu Gln Ser Gln Ala Leu His Ala Thr
                405                 410                 415

Ser Gln Gln Pro Leu Arg Lys Asp Lys Asp Lys Lys Asn Arg Ser Asp
                420                 425                 430

Ile Gly Ala His Gln Pro Gly Met Ser Leu Ser Ser Lys Val Met
                435                 440                 445

Met Thr Lys Ala Ser Val Glu Pro Leu Asn Cys Ser Ser Trp Trp Pro
            450                 455                 460

Ala Ile Gln Cys Cys Ser Cys Leu Val Arg Asp Ala Thr Trp Arg Glu
465                 470                 475                 480

Gly Phe Leu

<210> SEQ ID NO 18
<211> LENGTH: 586
<212> TYPE: PRT
<213> ORGANISM: Homo sapiens

<400> SEQUENCE: 18

Met Lys Lys Ser Tyr Ser Gly Gly Thr Arg Thr Ser Ser Gly Arg Leu
1               5                   10                  15

Arg Arg Leu Gly Asp Ser Ser Gly Pro Ala Leu Lys Arg Ser Phe Glu
                20                  25                  30

Val Glu Glu Val Glu Thr Pro Asn Ser Thr Pro Pro Arg Val Gln
                35                  40                  45

Thr Pro Leu Leu Arg Ala Thr Val Ala Ser Ser Thr Gln Lys Phe Gln
50                  55                  60

Asp Leu Gly Val Lys Asn Ser Glu Pro Ser Ala Arg His Val Asp Ser
65                  70                  75                  80

Leu Ser Gln Arg Ser Pro Lys Ala Ser Leu Arg Arg Val Glu Leu Ser
                85                  90                  95

Gly Pro Lys Ala Ala Glu Pro Val Ser Arg Arg Thr Glu Leu Ser Ile
                100                 105                 110

Asp Ile Ser Ser Lys Gln Val Glu Asn Ala Gly Ala Ile Gly Pro Ser
                115                 120                 125

Arg Phe Gly Leu Lys Arg Ala Glu Val Leu Gly His Lys Thr Pro Glu
                130                 135                 140

Pro Ala Pro Arg Arg Thr Glu Ile Thr Ile Val Lys Pro Gln Glu Ser
145                 150                 155                 160

Ala His Arg Arg Met Glu Pro Pro Ala Ser Lys Val Pro Glu Val Pro
                165                 170                 175

Thr Ala Pro Ala Thr Asp Ala Ala Pro Lys Arg Val Glu Ile Gln Met
                180                 185                 190

Pro Lys Pro Ala Glu Ala Pro Thr Ala Pro Ser Pro Ala Gln Thr Leu
                195                 200                 205

Glu Asn Ser Glu Pro Ala Pro Val Ser Gln Leu Gln Ser Arg Leu Glu
            210                 215                 220

Pro Lys Pro Gln Pro Pro Val Ala Glu Ala Thr Pro Arg Ser Gln Glu
225                 230                 235                 240

Ala Thr Glu Ala Ala Pro Ser Cys Val Gly Asp Met Ala Asp Thr Pro
                245                 250                 255

Arg Asp Ala Gly Leu Lys Gln Ala Pro Ala Ser Arg Asn Glu Lys Ala
                260                 265                 270

Pro Val Asp Phe Gly Tyr Val Gly Ile Asp Ser Ile Leu Glu Gln Met
```

```
                    275                 280                 285
Arg Arg Lys Ala Met Lys Gln Gly Phe Glu Phe Asn Ile Met Val Val
290                 295                 300

Gly Gln Ser Gly Leu Gly Lys Ser Thr Leu Ile Asn Thr Leu Phe Lys
305                 310                 315                 320

Ser Lys Ile Ser Arg Lys Ser Val Gln Pro Thr Ser Glu Glu Arg Ile
                325                 330                 335

Pro Lys Thr Ile Glu Ile Lys Ser Ile Thr His Asp Ile Glu Glu Lys
                340                 345                 350

Gly Val Arg Met Lys Leu Thr Val Ile Asp Thr Pro Gly Phe Gly Asp
                355                 360                 365

His Ile Asn Asn Glu Asn Cys Trp Gln Pro Ile Met Lys Phe Ile Asn
                370                 375                 380

Asp Gln Tyr Glu Lys Tyr Leu Gln Glu Val Asn Ile Asn Arg Lys
385                 390                 395                 400

Lys Arg Ile Pro Asp Thr Arg Val His Cys Cys Leu Tyr Phe Ile Pro
                405                 410                 415

Ala Thr Gly His Ser Leu Arg Pro Leu Asp Ile Glu Phe Met Lys Arg
                420                 425                 430

Leu Ser Lys Val Val Asn Ile Val Pro Val Ile Ala Lys Ala Asp Thr
                435                 440                 445

Leu Thr Leu Glu Glu Arg Val His Phe Lys Gln Arg Ile Thr Ala Asp
                450                 455                 460

Leu Leu Ser Asn Gly Ile Asp Val Tyr Pro Gln Lys Glu Phe Asp Glu
465                 470                 475                 480

Asp Ser Glu Asp Arg Leu Val Asn Glu Lys Phe Arg Glu Met Ile Pro
                485                 490                 495

Phe Ala Val Val Gly Ser Asp His Glu Tyr Gln Val Asn Gly Lys Arg
                500                 505                 510

Ile Leu Gly Arg Lys Thr Lys Trp Gly Thr Ile Glu Val Glu Asn Thr
                515                 520                 525

Thr His Cys Glu Phe Ala Tyr Leu Arg Asp Leu Leu Ile Arg Thr His
                530                 535                 540

Met Gln Asn Ile Lys Asp Ile Thr Ser Ser Ile His Phe Glu Ala Tyr
545                 550                 555                 560

Arg Val Lys Arg Leu Asn Glu Gly Ser Ser Ala Met Ala Asn Gly Met
                565                 570                 575

Glu Glu Lys Glu Pro Glu Ala Pro Glu Met
                580                 585

<210> SEQ ID NO 19
<211> LENGTH: 454
<212> TYPE: PRT
<213> ORGANISM: Homo sapiens

<400> SEQUENCE: 19

Met Ala Ser Ser Glu Val Ala Arg His Leu Leu Phe Gln Ser His Met
1               5                   10                  15

Ala Thr Lys Thr Thr Cys Met Ser Ser Gln Gly Ser Asp Asp Glu Gln
                20                  25                  30

Ile Lys Arg Glu Asn Ile Arg Ser Leu Thr Met Ser Gly His Val Gly
                35                  40                  45

Phe Glu Ser Leu Pro Asp Gln Leu Val Asn Arg Ser Ile Gln Gln Gly
                50                  55                  60
```

```
Phe Cys Phe Asn Ile Leu Cys Val Gly Glu Thr Gly Ile Gly Lys Ser
 65                  70                  75                  80

Thr Leu Ile Asp Thr Leu Phe Asn Thr Asn Phe Glu Asp Tyr Glu Ser
                 85                  90                  95

Ser His Phe Cys Pro Asn Val Lys Leu Lys Ala Gln Thr Tyr Glu Leu
            100                 105                 110

Gln Glu Ser Asn Val Gln Leu Lys Leu Thr Ile Val Asn Thr Val Gly
        115                 120                 125

Phe Gly Asp Gln Ile Asn Lys Glu Glu Ser Tyr Gln Pro Ile Val Asp
    130                 135                 140

Tyr Ile Asp Ala Gln Phe Glu Ala Tyr Leu Gln Glu Leu Lys Ile
145                 150                 155                 160

Lys Arg Ser Leu Phe Thr Tyr His Asp Ser Arg Ile His Val Cys Leu
                165                 170                 175

Tyr Phe Ile Ser Pro Thr Gly His Ser Leu Lys Thr Leu Asp Leu Leu
            180                 185                 190

Thr Met Lys Asn Leu Asp Ser Lys Val Asn Ile Ile Pro Val Ile Ala
        195                 200                 205

Lys Ala Asp Thr Val Ser Lys Thr Glu Leu Gln Lys Phe Lys Ile Lys
    210                 215                 220

Leu Met Ser Glu Leu Val Ser Asn Gly Val Gln Ile Tyr Gln Phe Pro
225                 230                 235                 240

Thr Asp Asp Asp Thr Ile Ala Lys Val Asn Ala Ala Met Asn Gly Gln
                245                 250                 255

Leu Pro Phe Ala Val Val Gly Ser Met Asp Glu Val Lys Val Gly Asn
            260                 265                 270

Lys Met Val Lys Ala Arg Gln Tyr Pro Trp Gly Val Val Gln Val Glu
        275                 280                 285

Asn Glu Asn His Cys Asp Phe Val Lys Leu Arg Glu Met Leu Ile Cys
    290                 295                 300

Thr Asn Met Glu Asp Leu Arg Glu Gln Thr His Thr Arg His Tyr Glu
305                 310                 315                 320

Leu Tyr Arg Arg Cys Lys Leu Glu Glu Met Gly Phe Thr Asp Val Gly
                325                 330                 335

Pro Glu Asn Lys Pro Val Ser Val Gln Glu Thr Tyr Glu Ala Lys Arg
            340                 345                 350

His Glu Phe His Gly Glu Arg Gln Arg Lys Glu Glu Met Lys Gln
        355                 360                 365

Met Phe Val Gln Arg Val Lys Glu Lys Glu Ala Ile Leu Lys Glu Ala
    370                 375                 380

Glu Arg Glu Leu Gln Ala Lys Phe Glu His Leu Lys Arg Leu His Gln
385                 390                 395                 400

Glu Glu Arg Met Lys Leu Glu Glu Lys Arg Arg Leu Leu Glu Glu Glu
                405                 410                 415

Ile Ile Ala Phe Ser Lys Lys Ala Thr Ser Glu Ile Phe His Ser
            420                 425                 430

Gln Ser Phe Leu Ala Thr Gly Ser Asn Leu Arg Lys Asp Lys Asp Arg
        435                 440                 445

Lys Asn Ser Asn Phe Leu
    450

<210> SEQ ID NO 20
<211> LENGTH: 358
<212> TYPE: PRT
```

<213> ORGANISM: Homo sapiens

<400> SEQUENCE: 20

Met Asp Pro Leu Arg Ser Pro Ser Pro Cys Leu Ser Ser Gln Pro
1               5                   10                  15

Ser Ser Pro Ser Thr Pro Pro Cys Glu Met Leu Gly Pro Val Gly Ile
            20                  25                  30

Glu Ala Val Leu Asp Gln Leu Lys Ile Lys Ala Met Lys Met Gly Phe
                35                  40                  45

Glu Phe Asn Ile Met Val Val Gly Gln Ser Gly Leu Gly Lys Ser Thr
    50                  55                  60

Met Val Asn Thr Leu Phe Lys Ser Lys Val Trp Lys Ser Asn Pro Pro
65                  70                  75                  80

Gly Leu Gly Val Pro Thr Pro Gln Thr Leu Gln Leu His Ser Leu Thr
                85                  90                  95

His Val Ile Glu Glu Lys Gly Val Lys Leu Lys Leu Thr Val Thr Asp
                100                 105                 110

Thr Pro Gly Phe Gly Asp Gln Ile Asn Asn Asp Asn Cys Trp Asp Pro
            115                 120                 125

Ile Leu Gly Tyr Ile Asn Glu Gln Tyr Glu Gln Tyr Leu Gln Glu Glu
    130                 135                 140

Ile Leu Ile Thr Arg Gln Arg His Ile Pro Asp Thr Arg Val His Cys
145                 150                 155                 160

Cys Val Tyr Phe Val Pro Pro Thr Gly His Cys Leu Arg Pro Leu Asp
                165                 170                 175

Ile Glu Phe Leu Gln Arg Leu Cys Arg Thr Val Asn Val Pro Val
            180                 185                 190

Ile Ala Arg Ala Asp Ser Leu Thr Met Glu Glu Arg Glu Ala Phe Arg
    195                 200                 205

Arg Arg Ile Gln Gln Asn Leu Arg Thr His Cys Ile Asp Val Tyr Pro
210                 215                 220

Gln Met Cys Phe Asp Glu Asp Ile Asn Asp Lys Ile Leu Asn Ser Lys
225                 230                 235                 240

Leu Arg Asp Arg Ile Pro Phe Ala Val Val Gly Ala Asp Gln Glu His
                245                 250                 255

Leu Val Asn Gly Arg Cys Val Leu Gly Arg Lys Thr Lys Trp Gly Ile
            260                 265                 270

Ile Glu Val Glu Asn Met Ala His Cys Glu Phe Pro Leu Leu Arg Asp
    275                 280                 285

Leu Leu Ile Arg Ser His Leu Gln Asp Leu Lys Asp Ile Thr His Asn
290                 295                 300

Ile His Tyr Glu Asn Tyr Arg Val Ile Arg Leu Asn Glu Ser His Leu
305                 310                 315                 320

Leu Pro Arg Gly Pro Gly Trp Val Asn Leu Ala Pro Ala Ser Pro Gly
                325                 330                 335

Gln Leu Thr Thr Pro Arg Thr Phe Lys Val Cys Arg Gly Ala His Asp
            340                 345                 350

Asp Ser Asp Asp Glu Phe
        355

<210> SEQ ID NO 21
<211> LENGTH: 432
<212> TYPE: PRT
<213> ORGANISM: Homo sapiens

```
<400> SEQUENCE: 21

Met Ala Glu Arg Thr Met Ala Met Pro Thr Gln Ile Pro Ala Asp Gly
1               5                   10                  15

Asp Thr Gln Lys Glu Asn Asn Ile Arg Cys Leu Thr Thr Ile Gly His
            20                  25                  30

Phe Gly Phe Glu Cys Leu Pro Asn Gln Leu Val Ser Arg Ser Ile Arg
        35                  40                  45

Gln Gly Phe Thr Phe Asn Ile Leu Cys Val Gly Glu Thr Gly Ile Gly
    50                  55                  60

Lys Ser Thr Leu Ile Asp Thr Leu Phe Asn Thr Asn Leu Lys Asp Asn
65                  70                  75                  80

Lys Ser Ser His Phe Tyr Ser Asn Val Gly Leu Gln Ile Gln Thr Tyr
                85                  90                  95

Glu Leu Gln Glu Ser Asn Val Gln Leu Lys Leu Thr Val Val Glu Thr
            100                 105                 110

Val Gly Tyr Gly Asp Gln Ile Asp Lys Glu Ala Ser Tyr Gln Pro Ile
        115                 120                 125

Val Asp Tyr Ile Asp Ala Gln Phe Glu Ala Tyr Leu Gln Glu Glu Leu
    130                 135                 140

Lys Ile Lys Arg Ser Leu Phe Glu Tyr His Asp Ser Arg Val His Val
145                 150                 155                 160

Cys Leu Tyr Phe Ile Ser Pro Thr Gly His Ser Leu Lys Ser Leu Asp
                165                 170                 175

Leu Leu Thr Met Lys Asn Leu Asp Ser Lys Val Asn Ile Ile Pro Leu
            180                 185                 190

Ile Ala Lys Ala Asp Thr Ile Ser Lys Asn Asp Leu Gln Thr Phe Lys
    195                 200                 205

Asn Lys Ile Met Ser Glu Leu Ile Ser Asn Gly Ile Gln Ile Tyr Gln
            210                 215                 220

Leu Pro Thr Asp Glu Glu Thr Ala Ala Gln Ala Asn Ser Ser Val Ser
225                 230                 235                 240

Gly Leu Leu Pro Phe Ala Val Val Gly Ser Thr Asp Glu Val Lys Val
                245                 250                 255

Gly Lys Arg Met Val Arg Gly Arg His Tyr Pro Trp Gly Val Leu Gln
            260                 265                 270

Val Glu Asn Glu Asn His Cys Asp Phe Val Lys Leu Arg Asp Met Leu
    275                 280                 285

Leu Cys Thr Asn Met Glu Asn Leu Lys Glu Lys Thr His Thr Gln His
    290                 295                 300

Tyr Glu Cys Tyr Arg Tyr Gln Lys Leu Gln Lys Met Gly Phe Thr Asp
305                 310                 315                 320

Val Gly Pro Asn Asn Gln Pro Val Ser Phe Gln Glu Ile Phe Glu Ala
                325                 330                 335

Lys Arg Gln Glu Phe Tyr Asp Gln Cys Gln Arg Glu Glu Glu Glu Leu
            340                 345                 350

Lys Gln Arg Phe Met Gln Arg Val Lys Glu Lys Glu Ala Thr Phe Lys
    355                 360                 365

Glu Ala Glu Lys Glu Leu Gln Asp Lys Phe Glu His Leu Lys Met Ile
    370                 375                 380

Gln Gln Glu Glu Ile Arg Lys Leu Glu Glu Lys Lys Gln Leu Glu
385                 390                 395                 400

Gly Glu Ile Ile Asp Phe Tyr Lys Met Lys Ala Ala Ser Glu Ala Leu
                405                 410                 415
```

```
Gln Thr Gln Leu Ser Thr Asp Thr Lys Lys Asp Lys His Arg Lys Lys
            420                 425                 430

<210> SEQ ID NO 22
<211> LENGTH: 51
<212> TYPE: PRT
<213> ORGANISM: Artificial Sequence
<220> FEATURE:
<223> OTHER INFORMATION: human Septin-7, aa 1-51

<400> SEQUENCE: 22

Met Ser Val Ser Ala Arg Ser Ala Ala Ala Glu Glu Arg Ser Val Asn
1               5                   10                  15

Ser Ser Thr Met Val Ala Gln Gln Lys Asn Leu Glu Gly Tyr Val Gly
            20                  25                  30

Phe Ala Asn Leu Pro Asn Gln Val Tyr Arg Lys Ser Val Lys Arg Gly
        35                  40                  45

Phe Glu Phe
    50

<210> SEQ ID NO 23
<211> LENGTH: 104
<212> TYPE: PRT
<213> ORGANISM: Artificial Sequence
<220> FEATURE:
<223> OTHER INFORMATION: human Septin-7, aa 334-437

<400> SEQUENCE: 23

Ser Pro Leu Ala Gln Met Glu Glu Arg Arg Glu His Val Ala Lys
1               5                   10                  15

Met Lys Lys Met Glu Met Glu Met Glu Gln Val Phe Glu Met Lys Val
            20                  25                  30

Lys Glu Lys Val Gln Lys Leu Lys Asp Ser Glu Ala Glu Leu Gln Arg
        35                  40                  45

Arg His Glu Gln Met Lys Lys Asn Leu Glu Ala Gln His Lys Glu Leu
    50                  55                  60

Glu Glu Lys Arg Arg Gln Phe Glu Asp Glu Lys Ala Asn Trp Glu Ala
65                  70                  75                  80

Gln Gln Arg Ile Leu Glu Gln Gln Asn Ser Ser Arg Thr Leu Glu Lys
                85                  90                  95

Asn Lys Lys Lys Gly Lys Ile Phe
                100
```

AUTOANTIBODIES TO SEPTIN-7 AND DIAGNOSIS OF NEUROLOGICAL DISEASE

CROSS-REFERENCE TO RELATED APPLICATION

This application claims the benefit of European Application No. 19217147.8, filed on Dec. 17, 2019, the content of which is hereby incorporated by reference in its entirety.

REFERENCE TO A SEQUENCE LISTING

The present application is accompanied by an ASCII text file as a computer-readable form containing the sequence listing entitled, "2020-11-18_SL_ST25.txt", created on Nov. 18, 2020, with the file size of 84,999 bytes, the content of which is hereby incorporated by reference in its entirety.

BACKGROUND OF THE INVENTION

Field of the Invention

The present invention relates to a method for diagnosing a disease comprising the step detecting in a sample from a patient an autoantibody binding to Septin-7, a use of a polypeptide comprising Septin-7 or a variant thereof for the diagnosis of a disease, preferably comprising the step detecting in a sample an autoantibody binding to Septin-7, a kit for the diagnosis of a disease, which kit comprises a polypeptide comprising Septin-7 or a variant thereof or a medical device comprising a polypeptide comprising Septin-7 or a variant thereof and an autoantibody to Septin-7.

Discussion of the Background

Developing diagnostic systems for neurological diseases is a continuing challenge in biomedical science, not in the least because many symptoms encountered may be accounted for by a huge variety of causes including genetically-inherited diseases, drug abuse, malnutrition, infection, injury, psychiatric illness, immunological defects and cancer.

Since a neurological disease is rarely associated with a unique characteristic pattern of clinical symptoms, it is often difficult to provide a reliable diagnosis solely based on the observation and examination of the patients affected or their medical history.

The importance of an early diagnosis cannot be overemphasized. Many neurological disorders, most prominently Alzheimer's and Parkinson's diseases as well as Multiple Sclerosis, cannot be cured, but drugs are available that may be used to slow down their progression. In addition, certain rare types of cancer are associated with neurological symptoms. The earlier the diagnosis, the better the chances to exploit the spectrum of available therapies to the full benefit of the patient.

This holds all the more true in the case of neurological diseases associated with autoantibodies. In some cases, the link between a specific detectable autoantibody and a condition is sufficiently strong to allow for an immediate diagnosis.

But even if it is not, the detection of autoantibodies may point the physician in charge to therapeutic means that may be used to ameliorate the patient's condition. There is a variety of widely used immunosuppressants that may be used regardless of the nature of the autoantibody's target. Alternatively, apheresis may be used to remove autoantibodies from the patient's blood. In many cases, patients went on to lead a normal life following early diagnosis and treatment of a neurological autoimmune disease.

Diagnostic assays based on the detection of autoantibodies may also corroborate the diagnosis of diseases other than those associated with autoantibodies. If it turns out that a blood sample is devoid of specific autoantibodies, this is likely to help the physician in charge exclude a range of possibilities and thus narrow down the spectrum of plausible conditions.

Examples of neurological conditions coinciding with the emergence of autoantibodies include Neuromyelitis optica, a disease characterized by loss of visual perception and spinal cord function, and anti-NMDA receptor encephalitis, which is associated with autonomic dysfunction, hypoventilation, cerebellar ataxia, hemiparesis, loss of consciousness, or catatonia. Whilst the involvement of autoantibodies and the nature of these conditions as such was previously poorly understood, many of this disease can now be diagnosed and treated efficiently owing to the availability of assays based on the detection of autoantibodies.

Another example is neuropathy, a neurological disease with symptoms that might include lack of coordination, muscle weakness and paralysis. Neuropathy can be an autoimmune disease, but can also have many other non-autoimmune causes including diabetes, infections, kidney disease, liver disease and hypothyroidism.

Another example is encephalopathy, characterized by symptoms such as impairment of cognition, attention and consciousness, cognitive defects, headache, seizures, dysarthria, gait impairment and tremor. It can be an autoimmune disease, but can also have many other non-autoimmune causes including metabolic disorders, genetically inherited diseases, infection, toxicity caused by chemicals and sepsis. Autoimmune encephalopathy may be associated with an autoantibody to the NMDA receptor or with Hashimoto's syndrome which may be associated with an autoantibody to alpha enolase.

Therefore, it is paramount that new approaches be developed to diagnose and distinguish neurological conditions associated with autoantibodies from those that are not.

In addition, there is the need to devise new methods for detecting tumors or identifying patients at risk for having a tumor.

SUMMARY OF THE INVENTION

The present application includes the following embodiments:
1. A method for diagnosing a disease, comprising the step detecting in a sample from a patient an autoantibody binding to Septin-7.
2. A use of a polypeptide comprising Septin-7 or a variant thereof for the diagnosis of a disease, preferably comprising the step detecting in a sample an autoantibody binding to Septin-7.
3. A polypeptide comprising Septin-7 or a variant thereof for use in a treatment of a disease.
4. An autoantibody to Septin-7, preferably an isolated autoantibody to Septin-7.
5. A use of the autoantibody according to embodiment 4 for the diagnosis of a disease.
6. A method for isolating an autoantibody binding to Septin-7, comprising the steps
   a) contacting a sample comprising the autoantibody with a polypeptide comprising Septin-7 or a variant thereof under conditions compatible with formation of a complex, wherein said autoantibody binds to said polypeptide,
b) isolating the complex formed in step a),
c1) detecting the complex formed in step a) or c2) dissociating the complex isolated in step b) and separating the autoantibody from the polypeptide.
7. A pharmaceutical composition comprising a polypeptide comprising Septin-7 or a variant thereof.
8. A kit for the diagnosis of a disease, which kit comprises a polypeptide comprising Septin-7 or a variant thereof or a medical device comprising a polypeptide comprising Septin-7 or a variant thereof,
   wherein preferably the kit comprises in addition a means for detecting a complex comprising the polypeptide and an antibody binding to Septin-7, preferably an autoantibody binding to Septin-7,
   wherein preferably the kit further comprises a positive control comprising an anti-Septin-7 antibody or a variant thereof.
9. A use of a polypeptide comprising Septin-7 or a variant thereof or an autoantibody binding to Septin-7 or a medical device comprising a polypeptide comprising Septin-7 or a variant thereof for the manufacture of a kit or medical device, preferably diagnostic device, for the diagnosis of a disease.
10. The method, polypeptide, use, autoantibody, pharmaceutical composition, medical device or kit according to any of embodiments 1 to 6 and 8 to 9,
    wherein the disease is a neurological disease, preferably of the central nervous system, more preferably an autoimmune disease, more preferably selected from the group comprising PNS, neuropathy, encephalopathy, encephalitis, encephalomyelopathy, myelopathy, episodic ataxia, bilateral carpal tunnel syndrome and lumbosacral polyradiculopathy
    or wherein the disease is a tumor, preferably from the group comprising ovarian cancer, breast adenocarcinoma, non-Hodgkin lymphoma, carcinoid, myelodysplastic syndrome and carcinoid of the lung.
11. The method or use according to any of embodiments 1, 3, 7 and 10, wherein the sample is a bodily fluid comprising antibodies, preferably selected from the group comprising whole blood, plasma, serum, cerebrospinal fluid and saliva.
12. The method, use or kit according to any of embodiments 1, 2, 5, or 8 to 11, wherein the autoantibody or complex is detected using a technique selected from the group comprising immunodiffusion techniques, immunoelectrophoretic techniques, light scattering immunoassays, agglutination techniques, labeled immunoassays such as those from the group comprising radiolabeled immunoassay, enzyme immunoassays, more preferably ELISA, chemiluminescence immunoassays, preferably electrochemiluminescence immunoassay, and immunofluorescence, preferably indirect immunofluorescence.
13. The kit according to any of embodiments 8, 10 or 12, wherein the medical device is selected from the group comprising a glass slide, preferably for microscopy, a biochip, a microtiter plate, a lateral flow device, a test strip, a membrane, preferably a line blot, a chromatography column and a bead, preferably a magnetic or fluorescent bead.
14. The method, use, polypeptide, autoantibody, medical device, pharmaceutical composition or kit according to any of embodiments 1 to 13, wherein Septin-7 or a variant thereof is part of a Septin complex comprising, in addition to Septin-7, additional Septins required to assemble the Septin complex, preferably all from the group comprising Septin-3, Septin-5, Septin-6, and Septin-11 or a variant thereof.

BRIEF DESCRIPTION OF THE DRAWINGS

FIG. 5A shows a table of a first set the patients of the second cohort including the clinical and testing characteristics, treatment, and outcomes data.

FIG. 5B is a continuation of FIG. 5A showing a table of a second set of the patients of the second cohort including the clinical and testing characteristics, treatment, and outcomes data.

FIG. 5C is a continuation of FIGS. 5A and 5B showing a table of a third set of the patients of the second cohort including the clinical and testing characteristics, treatment, and outcomes data.

DETAILED DESCRIPTION OF THE INVENTION

Figure 1:
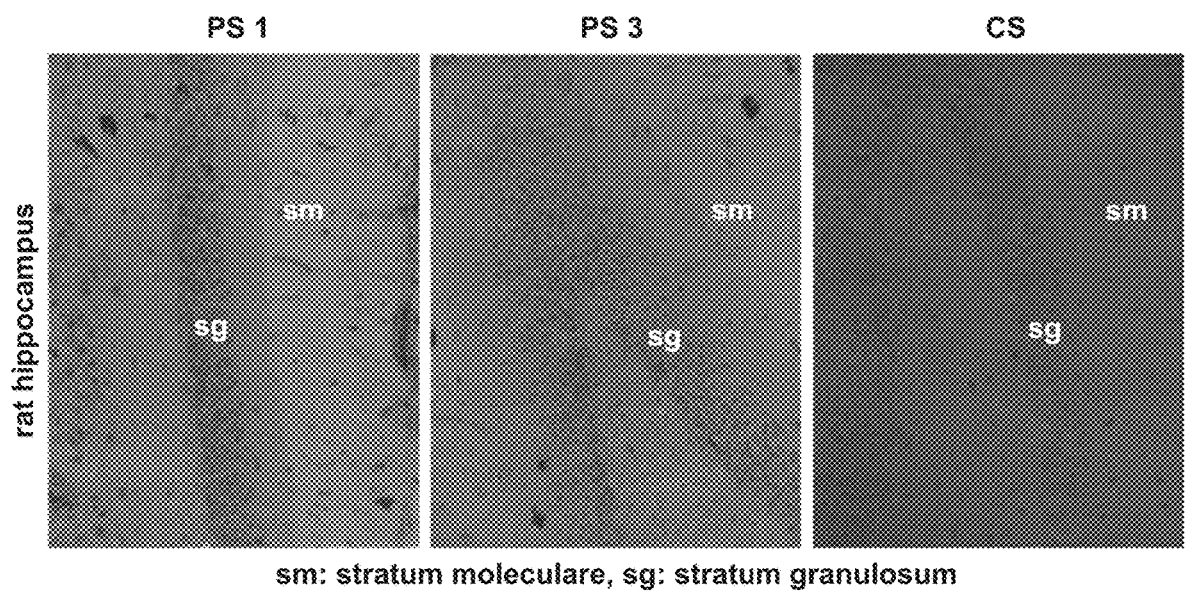
FIG. 1 shows the results of indirect immunofluorescence assays of sera from two representative positive patients' sera comprising an autoantibody to Septin-7 (PS1 and PS3) or a healthy control serum (CS) (all 1:100) using permeabilized cryosections of rat hippocampus. Both patient sera, but not the control serum, show a granular staining of the outer layer of the stratum moleculare (sm) FIG. 1.

The present Invention relates to autoantibodies to Septin-7 and diagnostic assays based on their detection and reagents for such assays. As far as the inventors are aware, the existence of autoantibodies to Septin-7, let alone the diagnostic usefulness of them and reagents, methods and uses for detecting them, has not yet been reported in the state of the art.

WO2019/226616 discloses Septin-5-specific autoantibodies and the detection of them for the purpose of assessing autoimmune ataxias.

The problem underlying the present invention is to provide novel reagents, devices and methods that may be used to support the diagnosis and treatment of an autoimmune disease, more preferably selected from the group comprising paraneoplastic neurological syndrome PNS, neuropathy, encephalopathy, encephalitis, encephalomyelopathy, myelopathy, episodic ataxia, bilateral carpal tunnel syndrome and lumbosacral polyradiculopathy.

Another problem underlying the present invention is to provide novel reagents, devices and methods that may be used to distinguish autoimmune diseases, in particular neurological autoimmune diseases, more preferably selected from the group comprising peripheral neuropathy, encephalopathy, encephalitis, encephalomyelopathy, myelopathy, episodic ataxia, bilateral carpal tunnel syndrome and lumbosacral polyradiculopathy, from diseases other than autoimmune diseases, for example from infections associated with neurological symptoms, not in the least to determine the most promising treatment regimen, more specifically whether or not an immunosuppressive treatment is adequate.

The problem underlying the present invention is solved by the subject-matter of the attached independent and dependent claims.

In a 1$^{st}$ aspect, the problem underlying the present invention is solved by a method for diagnosing a disease comprising the step detecting in a sample from a patient an autoantibody binding to Septin-7.

In a 2$^{nd}$ aspect, the problem underlying the present invention is solved by use of a polypeptide comprising Septin-7 or a variant thereof for the diagnosis of a disease, preferably comprising the step detecting in a sample an autoantibody binding to Septin-7.

In a 3$^{rd}$ aspect, the problem underlying the present invention is solved by polypeptide comprising Septin-7 or a variant thereof for use in a treatment of a disease.

In a 4$^{th}$ aspect, the problem underlying the present invention is solved by an autoantibody to Septin-7, preferably an isolated autoantibody to Septin-7.

In a 5$^{th}$ aspect, the problem underlying the present invention is solved by use of the autoantibody according to Septin-7 for the diagnosis of a disease.

In a 6$^{th}$ aspect, the problem underlying the present invention is solved by a method for isolating an autoantibody binding to Septin-7, comprising the steps
a) contacting a sample comprising the autoantibody with a polypeptide comprising Septin-7 or a variant thereof under conditions compatible with formation of a complex, wherein said autoantibody binds to said polypeptide,
b) isolating the complex formed in step a),
c1) detecting the complex formed in step a) or c2) dissociating the complex isolated in step b) and separating the autoantibody from the polypeptide.

In a 7$^{th}$ aspect, the problem underlying the present invention is solved by pharmaceutical composition comprising a polypeptide comprising Septin-7 or a variant thereof.

In an 8$^{th}$ aspect, the problem underlying the present invention is solved by kit for the diagnosis of a disease, which kit comprises a polypeptide comprising Septin-7 or a variant thereof or a medical device comprising a polypeptide comprising Septin-7 or a variant thereof,
wherein preferably the kit comprises in addition a means for detecting a complex comprising the polypeptide and an antibody binding to Septin-7, preferably an autoantibody binding to Septin-7,
wherein preferably the kit further comprises a positive control comprising an anti-Septin-7 antibody or a variant thereof.

In a 9$^{th}$ aspect, the problem underlying the present invention is solved by a use of a polypeptide comprising Septin-7 or a variant thereof or an autoantibody binding to Septin-7 or a medical device comprising a polypeptide comprising Septin-7 or a variant thereof for the manufacture of a kit or medical device, preferably diagnostic device, for the diagnosis of a disease.

In a preferred embodiment, the disease is a neurological disease, preferably of the central nervous system, more preferably an autoimmune disease, more preferably selected from the group comprising PNS, neuropathy, preferably peripheral neuropathy, encephalopathy, encephalitis, encephalomyelopathy, myelopathy, episodic ataxia, bilateral carpal tunnel syndrome and lumbosacral polyradiculopathy. In a preferred embodiment, the disease is a neurological disease associated with the presence of an autoantibody, preferably an autoantibody to Septin-7.

In another preferred embodiment, the disease is a tumor, preferably from the group comprising ovarian cancer, breast adenocarcinoma, non-Hodgkin lymphoma, carcinoid, myelodysplastic syndrome and carcinoid of the lung. In a preferred embodiment, the tumor is a tumor associated with the presence of an autoantibody, more preferably an autoantibody to Septin-7. In a preferred embodiment, the tumor associated with the presence of an autoantibody is selected from the group comprising ovarian cancer, breast adenocarcinoma, non-Hodgkin lymphoma, carcinoid, myelodysplastic syndrome, and carcinoid of the lung.

In a preferred embodiment, the sample is a bodily fluid comprising antibodies, preferably selected from the group comprising whole blood, plasma, serum, cerebrospinal fluid and saliva.

In a preferred embodiment, the autoantibody or complex is detected using a technique selected from the group comprising immunodiffusion techniques, immunoelectrophoretic techniques, light scattering immunoassays, agglutination techniques, labeled immunoassays such as those from the group comprising radiolabeled immunoassay, enzyme immunoassays, more preferably ELISA, chemiluminescence immunoassays, preferably electrochemiluminescence immunoassay, and immunofluorescence, preferably indirect immunofluorescence.

In a preferred embodiment, the medical device is selected from the group comprising a glass slide, preferably for microscopy, a biochip, a microtiter plate, a lateral flow device, a test strip, a membrane, preferably a line blot, a chromatography column and a bead, preferably a magnetic or fluorescent bead.

In a preferred embodiment, Septin-7 or a variant thereof is part of a Septin complex comprising, in addition to Septin-7, additional Septins required to assemble the Septin complex, preferably all from the group comprising Septin-3, Septin-5, Septin-6, and Septin-11 or a variant thereof.

In a preferred embodiment, the sample is a bodily fluid comprising antibodies, preferably selected from the group comprising whole blood, plasma, serum, cerebrospinal fluid and saliva.

The present invention is based on the inventors' surprising finding that an autoantibody to Septin-7 exists and may be detected in samples from a number of patients suffering from neurological conditions and tumors, but not in samples obtained from healthy subjects.

Furthermore, the present invention is based on the inventors' surprising finding that the novel neurological disease may be diagnosed by way of detection of an autoantibody to Septin-7.

Without wishing to be bound to any theory, the presence of such autoantibodies suggests that the function of Septin-7 and/or downstream effectors is impaired in patients having such autoantibodies to the effect that neurological symptoms occur.

In a preferred embodiment, the term "Septin complex" as used herein, refers to a complex comprising Septin subunits. In humans, septins are involved in cytokinesis, cilium formation and neurogenesis. There are 13 different human septin proteins, which are grouped into four subfamilies: (1) Septin-1, Septin-2, Septin-4, Septin-5; (2) Septin-3, Septin-9, Septin-12; (3) Septin-6; Septin-8, Septin-10, Septin-11, Septin-14; and (4) Septin-7. Septins may form a Septin complex which is either a hetero-hexamer, which comprises monomers selected from three different groups and the monomer from each group is present in two copies or are hetero-octamers, wherein monomers from four different groups are present and each monomer is present in two copies. Alternatively, two different monomers, preferably Septin-6 and Septin-11 may be taken from group (3).

In a more preferred embodiment, the complex comprises two monomers each of Septin-3, Septin-5, Septin-7 and one monomer each from Septin-6 and Septin-11. Septin complexes assemble spontaneously when suitable Septin subunits are present, for example in a cell or in vitro.

The present invention relates to a polypeptide comprising a mammalian, preferably human polypeptide selected from Septin-7 or antigenic variants reactive to autoantibodies binding to Septin-7. Mammalian Septin-7 includes homologues from human, monkey, mouse, rat, rabbit, guinea pig or pig, preferably human.

In a preferred embodiment, Septin-7 is the polypeptide encoded by SEQ ID NO: 1. In a preferred embodiment, Septin-3 is the polypeptide encoded by SEQ ID NO: 4. In a preferred embodiment, Septin-5 is the polypeptide encoded by SEQ ID NO: 5. In a preferred embodiment, Septin-6 is the polypeptide encoded by SEQ ID NO: 6. In a preferred embodiment, Septin-11 is the polypeptide encoded by SEQ ID NO: 7. Throughout this application, any data base codes cited refers to the Uniprot data base, more specifically the version on the filing date of this application or its earliest priority application.

The teachings of the present invention may not only be carried out using polypeptides, in particular a polypeptide comprising the native sequence of a polypeptide such as Septin-7 or nucleic acids having the exact sequences referred to in this application explicitly, for example by function, name, sequence or accession number, or implicitly, but also using variants of such polypeptides or nucleic acids.

In a preferred embodiment, the term "variant", as used herein, may refer to at least one fragment of the full-length sequence referred to, more specifically one or more amino acid or nucleic acid sequence which is, relative to the full-length sequence, truncated at one or both termini by one or more amino acids. Such a fragment comprises or encodes for a peptide having at least 6, 7, 8, 10, 12, 15, 20, 25, 50, 75, 100, 150, 200, 300, 400 successive amino acids of the original sequence or a variant thereof. The total length of the variant may be at least 6, 7, 8, 9, 10, 11, 12, 20, 25, 30, 40, 50, 60, 70, 80, 90, 100, 200, 300, 350, 400, or more amino acids.

The term "variant" relates not only to at least one fragment, but also to a polypeptide or a fragment thereof comprising amino acid sequences that are at least 40, 50, 60, 70, 75, 80, 85, 90, 92, 94, 95, 96, 97, 98 or 99% identical to the reference amino acid sequence referred to or the fragment thereof, wherein amino acids other than those essential for the biological activity, for example the ability of an antigen to bind to an (auto)antibody, or the fold or structure of the polypeptide are deleted or substituted and/or one or more such essential amino acids are replaced in a conservative manner and/or amino acids are added such that the biological activity of the polypeptide is preserved. The state of the art comprises various methods that may be used to align two given nucleic acid or amino acid sequences and to calculate the degree of identity, see for example Arthur Lesk (2008), Introduction to bioinformatics, Oxford University Press, 2008, $3^d$ edition. In a preferred embodiment, the Clustal W software (Larkin, M. A., Blackshields, G., Brown, N. P., Chenna, R., McGettigan, P. A., McWlliam, H., Valentin, F., Wallace, I. M., Wilm, A., Lopez, R., Thompson, J. D., Gibson, T. J., Higgins, D. G. (2007). Clustal W and Clustal X version 2.0. Bioinformatics, 23, 2947-2948) is used using default settings.

In more preferred embodiments of the invention, the term "variant" of Septin-7 refers to a peptide comprising SEQ ID NO: 22 and/or SEQ ID NO: 23 and having not more than 420, not more than 400, not more than 350, not more than 300, not more than 250, not more than 200, not more than 150, not more than 130 or not more than 110 amino acids. In even more preferred embodiments, the variant consists of SEQ ID NO: 22 or SEQ ID NO: 23.

In a preferred embodiment, the variant is a linear, non-folded polypeptide, which is optionally denatured.

In a preferred embodiment, the polypeptide and variants thereof may, in addition, comprise chemical modifications, for example isotopic labels or covalent modifications such as glycosylation, phosphorylation, acetylation, decarboxylation, citrullination, methylation, hydroxylation and the like. The person skilled in the art is familiar with methods to modify polypeptides. Any modification is designed such that it does not abolish the biological activity of the variant.

Moreover, variants may also be generated by fusion with other known polypeptides or variants thereof and comprise active portions or domains, preferably having a sequence identity of at least 70, 75, 80, 85, 90, 92, 94, 95, 96, 97, 98 or 99% when aligned with the active portion of the reference sequence, wherein the term "active portion", as used herein, refers to an amino acid sequence, which is less than the full length amino acid sequence or, in the case of a nucleic acid sequence, codes for less than the full length amino acid sequence, respectively, and/or is a variant of the natural sequence, but retains at least some of the biological activity.

In a preferred embodiment, the term "variant" of a nucleic acid comprises nucleic acids the complementary strand of which hybridizes, preferably under stringent conditions, to the reference or wild type nucleic acid. Stringency of hybridization reactions is readily determinable by one of ordinary skilled in the art, and in general is an empirical calculation dependent on probe length, washing temperature and salt concentration. In general longer probes require higher temperatures for proper annealing, while shorter probes less so. Hybridization generally depends on the ability of denatured DNA to reanneal to complementary strands present in an environment below their melting temperature: The higher the degree of desired homology between the probe and hybridizable sequence, the higher the relative temperature which may be used. As a result, higher relative temperatures would tend to make the reaction conditions more stringent, while lower temperature less so. For additional details and explanation of stringency of hybridization reactions, see Ausubel, F. M. (1995), Current Protocols in Molecular Biology. John Wiley & Sons, Inc. Moreover, the person skilled in the art may follow the instructions given in the manual Boehringer Mannheim GmbH (1993) The DIG System Users Guide for Filter Hybridization, Boehringer Mannheim GmbH, Mannheim, Germany and in Liebl, W., Ehrmann, M., Ludwig, W., and Schleifer, K. H. (1991) International Journal of Systematic Bacteriology 41: 255-260 on how to identify DNA sequences by means of hybridization. In a preferred embodiment, stringent conditions are applied for any hybridization, i.e. hybridization occurs only if the probe is 70% or more identical to the target sequence. Probes having a lower degree of identity with respect to the target sequence may hybridize, but such hybrids are unstable and will be removed in a washing step under stringent conditions, for example lowering the concentration of salt to 2×SSC or, optionally and subsequently, to 0.5×SSC, while the temperature is, in order of increasing preference, approximately 50° C.-68° C., approximately 52° C.-68° C., approximately 54° C.-68° C., approximately 56° C.-68° C., approximately 58° C.-68° C., approximately 60° C.-68° C., approximately 62° C.-68° C., approximately 64° C.-68° C., approximately 66° C.-68° C. In a particularly preferred embodiment, the temperature is approximately 64° C.-68° C. or approximately 66° C.-68° C. It is possible to adjust the concentration of salt to 0.2×SSC or even 0.1×SSC. Nucleic acid sequences having a degree of identity with respect to the reference or wild type sequence of at least 70, 80, 90, 91, 92, 93, 94, 95, 96, 97, 98, 99% may be isolated. In a preferred embodiment, the term variant of a nucleic acid sequence, as used herein, refers to any nucleic acid sequence that encodes the same amino acid sequence and variants thereof as the reference nucleic acid sequence, in line with the degeneracy of the genetic code.

The variant of the polypeptide has biological activity. In a preferred embodiment, such biological activity is the ability to bind specifically to an autoantibody binding to Septin-7, as found in a patient suffering from an autoimmune disease or tumor associated with and autoantibody to Septin-7. For example, whether or not a variant of Septin-7 has such biological activity may be checked by determining whether or not the variant of interest binds to an autoantibody from a sample of a patient which autoantibody binds to wild type Septin-7, preferably as determined by indirect immunofluorescence using cerebellum, hippocampus or a eukaryotic cell overexpressing Septin-7, preferably as part of a Septin complex, preferably with one or more, more preferably all from the group comprising Septin-3, Septin-5, Septin-6, and Septin-11 or a variant thereof as described in the experimental section of this application.

Any polypeptide according to the present invention, when used to carry out the teachings of the present invention, may be provided in any form and at any degree of purification, from liquid samples, tissues or cells comprising said polypeptide in an endogenous form, more preferably cells overexpressing the polypeptide, crude or enriched lysates of such cells, to purified and/or isolated polypeptide which is optionally essentially pure. In a preferred embodiment, the polypeptide is a native polypeptide, wherein the term "native polypeptide", as used herein, refers to a folded polypeptide, more preferably to a folded polypeptide purified from tissues or cells, more preferably from mammalian cells or tissues, optionally from non-recombinant tissues or cells. In another preferred embodiment, the polypeptide is a recombinant protein, wherein the term "recombinant", as used herein, refers to a polypeptide produced using genetic engineering approaches at any stage of the production process, for example by fusing a nucleic acid encoding the polypeptide to a strong promoter for overexpression in cells or tissues or by engineering the sequence of the polypeptide itself. The person skilled in the art is familiar with methods for engineering nucleic acids and polypeptides encoded (for example, described in Sambrook, J., Fritsch, E. F. and Maniatis, T. (1989), Molecular Cloning, CSH or in Brown T. A. (1986), Gene Cloning—an introduction, Chapman & Hall) and for producing and purifying native or recombinant polypeptides (for example Handbooks "Strategies for Protein Purification", "Antibody Purification", "Purifying Challenging Proteins" (2009/2010), published by GE Healthcare Life Sciences, and in Burgess, R. R., Deutscher, M. P. (2009), Guide to Protein Purification). In a preferred embodiment, a polypeptide is pure if at least 60, 70, 80, 90, 95 or 99 percent of the polypeptide in the respective sample consists of said polypeptide as judged by SDS polyacrylamide gel electrophoresis followed by Coomassie blue staining and visual inspection. Preferably the polypeptide is Septin-7 or a variant thereof.

If the inventive polypeptide is provided in the form of tissue, it is preferred that the tissue is mammalian tissue, for example human, rat, primate, donkey, mouse, goat, horse, sheep, pig or cow, more preferably brain tissue, most preferably cerebellum. If a cell lysate is used, it is preferred that the cell lysate comprises the membranes associated with the surface of the cell or is in fact a fraction enriched in membranes. If said polypeptide is provided in the form of a recombinant cell, it is preferred that the recombinant cell is a eukaryotic cell such as a yeast cell, more preferably a cell from a multicellular eukaryote such as a plant, mammal, frog or insect, most preferably from a mammal, for example rat, human, primate, donkey, mouse, goat, horse, sheep, pig or cow.

The polypeptide used to carry out the inventive teachings, including any variants, is preferably designed such that it comprises at least one epitope recognized by and/or binds specifically to the autoantibody binding to Septin-7. Any epitope is more preferably an epitope recognized by such an autoantibody only, by contrast to antibodies other than an autoantibody to Septin-7. In one embodiment, such polypeptide comprises a stretch of 6, 7, 8, 9, 10, 11, 12, 20, 25, 30, 40, 50, 60, 70, 80, 90, 100 or more, preferably at least 9 but no more than 16, consecutive amino acids from Septin-7. The person skilled in the art is familiar with guidelines used to design peptides having sufficient immunogenicity, for example those described in Jackson, D. C., Fitzmaurice, C. J., Brown, L. E., Zeng, W. (1999), Preparation and properties of totally synthetic immunogens, Vaccine Volume 18, Issues 3-4, September 1999, Pages 355-361; and Black, M., Trent, A., Tirrell, M. and Olive, C. (2010), Advances in the design and delivery of peptide subunit vaccines with a focus on Toll-like receptor agonists, Expert Rev Vaccines, 2010 February; 9(2): 157-173.

Briefly, it is desirable that the peptide meets as many as possible of the following requirements: (a) it has a high degree of hydrophilicity, (b) it comprises one or more residues selected from the group comprising aspartate, proline, tyrosine and phenylalanine, (c) is has, for higher specificity, no or little homology with other known peptides or polypeptides, (d) it needs to be sufficiently soluble and (e) it comprises no glycosylation or phosphorylation sites unless required for specific reasons. Alternatively, bioinformatics approaches may be followed, for example those described by Moreau, V., Fleury, C., Piquer, D., Nguyen, C., Novali, N., Villard, S., Laune, D., Granier, C. and Molina, F. (2008), PEPOP: Computational design of immunogenic peptides, BMC Bioinformatics 2008, 9:71.

The inventive polypeptide, when used according to the present invention, may be provided in any kind of conformation. For example, the polypeptide may be an essentially unfolded, a partially or a fully folded polypeptide. In a preferred embodiment, the polypeptide is folded in the sense that the epitopes essential for the binding to the inventive autoantibody, or the protein or variant thereof in its entirety, adopt the fold adopted by the native protein in its natural environment. The person skilled in the art is familiar with methods suitable to determine whether or not a polypeptide is folded and if it is, which structure it has, for example limited proteolysis, NMR spectroscopy, CD spectroscopy or X-ray crystallography (see for example Banaszak L. J. (2008), Foundations of Structural Biology, Academics Press, or Teng Q. (2013), Structural Biology: Practical Applications, Springer), preferably CD spectroscopy is used.

The inventive polypeptide may be a fusion protein which comprises amino acid sequences other than those taken from Septin-7, in particular a C-terminal or N-terminal tag, preferably a C-terminal tag, which is, in a preferred embodiment, as used herein, an additional sequence motif or polypeptide having a function that has some biological or physical function and may, for example, be used to purify, immobilize, precipitate or identify the inventive polypeptide. In a more preferred embodiment, the tag is a sequence or domain capable of binding specifically to a ligand, for example a tag selected from the group comprising His tags, thioredoxin, maltose binding protein, glutathione-S-transferase, a fluorescence tag, for example from the group comprising green fluorescent protein.

The inventive polypeptide may be an immobilized polypeptide. In a preferred embodiment, the term "immobilized", as used herein, refers to a molecule bound to a solid carrier insoluble in an aqueous solution, more preferably via a covalent bond, electrostatic interactions, encapsulation or entrapment, for example by denaturing a globular polypeptide in a gel, or via hydrophobic interactions, most preferably via one or more covalent bonds. Various suitable carriers, for example paper, polystyrene, metal, silicon or glass surfaces, microfluidic channels, membranes, beads such as magnetic beads, column chromatography media, biochips, polyacrylamide gels and the like have been described in the literature, for example in Kim, D., and Herr, A. E. (2013), Protein immobilization techniques for microfluidic assays, Biomicrofluidics 7(4), 041501. This way, the immobilized molecule, together with the insoluble carrier, may be separated from an aqueous solution in a straightforward manner, for example by filtration, centrifugation or decanting. An immobilized molecule may be immobilized in a reversible or irreversible manner. For example, the immobilization is reversible if the molecule interacts with the carrier via ionic interactions that can be masked by addition of a high concentration of salt or if the molecule is bound via a cleavable covalent bond such as a disulphide bridge which may be cleaved by addition of thiol-containing reagents. By contrast, the immobilization is irreversible if the molecule is tethered to the carrier via a covalent bond that cannot be cleaved in aqueous solution, for example a bond formed by reaction of an epoxide group and an amine group as frequently used to couple lysine side chains to affinity columns. The protein may be indirectly immobilized, for example by immobilizing an antibody or other entity having affinity to the molecule, followed by formation of a complex to the effect that the molecule-antibody complex is immobilized. Various ways to immobilize molecules are described in the literature, for example in Kim, D., Herr, and A. E. (2013), Protein immobilizsation techniques for microfluidic assays, Biomicrofluidics 7(4), 041501. In addition, various reagents and kits for immobilization reactions are commercially available, for example from Pierce Biotechnology. Preferably, the polypeptide is immobilized using a tag, preferably a His tag.

It is essential that the sample used for the diagnosis in line with the detection of autoantibodies according to the present invention comprises antibodies, also referred to as immunoglobulins. Typically the sample of a bodily fluid comprises a representative set of the entirety of the subject's immunoglobulins. However, the sample, once provided, may be subjected to further processing which may include fractionation, centrifugation, enriching or isolating the entirety of immunoglobulins or any immunoglobulin class of the subject, which may affect the relative distribution of immunoglobulins of the various classes. For example, antibodies from the immunoglobulin class to which the autoantibody belongs may be enriched or purified prior to the detection of the autoantibody, for example by affinity chromatography using an immobilized antibody binding to the constant region of antibodies of said immunoglobulin class, preferably the constant region of IgG.

In a preferred embodiment, the term "diagnosis", as used herein, is to be used in its broadest possible sense and may refer to any kind of procedure aiming to obtain information instrumental in the assessment whether a patient suffers or is likely or more likely than the average or a comparative subject, the latter preferably having similar symptoms, to suffer from certain a disease or disorder in the past, at the time of the diagnosis or in the future, to find out how the disease is progressing or is likely to progress in the future or to evaluate the responsiveness of a patient or patients in general with regard to a certain treatment, for example the administration of immunosuppressive drugs, or to find out whether a sample is from such a patient. Such information may be used for a clinical diagnosis, but may also be obtained by an experimental and/or research laboratory for the purpose of general research, for example to determine the proportion of subjects suffering from the disease in a patient cohort or in a population. In other words, the term "diagnosis" comprises not only diagnosing, but also prognosticating and/or monitoring the course of a disease or disorder, including monitoring the response of one or more patients to the administration of a drug or candidate drug, for example to determine its efficacy. While the result may be assigned to a specific patient for clinical diagnostic applications and may be communicated to a medical doctor or institution treating said patient, this is not necessarily the case for other applications, for example in diagnostics for research purposes, where it may be sufficient to assign the results to a sample from an anonymized patient.

In a preferred embodiment, the teachings of the invention are used to diagnose a disease, preferably a neurological disease, more preferably a neurological autoimmune disease. Since the neurological diseases associated with the presence of an autoantibody to Septin-7 have symptoms that overlap with symptoms associated with a variety of other neurological diseases, the inventive teachings aid in the diagnosis of other neurological diseases, even if the autoantibody can be shown to be absent. In such a case, the patient is more likely to suffer from another neurological disease associated with similar symptoms. For example, encephalopathy is associated with seizures, but so are many non-autoimmune neurological disease such as cerebral dysgenesis, symptomatic epilepsy, head trauma, stroke or vascular malformations, mass lesions, central nervous system infection, encephalitis, meningitis, cysticercosis, HIV encephalopathy, hypoglycemia, hyponatremia, drug toxicity, global cerebral ischemia, hypertensive encephalopathy, eclampsia and hyperthermia, and also a broad range of autoimmune diseases including NMDA receptor autoantibody-associated encephalitis, Lupus erythematosus, Systemic lupus erythematosus, Sjogren's syndrome, Wegener's granulomatosis, sarcoidosis, celiac disease, Crohn's disease, Bechet's disease, and Hashimoto's encephalopathy. Similarly, paralysis can be associated with the presence of Septin-7 antibodies, but also with autoimmune neurological diseases including autoimmune encephalomyelitis, Guillain-Barre syndrome and autoimmune myelitis and non-autoimmune neurological diseases including multiple sclerosis, diabetes, infections, kidney disease, liver disease and hypothyroidism. Therefore, the inventive teachings aid in the diagnosis of a patient suffering from such a symptom, regardless which disease is the underlying cause.

In a preferred embodiment, the methods and products according to the present invention may be used for interaction studies, including determining whether a drug candidate or other compound may interfere with the binding of an autoantibody to Septin-7 or may affect any downstream process or the strength of their binding to their target. In preferred embodiment, they may be used for monitoring the immune response, more preferably the emergence and/or titer of antibodies to Septin-7, following the administration of an immunogenic composition comprising Septin-7 or an immunogenic variant thereof, for example to a mammal, which may be a mammal other than a human such as a laboratory animal.

In many cases the mere detection of the autoantibody, in other words determining whether or not detectable levels of the antibody are present in the sample, is sufficient for the diagnosis. If the autoantibody can be detected, this will be information instrumental for the clinician's diagnosis and indicates an increased likelihood that the patient suffers from a disease.

In a preferred embodiment, the autoantibody is deemed detectable if it can be detected using one or more methods selected from the group comprising immunoprecipitation, indirect immunofluorescence, ELISA or line blot, preferably indirect immunofluorescence. In a preferred embodiment, the relative concentration of the antibody in the serum, compared to the level that may be found in the average healthy subject, may be determined. While in many cases it may be sufficient to determine whether or not autoantibodies are present or detectable in the sample, the method carried out to obtain information instrumental for the diagnosis may involve determining whether the concentration is at least 2, preferably 5, 10, 20, 25, 50, 100, 200, 500, 1000, 10000 or 100000 times higher than the concentration found in the average healthy subject. In a preferred embodiment, the relative concentration of the autoantibody is determined using one or more methods selected from the group comprising semi-quantitative immunoprecipitation, semi-quantitative indirect immunofluorescence, ELISA or semi-quantitative line blot, preferably ELISA. Experimental details are as described in the experimental section of this application or as in textbooks or practical manuals as available at the priority date of this application. Many assays may be carried out in a competitive format, wherein Septin-7 or a variant thereof is bound to a first antibody, which is replaced by a second antibody. For example, the first antibody may be the autoantibody to Septin-7 and the second antibody may be a recombinant antibody, preferably labeled with a detectable label.

The person skilled in the art will appreciate that a clinician does usually not conclude whether or not the patient suffers or is likely to suffer from a disease, condition or disorders solely on the basis of a single diagnostic parameter, but needs to take into account other aspects, for example the presence of other autoantibodies, markers, blood parameters, clinical assessment of the patient's symptoms or the results of medical imaging or other non-invasive methods such as polysomnography, to arrive at a conclusive diagnosis. See Baenkler H. W. (2012), General aspects of autoimmune diagnostics, in Renz, H., Autoimmune diagnostics, 2012, de Gruyter, page 3. The value of a diagnostic agent or method may also reside the possibility to rule out one disease, thus allowing for the indirect diagnosis of another. In a preferred embodiment, the meaning of any symptoms or diseases referred to throughout this application is in line with the person skilled in the art's understanding as of the filing date or, preferably, earliest priority date of this application as evidenced by textbooks and scientific publications. It should be mentioned that the inventive methods or uses or products, taken alone, cannot be used to arrive at a definite, final diagnosis.

Therefore, the term "diagnosis" does preferably not imply that the diagnostic methods or agents according to the present invention will be definitive and sufficient to finalize the diagnosis on the basis of a single test, let alone parameter, but may refer to a contribution to what is referred to as a "differential diagnosis", i. e. a systematic diagnostic procedure considering the likelihood of a range of possible conditions on the basis of a range of diagnostic parameters. Consequently, the inventive method, polypeptide or use, optionally for determining whether a patient suffers from the a disease, may comprise obtaining a sample from a patient, preferably a human patient, determining whether an autoantibody binding to Septin-7 is present in said sample, wherein said determining is performed by contacting the sample with the inventive polypeptide and detecting whether binding occurs between said polypeptide and said autoantibody, preferably using a labeled secondary antibody, wherein said autoantibody binds to said polypeptide if present in the sample, and diagnosing the patient as suffering or being more likely to suffer from said neurological disorder if the autoantibody was determined to be present in the sample.

The term "diagnosis" may also refer in preferred embodiments to a method or agent used to distinguish between two or more conditions associated with similar or identical symptoms, for example autoimmune encephalitis and an encephalitis caused by an infection. Optionally, the presence or absence of an antibody to a viral antigen may be determined according to the present invention, for example relating to a virus causing encephalitis.

The term "diagnosis" may also refer in preferred embodiments to a method or agent used to choose the most promising treatment regime for a patient. In other words, the method or agent may relate to selecting a treatment regimen for a subject. For example, the detection of autoantibodies may indicate that an immunosuppressive therapy is to be selected, which may include administrating to the patient one or more immunosuppressive drugs.

In a preferred embodiment, any information or data demonstrating the presence of absence of the autoantibody may be communicated to the patient or a medical doctor treating the patient, preferably by telephone, in a written form or via the internet, for example as an email or text message.

The present invention relates to a complex comprising an antibody, preferably autoantibody, binding to the inventive polypeptide. Such a complex may be used or detected as part of a method for diagnosing a disease. A liquid sample comprising antibodies from a subject may be used to practice the method if an autoantibody to Septin-7 is to be detected. Such a liquid sample may be any bodily fluid comprising a representative set of antibodies from the subject, preferably a sample comprising antibodies of an immunoglobulin class from the subject selected from the group comprising IgG, IgA and IgM class antibodies, preferably IgG, more preferably IgG1 and IgG2, more preferably IgG1. For example, a sample may be cerebrospinal fluid (CSF), blood or blood serum, lymph, interstitial fluid and is preferably serum or CSF, more preferably serum. It is preferably an ex vivo sample.

The step contacting a liquid sample comprising antibodies with the inventive polypeptide(s) may be carried out by incubating an immobilized form of said polypeptide(s) in the presence of the sample comprising antibodies under conditions that are compatible with the formation of the complex comprising the respective polypeptide and an antibody, preferably an autoantibody, binding to the inventive polypeptide. The liquid sample, then depleted of antibodies binding to the inventive polypeptide(s) may be removed subsequently, followed by one or more washing steps. Finally the complex comprising the antibody or antibodies and the polypeptide(s) may be detected. In a preferred embodiment, the term "conditions compatible with the formation of the complex" are conditions that allow for the specific antigen-antibody interactions to build up the complex comprising the polypeptide and the antibody. In a preferred embodiment such conditions may comprise incubating the polypeptide in sample diluted 1:100 in PBS buffer for 30 minutes at 25° C.

In a preferred embodiment, the term "autoantibody", as used herein, refers to an antibody binding specifically to an endogenous molecule of the animal, preferably mammal, more preferably human, which produces said autoantibody, wherein the level of such antibody is more preferably elevated compared the average of any other antibodies binding specifically to such an endogenous molecule. In a most preferred embodiment, the autoantibody is an autoantibody binding to Septin-7. This means that the autoantibody binds specifically to Septin-7 without demonstrating (significant) binding affinity to other proteins, such as Septin-3, Septin-5, Septin-6, and Septin-11, under stringent conditions. Thus, Septin-7 or variants thereof may form a complex with Septin-3, Septin-5, Septin-6, and Septin-11 to bind the autoantibody specifically to Septin-7 but in such cases the autoantibody exclusively interacts with Septin-7 and none of the other Septin proteins of the complex. An intrinsic property of a Septin-7 specific autoantibody is that such antibody binds to Septin-7 without the presence of other Septin proteins, such as Septin-3, Septin-5, Septin-6, and Septin-11 (nonetheless, the antibody can also interact with Septin-7 being part of a Septin complex). The autoantibody may have the sequence of an antibody's constant regions from the animal, preferably human, making it, but the variable region is able to bind specifically to the endogenous molecule of the animal, more specifically Septin-7. In a preferred embodiment, the autoantibody is isolated and/or purified from a sample, preferably tissue, serum, plasma, blood or CSF from the animal, preferably human. The autoantibody is a polyclonal, native antibody from the animal rather than a synthetic or recombinant antibody.

The method according to the present invention is preferably an in vitro method.

In a preferred embodiment, the detection of the complex for the prognosis, diagnosis, methods or test kit according to the present invention comprises the use of a method selected from the group comprising immunodiffusion techniques, immunoelectrophoretic techniques, light scattering immunoassays, agglutination techniques, labeled immunoassays such as those from the group comprising radiolabeled immunoassay, enzyme immunoassays, preferably ELISA, chemiluminescence immunoassays, and immunofluorescence, preferably indirect immune-fluorescence techniques. The person skilled in the art is familiar with these methods, which are also described in the state of the art, for example in Zane, H. D. (2001), Immunology—Theo-retical & Practical Concepts in Laboratory Medicine, W. B. Saunders Company, in Chapter 14.

Alternatively, a sample comprising tissue comprising the inventive polypeptide rather than a liquid sample may be used. The tissue sample is preferably from a tissue expressing endogenous Septin-7, preferably at an increased level compared to the average tissue in the respective organism's, preferably human body. Such a sample, which may be in the form of a tissue section fixed on a carrier, for example a glass slide for microscopic analysis, may then be contacted with the inventive antibody, preferably autoantibody, binding to the inventive polypeptide. The antibody is preferably labeled to allow for distinction from endogenous antibodies binding to the inventive polypeptide, so that newly formed complexes may be detected and, optionally, quantified. If the amount of complexes formed is lower than the amount found in a sample taken from a healthy subject, the subject from whom the sample examined has been taken is likely to suffer from a disease.

Any data demonstrating the presence or absence of the complex comprising the antibody and the inventive polypeptide may be correlated with reference data. For example, detection of said complex indicates that the patient who provided the sample analyzed has suffered, is suffering or is likely to suffer in the future from a disease. If a patient has been previously diagnosed and the method for obtaining diagnostically relevant information is run again, the amount of complex detected in both runs may be correlated to find out about the progression of the disease and/or the success of a treatment. In a preferred embodiment, any information or data demonstrating the presence of absence of the complex may be communicated to the patient or a medical doctor treating the patient, preferably by telephone, in a written form or via the internet, for example as an email or text message.

The reagents, devices, methods and uses described throughout this application may be used for the diagnosis of a disease. In a preferred embodiment, the term "PNS", abbreviation of paraneoplastic neurological syndrome, as used herein, refers to a systemic disorder indirectly caused by the presence of a tumor, for example, as a result of the production release of substances such as hormones or cytokines not normally produced by the cell of origin of the tumor or are produced at increased concentration or the production and release of biologically active cells. Such systemic order may be revealed by various conditions comprising cerebellitis, epilepsy and sclerosis. Any manifestation of PNS indicates that the patient should be thoroughly examined for the presence of a tumor, although the tumor may be too small for detection.

Therefore, the present invention may also be used for distinguishing an autoimmune disease from an infectious disease, in particular a neuronal autoimmune disease from an infectious disease. Detection of the autoantibody to Septin-7 shows that the disease is an autoimmune disease.

In another preferred embodiment, the prognosis, diagnosis, methods or test kit in line with the inventive teachings contemplate the use of indirect immunofluorescence. The person skilled in the art is familiar with such techniques and the preparation of suitable samples, which are described in the state of the art (U.S. Pat. No. 4,647,543; Voigt, J., Krause, C., Rohwader, E, Saschenbrecker, S., Hahn, M., Danckwardt, M., Feirer, C., Ens, K, Fechner, K, Barth, E, Martinetz, T., and Stöcker, W. (2012), Automated Indirect Immunofluorescence Evaluation of Antinuclear Autoantibodies on HEp-2 Cells," Clinical and Developmental Immunology, vol. 2012, doi:10.1155/2012/65105; Bonilla, E., Francis, L., Allam, F., et al., Immuno-fluorescence microscopy is superior to fluorescent beads for detection of antinuclear antibody reactivity in systemic lupus erythematosus patients, Clinical Immunology, vol. 124, no. 1, pp. 18-21, 2007). Suitable reagents, devices and software packages are commercially available, for example from EUROIMMUN, Lübeck, Germany.

A sample may be subjected to a test to determine only whether an autoantibody binding to Septin-7 is present, but it is preferred that diagnostic methods, tests, devices and the like contemplate determining the presence of autoantibodies to one or more additional polypeptides, preferably related to neurological autoimmune diseases, preferably selected from, more preferably all from the group comprising Hu, Yo, Ri, CV2, PNMA1, PNMA2, DNER/Tr, ARHGAP26, ITPR1, ATP1A3, NBC1, Neurochondrin, CARPVIII, Zic4, Sox1, Ma, MAG, MP0, MBP, GAD65, amphiphysin, recoverin, GABA A receptor (EP13189172.3), GABA B receptor (EP2483417), glycine receptor, gephyrin, IgLON5 (US2016/0349275), DPPX (US2015/0247847), aquaporin-4, MOG, NMDA receptor, AMPA receptors, GRM1, GRM5, LG11, VGCC und mGluR1 and CASPR2, which antigens are preferably immobilized, for example on a medical device such as a line blot. The diagnostically relevant markers Neurochondrin (EP15001186), ITPR1 (EP14003703.7), NBC1 (EP14003958.7), ATP1A3, also referred to as alpha 3 subunit of human neuronal Na(+)/K(+) ATPase (EP14171561.5), Flotillin1/2 (EP3101424), NSF, STX1B and VAMP2 (EP17001205.8) and RGS8 (EP17000666.2), autoantibodies to one or more of which, preferably all, may be detected in addition, have been described in the state of the art.

According to the teachings of the present invention, an antibody, preferably an autoantibody binding to the inventive polypeptide used for the diagnosis of a disease is provided. The person skilled in the art is familiar with methods for purifying antibodies, for example those described in Hermanson, G. T., Mallia, A. K., and Smith, P. K. (1992), Immobilized Affinity Ligand Techniques, San Diego: Academic Press. Briefly, an antigen binding specifically to the antibody of interest, which antigen is the inventive polypeptide, is immobilized and used to purify, via affinity chromatography, the antibody of interest from an adequate source. A liquid sample comprising antibodies from a patient suffering from the neurological disorder identified by the inventors may be used as the source.

According to the invention, an antibody, for example an autoantibody, is provided that is capable of binding specifically to Septin-7. Vice versa, a variant of Septin-7 binds specifically to an autoantibody binding specifically to Septin-7. In a preferred embodiment, the term "antibody", as used herein, refers to any immunoglobulin-based binding moieties, more preferably one comprising at least one immunoglobulin heavy chain and one immunoglobulin light chain, including, but not limited to monoclonal and polyclonal antibodies as well as variants of an antibody, in particular fragments, which binding moieties are capable of binding to the respective antigen, more preferably binding specifically to it. In a preferred embodiment, the term "binding specifically", as used herein, means that the binding is stronger than a binding reaction characterized by a dissociation constant of $1\times10^{-5}$ M, more preferably $1\times10^{-7}$ M, more preferably $1\times10^{-8}$ M, more preferably $1\times10^{-9}$ M, more preferably $1\times10^{-10}$ M, more preferably $1\times10^{-11}$ M, more preferably $1\times10^{-12}$ M, as determined by surface plasmon resonance using Biacore equipment at 25° C. in PBS buffer at pH 7. The antibody may be part of an autoantibody preparation which is heterogeneous or may be a homogenous autoantibody, wherein a heterogeneous preparation comprises a plurality of different autoantibody species as obtainable by preparation from the sera of human donors, for example by affinity chromatography using the immobilized antigen to purify any autoantibody capable of binding to said antigen. The antibody may be glycosylated or non-glycosylated. The antibody may be a recombinant and/or monoclonal mammalian antibody, preferably an animal which is not a human. The person skilled in the art is familiar with methods that may be used for the identification, production and purification of antibodies and variants thereof, for examples those described in EP 2 423 226 A2 and references therein. Preferably the antibody is purified and/or recombinant. Preferably the antibody is bound to the diagnostically useful carrier.

The present invention provides a method for isolating an autoantibody binding to Septin-7, comprising the steps a) contacting a sample comprising the antibody with the inventive polypeptide such that a complex is formed, b) isolating the complex formed in step a), c) dissociating the complex isolated in step b), and d) separating the antibody from the inventive polypeptide. A sample from a patient suffering from the novel neurological disorder identified by the inventors may be used as the source of antibody. Suitable methods are described in the state of the art, for example in the Handbooks "Affinity chromatography", "Strategies for Protein Purification" and "Antibody Purification" (2009/2010), published by GE Healthcare Life Sciences, and in in Philips, Terry, M., Analytical techniques in immunochemistry, 1992, Marcel Dekker, Inc.

The invention provides a pharmaceutical composition comprising the inventive polypeptide, which composition is preferably suitable for administration to a subject, preferably a mammalian subject, more preferably to a human. Such a pharmaceutical composition may comprise a pharmaceutically acceptable carrier. The pharmaceutical composition may, for example, be administered orally, parenterally, by inhalation spray, topically, by eyedrops, rectally, nasally, buccally, vaginally or via an implanted reservoir, wherein the term "parentally", as used herein, comprises subcutaneous, intracutaneous, intravenous, intramuscular, intra-articular, intrasynovial, intrasternal, intrathecal, intralesional and intracranial injection or infusion techniques. The pharmaceutical composition may be provided in suitable dosage forms, for example capsules, tablets and aqueous suspensions and solutions, preferably in sterile form. It may be used in a method of treatment of a disease, which method comprises administering an effective amount of the inventive polypeptide to a subject. In a preferred embodiment, the invention provides a vaccine comprising the inventive polypeptide, optionally comprising an auxiliary agent such as an adjuvant or a buffer, and the use of the inventive polypeptide for the preparation of a vaccine.

Within the scope of the present invention, a medical or diagnostic device comprising, preferably coated with a reagent for detecting the inventive (auto)antibody and/or the inventive polypeptide is provided. Preferably such a medical or diagnostic device comprises the inventive polypeptide in a form that allows contacting it with an aqueous solution, more preferably the liquid human sample, in a straightforward manner. In particular, the inventive polypeptide comprising may be immobilized on the surface of a carrier, preferably selected from the group comprising glass plates or slides, biochips, microtiter plates, beads, for example magnetic beads, apharesis devices, chromatography columns, membranes or the like. Exemplary medical devices include line blots, microtiter plates, glass slides for microscopy, beads, preferably magnetic beads, and biochips. In addition to the inventive polypeptide, the medical or diagnostic device may comprise additional polypeptides, for example positive or negative controls such as samples comprising or not comprising an antibody binding to the polypeptide of interest, or known other antigens binding to autoantibodies of diagnostic value, particularly those related other diseases associated with one or more identical or similar symptoms.

The inventive teachings provide a kit, preferably for diagnosing a disease. Such a kit may comprise instructions detailing how to use the kit and a means for contacting the inventive polypeptide with a bodily fluid sample from a subject, preferably a human subject, for example a line blot, wherein the inventive polypeptide is immobilized on the line blot. Furthermore, the kit may comprise a positive control, for example a batch of autoantibody or recombinant antibody known to bind to the polypeptide according to the present invention, and a negative control, for example a protein having no detectable affinity to the inventive polypeptide such as bovine serum albumin. Finally, such a kit may comprise one or more standard solutions, also referred to as calibrator, of an antibody binding to Septin-7, preferably with a known absolute or relative concentration, for preparing a calibration curve. Preferably the kit comprises two calibrators, wherein the first calibrator has a concentration of the antibody that is no more than 50, 40, 30, 20, 10 5, 2.5 or 1% of the concentration of the antibody in the second calibrator. In a preferred embodiment, a device comprising the diagnostically useful carrier is calibrated by detecting the antibody concentration in at least two calibrators and obtaining a concentration value for each calibrators, preferably three, four or five or more calibrators, followed by setting up a standard calibration curve.

In a preferred embodiment, the kit comprises a means for detecting an autoantibody binding to the inventive polypeptide, preferably by detecting a complex comprising the inventive polypeptide and an antibody binding to the inventive polypeptide. Such means is preferably an agent that binds to said complex and modifies the complex or carries a label such that makes the complex detectable. For example, said means may be a labeled antibody binding to said polypeptide, at a binding site other than the binding site recognized by the primary antibody or to a constant region of the primary antibody. Alternatively, said means may be a secondary antibody binding to the constant region of the autoantibody, preferably a secondary antibody specific for mammalian IgG class of antibodies. A multitude of methods and means for detecting such a complex have been described in the state of the art, for example in Philips, Terry, M., Analytical techniques in immunochemistry, 1992, Marcel Dekker, Inc.

Septin-7 or a variant thereof may be produced or provided in the form of a cell comprising and/or expressing a nucleic acid encoding said polypeptide. If a nucleic acid comprising a sequence that encodes for the inventive polypeptide or variant thereof is used, such a nucleic acid may be an unmodified nucleic acid. In a preferred embodiment, the nucleic acid is a nucleic acid that, as such, does not occur in nature and comprises, compared to natural nucleic acid, at least one modification, for example an isotopic content or chemical modifications, for example a methylation, sequence modification, label or the like indicative of synthetic origin. In a preferred embodiment, the nucleic acid is a recombinant nucleic acid or part or a nucleic acid, and is, in a more preferred embodiment, part of a vector, in which it may be functionally linked with a promoter that allows for expression, preferably overexpression of the nucleic acid. The person skilled in the art is familiar with a variety of suitable vectors, of which are commercially available, for example from Origene. For example, a vector encoding for fusion constructs with a C-terminal GFP may be used. The cell may be a eukaryotic or prokaryotic cell, preferably of eukaryotic cell, such as a yeast cell, and is more preferably a mammalian, more preferably a human cell such as a HEK293 cell. Examples of a mammalian cell include a HEK293, CHO or COS-7 cell. The cell comprising the nucleic acid encoding for the inventive polypeptide may be a recombinant cell or an isolated cell wherein the term "isolated" means that the cell is enriched such that, compared to the environment of the wild type of said cell, fewer cells of other differentiation or species or in fact no such other cells are present.

In a preferred embodiment, the medical device according to the present invention, preferably a slide suitable for microscopy, comprises one or more, preferably all reagents from the group comprising a first eukaryotic cell expressing, preferably overexpressing Septin-7 or a variant thereof, a eukaryotic, preferably mammalian tissue expressing endogenous Septin-7 such as rat or primate cerebellum, a second eukaryotic cell, which is the same type of cell as the first eukaryotic cell, but does not express or overexpress Septin-7. The first and the second eukaryotic cell are cultured cells derived from an isolated cell line such as HEK293. Preferably, the first and the second cell are each transfected with a vector sharing the same backbone, wherein the vector used to transfect the first cell comprises a nucleic acid encoding Septin-7 or a variant thereof and the vector used to transfect the second cell does not comprise Septin-7 or a variant thereof. The second cell may serve as a negative control. The reagents may be spatially separate on the medical device, such that they may be evaluated independently, with no antigen from one reagent contaminating another. In a more preferred embodiment, the first and/or the second cell is a fixed cell, for example fixed using methanol or acetone. Protocols for fixing cells are described in the state of the art. As an additional reagent, a secondary labeled antibody, preferably labeled with a fluorescent dye may be provided. The reagents and the medical device may be part of a kit.

In a preferred embodiment, a microtiter plate, membrane, blot such as dot blot or line blot is used to carry out the diagnostic method according to the invention. The person skilled in the art is familiar with the experimental setup of a line blot, which is described in the state of the art (Raoult, D., and Dasch, G. A. (1989), The line blot: an immunoassay for monoclonal and other antibodies. Its application to the serotyping of gram-negative bacteria. J. Immunol. Methods, 125 (1-2), 57-65; WO2013041540). If the medical device is a line blot, it may comprise Septin-7 or a variant thereof immobilized on a membrane, preferably in the shape of a test stripe. The membrane may comprise one or more additional antigens, spatially separated from Septin-7. The membrane may comprise a control band indicating addition of the sample such as a blood sample and/or a control band indicating addition of a secondary antibody. A kit may comprise any component, preferably all from the group comprising the line blot, a secondary antibody and a washing solution.

In another preferred embodiment, the medical device is a microtiter plate comprising at least 8 wells. At least one of the wells is directly or indirectly coated with Septin-7 or a variant thereof. At least 3, preferably 4, more preferably 5 calibrators are provided that comprise an antibody to Septin-7 at a defined concentration and may be used to set up a calibration curve for semi-quantitative analysis. A secondary antibody comprising an enzymatically active label may be provided. A kit may comprise any component, preferably all from the group comprising the microtiter plate, the calibrators, a washing solution and the secondary antibody.

In another preferred embodiment, the medical device is a bead coated directly or indirectly with Septin-7 or a variant thereof. The bead may be selected from the group comprising a magnetic bead and a fluorescent bead. A secondary antibody comprising a label capable or chemiluminescence or fluorescence may be provided. A positive control comprising an antibody to Septin-7 may be provided. At least 3, preferably 4, more preferably 5 calibrators may be provided that comprise an antibody to Septin-7 at a defined concentration and may be used to set up a calibration curve for semi-quantitative analysis. If the label is capable of generating chemiluminescence, a solution may be provided that comprises additional components required for the chemiluminescence reaction. For example, if the label is an enzyme, the solution comprises substrates. If the label is a compound capable of generating chemiluminescence such as an acridinium ester, additional compounds required for the reaction are provided in the solution. A kit may comprise any component, preferably all from the group comprising the bead, the secondary antibody, the calibrators, a washing solution and the solution comprising additional components.

The inventive teachings may not only be used for a diagnosis, but also for preventing or treating a disease, more specifically a method for preventing or treating a disease, comprising the steps a) reducing the concentration of autoantibodies binding to the inventive polypeptide in the subject's blood and/or b) administering one or more immunosuppressive pharmaceutical substances, preferably selected from the group comprising rituximab, prednisone, methylprednisolone, cyclophosphamide, mycophenolate mofetil, intravenous immunoglobulin, tacrolimus, cyclosporine, methotrexate, azathioprine and/or the pharmaceutical composition.

In a preferred embodiment, the present invention provides a use of a reagent for the detection of an autoantibody to Septin-7 or a reagent binding to such autoantibody, or of a nucleic acid encoding Septin-7 or the variant or a nucleic acid hybridizing specifically to a nucleic acid encoding Septin-7 or a vector or cell comprising said nucleic acid for the manufacture of kit for the diagnosis of a disease.

In a preferred embodiment, any method or use according to the present invention may be intended for a non-diagnostic use, i.e. determining the presence of an autoantibody to binding to Septin-7 for a use other than diagnosing a patient. For example, the method or use may be for testing in vitro the efficiency of a medical device designed to remove an autoantibody from a patient's blood, wherein the testing is performed on a liquid other than patient's blood. After the use of the medical device with a patient, its capacity to remove autoantibody may be checked by running a solution comprising antibody to Septin-7 through the device, followed by use of the method according to the present invention to confirm that less or no antibody is in the solution that has been passed through the device, i.e. showing that the device has still the capacity to remove antibody from the solution.

In another preferred embodiment, the method may be for confirming the reliability of a diagnostic assay and may involve detecting an antibody to Septin-7 in a solution, which is not a sample from a patient, but is known to comprise an antibody to Septin-7, preferably at a known concentration. Alternatively, the solution may be a negative control not comprising the antibody to check the background. Such method may be run in parallel with, after or before a diagnostic method. In a preferred embodiment, any method or use according to the present invention may be intended for generating an autoantibody profile, preferably for detecting a disease in a mammal, preferably a human. In a preferred embodiment, any method or use may be for detecting disease-associated markers in a sample from neurological disease patients.

In a preferred embodiment, any method or use according to the present invention may be for identifying a subject at risk of suffering from or developing a neurological disease and/or a tumor.

In a preferred embodiment, the present invention provides an apparatus for analyzing a sample from a patient to detect an autoantibody against Septin-7, indicating an increased likelihood of a disease or of developing a disease, comprising:
   a. a carrier, which contains a means for capturing the autoantibody from the sample when the sample is contacted with the carrier,
   b. a detectable means capable of binding to the antibody captured by the carrier when the detectable means is contacted with the carrier, wherein the detectable means is a labeled secondary antibody capable of binding to the antibody captured on the carrier, c. optionally a means for removing any sample from the carrier and the detectable means, preferably by washing;
d. a detecting device for detecting the presence of the detectable means and converting the results into an electrical signal, and optionally a means for receiving the electronical signal from the detecting device and determining if the level of the signal is indicative of an increased likelihood of having or developing a disease, by comparing with the level of signal detected in the background or an input reference value obtained with samples from healthy subjects or by comparing the level of signal obtained with one sample with the level of signal obtained with a second sample obtained at a later time point, preferably at least one month later.

The present application comprises a range of sequences, more specifically:

```
(human Septin-7) Q16181-1
                                              SEQ ID NO: 1
MSVSARSAAAEERSVNSSTMVAQQKNLEGYVGFANLPNQVYRKSVKRGFEFTLMVVGESGLGKS

TLINSLFLTDLYSPEYPGPSHRIKKTVQVEQSKVLIKEGGVQLLLTIVDTPGFGDAVDNSNCWQ

PVIDYIDSKFEDYLNAESRVNRRQMPDNRVQCCLYFIAPSGHGLKPLDIEFMKRLHEKVNIIPL

IAKADTLTPEECQQFKKQIMKEIQEHKIKIYEFPETDDEEENKLVKKIKDRLPLAVVGSNTIIE

VNGKRVRGRQYPWGVAEVENGEHCDFTILRNMLIRTHMQDLKDVTNNVHYENYRSRKLAAVTYN

GVDNNKNKGQLTKSPLAQMEEERRSHVAKMKKMEMEMEQVFEMKVKEKVQKLKDSEAELQRRHE

QMKKNLEAQHKELEEKRRQFEDEKANWEAQQRILEQQNSSRTLEKNKKKGKIF (mouse Septin-7) O55131-1
                                              SEQ ID NO: 2
MSVSARSAAAEERSVNCGTMAQPKNLEGYVGFANLPNQVYRKSVKRGFEFTLMVVGESGLGKST

LINSLFLTDLYSPEYPGPSHRIKKTVQVEQSKVLIKEGGVQLLLTIVDTPGFGDAVDNSNCWQP

VIDYIDSKFEDYLNAESRVNRRQMPDNRVQCCLYFIAPSGHGLKPLDIEFMKRLHEKVNIIPLI

AKADTLTPEECQQFKKQIMKEIQEHKIKIYEFPETDDEEENKLVKKIKDRLPLAVVGSNTIIEV

NGKRVRGRQYPWGVAEVENGEHCDFTILRNMLIRTHMQDLKDVTNNVHYENYRSRKLAAVTYNG

VDNNKNKGQLTKSPLAQMEEERREHVAKMKKMEMSMEQVFEMKVKEKVQKLKDSEAELQRRHEQ

MKKNLEAQHKELEEKRRQFEEEKANWEAQQRILEQQNSSRTLEKNKKKGKIF (rat Septin-7) Q9WVC0-1
                                              SEQ ID NO: 3
MSVSARSAAAEERSVNCSTMAQPKNLEGYVGFANLPNQVYRKSVKRGFEFTLMVVGESGLGKST

LINSLFLTDLYSPEYPGPSHRIKKTVQVEQSKVLIKEGGVQLLLTIVDTPGFGDAVDMSNCWQP

VIDYIDSKFEDYLNAESRVNRRQMPDNRVQCCLYFIAPSGHGLKPLDIEFMKRLHEKVNIIPLI

AKADTLTPEECQQFKKQIMKEIQGHKIKIYEFPETDDEEENKLVKKIKDRLPLAVVGSNTIIEV

NGKRVRGRQYPWGVAEVENGEHCDFTILRNMLIRTHMQDLKDVTNNVHYENTRSRKLAAVTYNG

VDNNKNKGQLTKSPLAQMEEERREHVAKMKKMEMEMEQVFEMKVKEKVQKLKDSEAELQRRHEQ

MKNNLEAQHKELEEKRRQFEEEKANWEAQQRILEQQNSSRTLEKNKKKGKIF (human Septin-3)
                                              SEQ ID NO: 4
MSKGLPETRIDAAMSELVPFPRPKPAVPMKPMSINSNLLGYIGIDTIIEQMRKKTMKTGFDFNI

MVVGQSGLGKSTLVNTLFKSQVSRKASSWNREEKIPKTVEIKAIGHVIEEGGVKMKLTVIDTPG

FGDQINNENCWEPIEKYINEQYEKFLKEEVNIARKKRIPDTRVHCCLYFISPTGHSLRPLDLEF

MKHLSKVVNIIPVIAKADTMTLEEKSEFKQRVRKELEVNGIEFYPQKEFDEDLEDKTENDKIRQ

ESMPFAVVGSDKEYQVNGKRVLGRKTPWGIIEVENLNHCEFALLRDFVIRTHLQDLKEVTHNIH

YETYRAKRLNDNGGLPPGEGLLGTVLPPVPATPCPTAE (human Septin-5)
                                              SEQ ID NO: 5
MSTGLRYKSKLATPEDKQDIDKQYVGFATLPNQVHRKSVKKGFDFTLMVAGESGLGKSTLVHSL

FLTDLYKDRKLLSAEERISQTVEILKHTVDIEEKGVKLKLTIVDTPGFGDAVNNTECWKPITDY

VDQQFEQYFRDESGLNRKNIQDNRVHCCLYFISPFGHGLRPVDVGFMKALHEKVNIVPLIAKAD
```

CLVPSEIRKLKERIREEIDKFGIHVYQFPECDSDEDEDFKQQDRELKESAPFAVIGSNTVVEAK

GQRVRGRLYPWGIVEVENQAHCDFVKLRNMLIRTHMHDLKDVTCDVHYENYRAHCIQQMTSKLT

QDSRMESPIPILPLPTPDAETEKLIRMKDEELRRMQEMLQRMKQQMQDQ (human Septin-6)
SEQ ID NO: 6
MAATDIARQVGEGCRTVPLAGHVGFDSLPDQLVNKSVSQGFCFNILCVGETGLGKSTLMDTLFN

TKFEGEPATHTQPGVQLQSNTYDLQESNVRLKLTIVSTVGFGDQINKEDSYKPIVEFIDAQFEA

YLQEELKIRRVLHTYHDSRIHVCLYFIAPTGHSLKSLDLVTMKKLDSKVNIIPIIAKADAISKS

ELTKFKIKITSELVSNGVQIYQFPTDDESVAEINGTMNAHLPFAVIGSTEELKIGNKMMRARQY

PWGTVQVENEAHCDFVKLREMLIRVNMEDLREQTHTRHYELYRRCKLEEMGFKDTDPDSKPFSL

QETYEAKRNEFLGELQKKEEEMRQMFVQRVKEKEAELKEAEKELHEKFDRLKKLHQDEKKKLED

KKKSLDDEVNAFKQRKTAAELLQSQGSQAGGSQTLKRDKEKKNNPWLTE (human Septin-11)
SEQ ID NO: 7
MAVAVGRPSNEELRNLSLSGHVGFDSLPDQLVNKSTSQGFCFNILCVGETGIGKSTLMDTLFNT

KFESDPATHNEPGVRLKARSYELQESNVRLKLTIVDTVGFGDQINKDDSYKPIVEYIDAQFEAY

LQEELKIKRSLFNYHDTRIHACLYFIAPTGHSLKSLDLVTMKKLDSKVNIIPIIAKADTIAKNE

LHKFKSKIMSELVSNGVQIYQFPTDEETVAEINATMSVHLPFAVVGSTEEVKIGNKMAKARQYP

WGVVQVENENHCDFVKLREMLIRVNMEDLREQTHTRHYELYRRCKLEEMGFKDTDPDSKPFSLQ

ETYEAKRNEFLGELQKKEEEMRQMFVMRVKEKEAELKEAEKELHEKFDLLKRTHQEEKKKVEDK

KKELEEEVNNFQKKKAAAQLLQSQAQQSGAQQTKKDKDKKNASFT (human Septin-7, His tagged)
SEQ ID NO: 8
MSVSARSAAAEERSVNSSTMVAQQKNLEGYVGFANLPNQVYRKSVKRGFEFTLMVVGESGLGKS

TLINSLFLTDLYSPEYPGPSHRIKKTVQVEQSKVLIKEGGVQLLLTIVDTPGFGDAVDNSNCWQ

PVIDYIDSKFEDYLNAESRVNRRQMPDNRVQCCLYFIAPSGHGLKPLDIEFMKRLHEKVNIIPL

IAKADTLTPEECQQFKKQIMKEIQEHKIKIYEFPETDDEEENKLVKKIKDRLPLAVVGSNTIIE

VNGKRVRGRQYPWGVAEVENGEHCDFTILRNMLIRTHMQDLKDVTNNVHYENYRSRKLAAVTYN

GVDNNKNKGQLTKSPLAQMEEERREHVAKMKKMEMEMEQVFEMKVKEKVQKLKDSEAELQRRHE

QMKKNLEAQHKELEEKRRQFEDEKANWEAQQRILEQQNSSRTLEKNKKKGKIFLEHHHHHHHH (human Septin-3, His tagged)
SEQ ID NO: 9
MSKGLPETRTDAAMSELVPEPRPKPAVPMKPMSINSNLLGYIGIDTIIEQMRKKTMKTGFDFNI

MVVGQSGLGKSTLVNTLFKSQVSRKASSWNREEKIPKTVEIKAIGHVIEEGGVKMKLTVIDTPG

FGDQINNENCWEPIEKYINEQYEKFLKEEVNIARKKRIPDTRVHCCLYFISPTGHSLRPLDLEF

MKHLSKVVNIIPVIAKADTMTLEEKSEFKQRVRKELEVNGIEFYPQKEFDEDLEDKTENDKIRQ

ESMPFAVVGSDKEYQVNGKRVLGRKTPWGIIEVENLNHCEFALLRDFVIRTHLQDLKEVTHNIH

YETYRAKRLNDNGGLPPGEGLLGTVLPPVPATPCPTAELEHHHHHHH (human Septin-5, His tagged)
SEQ ID NO: 10
MSTGLRYKSKLATPEDKQDIDKQYVGFATLPNQVHRKSVKKGFDFTLMVAGESGLGKSTLVHSL

FLTDLYKDRKLLSAEERISQTVEILKHTVDIEEKGVKLKLTIVDTPGFGDAVNNTECWKPITDY

VDQQFEQYFRDESGLNRKNIQDNRVHCCLYFISPFGHGLRPVDVGFMKALHEKVNIVPLIAKAD

CLVPSEIRKLKERIREEIDKFGIHVYQFPECDSDEDEDFKQQDRELKESAPFAVIGSNTVVEAK

GQRVRGRLYPWGIVEVENQAHCDFVKLRNMLIRTHMHDLKDVTCDVHYENYRAHCIQQMTSKLT

-continued

QDSRMESPIPILPLPTPDAETEKLIRMKDEELRRMQEMLQRMKQQMQDQLEHHHHHHHH (human Septin-6, His tagged)

SEQ ID NO: 11

MAATDIARQVGEGCRTVPLAGHVGFDSLPDQLVNKSVSQGFCFNILCVGETGLGKSTLMDTLFN

TKFEGFPATHTQPGVQLQSNTYDLQESNVRLKLTIVSTVGFGDQINKEDSYKPIVEFIDAQFEA

YLQEELKIRRVLHTYHDSRIHVCLYFIAPTGHSLKSLDLVTMKKLDSKVNIIPIIAKADAISKS

ELTKFKIKITSELVSNGVQIYQFPTDDESVAEINGTMNAHLPFAVIGSTEELKIGNKMMRARQY

PWGTVQVENEAHCDFVKLREMLIRVNMEDLREQTHTRHYELYRRCKLEEMGFKDTDPDSKPFSL

QETYEAKRNEFLGELQKKEEEMRQMFVQRVKEKEAELKEAEKELHEKFDRLKKLHQDEKKKLED

KKKSLDDEVNAFKQRKTAAELPQSQGSQAGGSQTLKRDKEKKNNPWLCTELEHHKHHHHH (human Septin-11, His tagged)

SEQ ID NO: 12

MAVAVGRPSNEELRNLSLSGHVGFDSLPDQLVNKSTSQGFCFNILCVGETGIGKSTLMDTLFNT

KFESDPATHNEPGVRLKARSYELQESNVRLKLTIVDTVGFGDQINKDDSYKPIVEYIDAQFEAY

LQEELKIKRSLFNYHDTRIHACLYFIAPTGHSLKSLDLVTMKKLDSKVNIIPIIAKADTIAKNE

LHKFKSKIMSELVSNGVQIYQFPTDEETVAEINATMSVHLPFAVVGSTEEVKIGNKMAKARQYP

WGVVQVENENHCDFVKLREMLIRVNMEDLREQTHTRHYELYRRCKLEEMGFKDTDPDSKPFSLQ

ETYEAKRNEFLGELQKKEEEMRQMFVMRVKEKEAELKEAEKELHEKFDLLKRTHQEEKKKVEDK

KKELEEEVNNFQKKKAAAQLLQSQAQQSGAQQTKKDKDKKNASFTLEHHHHHHHH (pTriEx-1-Septin-7, His tagged)

SEQ ID NO: 13

GGGGAATTGTGAGCGGATAACAATTCCCCGGAGTTAATCCGGGACCTTTAATTCAACCCAACAC

AATATATTATAGTTAAATAAGAATTATTATCAAATCATTTGTATATTAATTAAAATACTATACT

GTAAATTACATTTTATTTACAATCAAAGGAGATATACCATGTCGGTCAGTGCGAGATCCGCTGC

TGCTGAGGAGAGGAGCGTCAACAGCAGCACCATGGTAGCTCAACAGAAGAACCTTGAAGGCTAT

GTGGGATTTGCCAATCTCCCAAATCAAGTATACAGAAAATCGGTGAAGAGAGGTTTTGAATTCA

CGCTTATGGTAGTGGGTGAATCTGGATTGGGAAAGTCGACATTAATCAACTCATTATTCCTCAC

AGATTTGTATTCTCCAGAGTATCCAGGTCCTTCTCATAGAATTAAAAAGACTGTACAGGTGGAA

CAATCCAAAGTTTTAATCAAAGAAGGTGGTGTTCAGTTGCTGCTCACAATAGTTGATACCCCAG

GATTTGGAGATGCAGTGGATAATAGTAATTGCTGGCAGCCTGTTATCGACTACATTGATAGTAA

ATTTGAGGACTACCTAAATGCAGAATCACGAGTGAACAGACGTCAGATGCCTGATAACAGGGTG

CAGTGTTGTTTATACTTCATTGCTCCTTCAGGACATGGACTTAAACCATTGGATATTGAGTTTA

TGAAGCGTTTGCATGAAAAAGTGAATATCATCCCACTTATTGCCAAAGCAGACACACTCACACC

AGAGGAATGCCAACAGTTTAAAAAACAGATAATGAAAGAAATCCAAGAACATAAAATTAAAATA

TAGGAATTTCCAGAAACAGATGATGAAGAAGAAAATAAACTTGTTAAAAAGATAAAGGACCGTT

TACCTCTTGCTGTGGTAGGTAGTAATACTATCATTGAAGTTAATGGCAAAAGGGTCAGAGGAAG

GCAGTATCCTTGGGGTGTTGCTGAAGTTGAAAATGGTGAACATTGTGATTTTACAATCCTAAGA

AATATGTTGATAAGAACACACATGCAGGACTTGAAAGATGTTACTAATAATGTCCACTATGAGA

ACTACAGAAGCAGAAAACTTGCAGCTGTGACTTATAATGGAGTTGATAACAACAAGAATAAAGG

GCAGCTGACTAAGAGCCCTCTGGCACAAATGGAAGAAGAAAGAAGGGAGCATGTAGCTAAAATG

AAGAAGATGGAGATGGAGATGGAGCAGGTGTTTGAGATGAAGGTCAAAGAAAAAGTTCAAAAAC

TGAAGGACTCTGAAGCTGAGCTCCAGCGGCGCCATGAGCAAATGAAAAAGAATTTGGAAGCACA

GCACAAAGAATTGGAGGAAAAACGTCGTCAGTTCGAGGATGAGAAAGCAAACTGGGAAGCTCAA

-continued

```
CAACGTATTTTAGAACAACAGAACTCTTCAAGAACCTTGGAAAAGAACAAGAAGAAAGGGAAGA
TCTTTCTCGAGCACCACCATCACCATCACCATCACTAAGTGATTAACCTCAGGTGCAGGCTGCC
TATCAGAAGGTGGTGGCTGGTGTGGCCAATGCCCTGGCTCACAAATACCACTGAGATCGATCTT
TTTCCCTCTGCCAAAAATTATGGGGACATCATGAAGCCCCTTGAGCATCTGACTTCTGGCTAAT
AAAGGAAATTTATTTTCATTGCAATAGTGTGTTGGAATTTTTTGTGTCTCTCACTCGGAAGGAC
ATATGGGAGGGCAAATCATTTAAAACATCAGAATGAGTATTTGGTTTAGAGTTTGGCAACATAT
GCCCATATGTAACTAGCATAACCCCTTGGGGCCTCTAAACGGGTCTTGAGGGGTTTTTGCTGA
AAGCATGCGGAGGAAATTCTCCTTGAAGTTTCCCTGGTGTTCAAAGTAAAGGAGTTTGCACCAG
ACGCACCTCTGTTCACTGGTCCGGCGTATTAAAACACGATACATTGTTATTAGTACATTTATTA
AGCGCTAGATTCTGTGCGTTGTTGATTTACAGACAATTGTTGTACGTATTTTAATAATTCATTA
AATTTATAATCTTTAGGGTGGTATGTTAGAGCGAAAATCAAATGATTTTCAGCGTCTTTATATC
TGAATTTAAATATTAAATCCTCAATAGATTTGTAAAATAGGTTTCGATTAGTTTCAAACAAGGG
TTGTTTTTCCGAACCGATGGCTGGACTATCTAATGGATTTTCGCTCAACGCCACAAAACTTGCC
AAATCTTGTAGCAGCAATCTAGCTTTGTCGATATTCGTTTGTGTTTTGTTTTGTAATAAAGGTT
CGACGTCGTTCAAAATATTATGCGCTTTTGTATTTCTTTCATCACTGTCGTTAGTGTACAATTG
ACTCGACGTAAACACGTTAAATAGAGCTTGGACATATTTAACATCGGGCGTGTTAGCTTTATTA
GGCCGATTATCGTCGTCGTCCCAACCCTCGTCGTTAGAAGTTGCTTCCGAAGACGATTTTGCCA
TAGCCACACGACGCCTATTAATTGTGTCGGCTAACACGTCCGCGATCAAATTTGTAGTTGAGCT
TTTTGGAATTATTTCTGATTGCGGGCGTTTTTGGGCGGGTTTCAATCTAACTGTGCCCGATTTT
AATTCAGACAACACGTTAGAAAGCGATGGTGCAGGCGGTGGTAACATTTCAGACGGCAAATCTA
CTAATGGCGGCGGTGGTGGAGCTGATGATAAATCTACCATCGGTGGAGGCGCAGGCGGGGCTGG
CGGCGGAGGCGGAGGCGGAGGTGGTGGCGGTGATGCAGACGGCGGTTTAGGCTCAAATGTCTCT
TTAGGCAACACAGTCGGCACCTCAACTATTGTACTGGTTTCGGGCGCCGTTTTTGGTTTGACCG
GTCTGAGACGAGTGCGATTTTTTTCGTTTCTAATAGCTTCCAACAATTGTTGTCTGTCGTCTAA
AGGTGCAGCGGGTTGAGGTTCCGTCGGCATTGGTGGAGCGGGCGGCAATTCAGACATCGATGGT
GGTGGTGGTGGAGGCGCTGGAATGTTAGGCACGGGAGAAGGTGGTGGCGGCGGTGCCGCCG
GTATAATTTGTTCTGGTTTAGTTTGTTCGCGCACGATTGTGGGCACCGGCGCAGGCGCCGCTGG
CTGCACAACGGAAGGTCGTCTGCTTCGAGGCAGCGCTTGGGGTGGTGGCAATTCAATATTATAA
TTGGAATACAAATCGTAAAAATCTGCTATAAGCATTGTAATTTCGCTATCGTTTACCGTGCCGA
TATTTAACAACCGCTCAATGTAAGCAATTGTATTGTAAAGAGATTGTCTCAAGCTCGGAACGCT
GCGCTCGGTCGTTCGGCTGCGGCGAGCGGTATCAGCTCACTCAAAGGCGGTAATACGGTTATCC
ACAGAATCAGGGGATAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCTGACGAGCATCACAAAAA
TCGACGCTCAAGTCAGAGGTGGCGAAACCCGACAGGACTATAAAGATACCAGGCGTTTCCCCCT
GGAAGCTCCCTCGTGCGCTCTCCTGTTCCGACCCTGCCGCTTACCGGATACCTGTCCGCCTTTC
TCCCTTCGGGAAGCGTGGCGCTTTCTCAATGCTCACGCTGTAGGTATCTCAGTTCGGTGTAGGT
CGTTCGCTCCAAGCTGGGCTGTGTGCACGAACCCCCCGTTCAGCCCGACCGCTGCGCCTTATCC
GGTAACTATCGTCTTGAGTCCAACCCGGTAAGACACGACTTATCGCCACTGGCAGCAGCCACTG
GTAACAGGATTAGCAGAGCGAGGTATGTAGGCGGTGCTAGAGAGTTCTTGAAGTGGTGGCCTAA
CTACGGCTACACTAGAAGGACAGTATTTGGTATCTGCGCTCTGCTGAAGCCAGTTACCTTCGGA
AAAAGAGTTGGTAGCTCTTGATCCGGCAAACAAACCACCGCTGGTAGCGGTGGTTTTTTTGTTT
```

-continued

```
GCAAGCAGCAGATTACGCGCAGAAAAAAAGGATCTCAAGAAGATCCTTTGTTACCAATGCTTAA

TCAGTGAGGCACCTATCTCAGCGATCTGTCTATTTCGTTCATCCATAGTTGCCTGACTCCCCGT

CGTGTAGATAACTACGATACGGGAGGGCTTACCATCTGGCCCCAGTGCTGCAATGATACCGCGA

GACCCACGCTCACCGGCTCCAGATTTATCAGCAATAAACCAGCCAGCCGGAAGGGCCGAGCGCA

GAAGTGGTCCTGCAACTTTATCCGCCTCCATCCAGTCTATTAATTGTTGCCGGGAAGCTAGAGT

AAGTAGTTCGCCAGTTAATAGTTTGCGCAACGTTGTTGCCATTGCTACAGGCATCGTGGTGTCA

CGCTCGTCGTTTGGTATGGCTTCATTCAGCTCCGGTTCCCAACGATCAAGGCGAGTTACATGAT

CCCCCATGTTGTGCAAAAAAGCGGTTAGCTCCTTCGGTCCTCCGATCGTTGTCAGAAGTAAGTT

GGCCGCAGTGTTATCACTCATGGTTATGGCAGCACTGCATAATTCTCTTACTGTCATGCCATCC

GTAAGATGCTTTTCTGTGACTGGTGAGTACTCAACCAAGTCATTCTGAGAATAGTGTATGCGGC

GACCGAGTTGCTCTTGCCCGGCGTCAATACGGGATAATACCGCGCCACATAGCAGAACTTTAAA

AGTGCTCATCATTGGAAAACGTTCTTCGGGGCGAAAACTCTCAAGGATCTTACCGCTGTTGAGA

TCCAGTTCGATGTAACCCACTCGTGCACCCAACTGATCTTCAGCATCTTTTACTTTCACCAGCG

TTTCTGGGTGAGCAAAAACAGGAAGGCAAAATGCCGCAAAAAAGGGAATAAGGGCGACACGGAA

ATGTTGAATACTCATACTCTTCCTTTTTCAATATTATTGAAGCATTTATCAGGGTTATTGTCTC

ATGTCCGCGCGTTTCCTGCATCTTTTAATCAAATCCCAAGATGTGTATAAACCACCAAACTGCC

AAAAAATGAAAACTGTCGACAAGCTCTGTCCGTTTGCTGGCAACTGCAAGGGTCTCAATCCTAT

TTGTAATTATTGAATAATAAAACAATTATAAATGTCAAATTTGTTTTTTATTAACGATACAAAC

CAAACGCAACAAGAACATTTGTAGTATTATCTATAATTGAAAACGCGTAGTTATAATCGCTGAG

GTAATATTTAAAATCATTTTCAAATGATTCACAGTTAATTTGCGACAATATAATTTTATTTTCA

CATAAACTAGACGCCTTGTCGTCTTCTTCTTCGTATTCCTTCTCTTTTTCATTTTTCTCTTCAT

AAAAATTAACATAGTTATTATCGTATCCATATATGTATCTATCGTATAGAGTAAATTTTTTGTT

GTCATAAATATATATGTCTTTTTTAATGGGGTGTATAGTAGCGCTGCGCATAGTTTTTCTGTAA

TTTACAACAGTGCTATTTTCTGGTAGTTCTTCGGAGTGTGTTGCTTTAATTATTAAATTTATAT

AATCAATGAATTTGGGATCGTCGGTTTTGTACAATATGTTGCCGGCATAGTACGCAGCTTCTTC

TAGTTCAATTACACCATTTTTTAGCAGCACCGGATTAACATAACTTTCCAAAATGTTGTACGAA

CCGTTAAACAAAAACAGTTCACCTCCCTTTTCTATACTATTGTCTGCGAGCAGTTGTTTGTTGT

TAAAAATAACAGCCATTGTAATGAGACGCACAAACTAATATCACAAACTGGAAATGTCTATCAA

TATATAGTTGCTCTAGTTATTAATAGTAATCAATTACGGGGTCATTAGTTCATAGCCCATATAT

GGAGTTCCGCGTTACATAACTTACGGTAAATGGCCCGCCTGGCTGACCGCCCAACGACCCCCGC

CCATTGACGTCAATAATGACGTATGTTCCCATAGTAACGCCAATAGGGACTTTCCATTGACGTC

AATGGGTGGACTATTTACGGTAAACTGCCCACTTGGCAGTACATCAAGTGTATCATATGCCAAG

TACGCCCCCTATTGACGTCAATGACGGTAAATGGCCCGCCTGGCATTATGCCCAGTACATGACC

TTATGGGACTTTCCTACTTGGCAGTACATCTACGTATTAGTCATCGCTATTACCATGCATGGTC

GAGGTGAGCCCCACGTTCTGCTTCACTCTCCCCATCTCCCCCCCCTCCCCACCCCCAATTTTGT

ATTTATTTATTTTTTAATTATTTTGTGCAGCGATGGGGGCGGGGGGGGGGGGGCGCGCGCC

AGGCGGGGCGGGGCGGGCGAGGGCGGGGCGGGGCGAGGCGGAGAGGTGCGGCGGCAGCCAAT

CAGAGCGGCGCGCTCCGAAAGTTTCCTTTTATGGCGAGGCGGCGGCGGCGGCGGCCCTATAAAA

AGCGAAGCGCGCGGCGGGCGGGAGTCGCTGCGACGCTGCCTTCGCCCCGTGCCCCGCTCCGCCG

CCGCCTCGCGCCGCCCGCCCCGGCTCTGACTGACCGCGTTACTCCCACAGGTGAGCGGGCGGGA
```

```
CGGCCCTTCTCCTTCGGGCTGTAATTAGCGCTTGGTTTAATGACGGCTTGTTTCTTTTCTGTGG

CTGCGTGAAAGCCTTGAGGGGCTCCGGGAGGGCCCTTTGTGCGGGGGGAGCGGCTCGGGGCTGT

CCGCGGGGGACGGCTGCCTTCGGGGGGACGGGGCAGGGCGGGGTTCGGCTTCTGGCGTGTGA

CCGGCGGCTCTAGAGCCTCTGCTAACCATGTTCATGCCTTCTTCTTTTTCCTACAGCTCCTGGG

CAACGTGCTGGTTATTGTGCTGTCTCATCATTTTGGCAAAGAATTGGATCGGACCGAAATTAAT

ACGACTCACTATA
```

(human Septin-1)

SEQ ID NO: 14

```
MDKEYVGFAALPNQLHRKSVKKGFDFTLMVAGESGLGKSTLINSLFLTNLYEDRQVPEASARLT

QTLAIERRGVEIEEGGVKVKLTLVDTPGFGDSVDCSDCWLPVVKFIEEQFEQYLRDESGLNRKN

IQDSRVHCCLYFISPFGRGLRPLDVAFLRAVHEKVNIIPVIGKADALMPQETQALKQKIRDQLK

EEEIHIYQFPECDSDEDEDFKRQDAEMKESIPFAVVGSCEVVRDGGNRPVRGRRYSWGTVEVEN

PHHCDFLNLRRMLVQTHLQDLKEVTHDLLYEGYRARCLQSLARPGARDRASRSKLSRQSATEIP

LPMLPLADTEKLIREKDEELRRMQEMLEKMQAQMQQSQAQGEQSDAL
```

(human Septin-2)

SEQ ID NO: 15

```
MSKQQPTQFINPETPGYVGFANLPNQVHRKSVKKGFEFTLMVVGESGLGKSTLINSLFLTDLYP

ERVIPGAAEKIERTVQIEASTVEIEERGVKLRLTVVDTPGYGDAINCRDCFKTIISYIDEQFER

YLHDESGLNRRHIIDNRVHCCFYFISPFGHGLKPLDVAFMKAIHNKVNIVPVIAKADTLTLKER

ERLKKRILDEIEEHNIKIYHLPDAESDEDEDFKEQTRLLKASIPFSVVGSNQLIEAKGKKVRGR

LYPWGVVEVENPEHNDFLKLRTMLITHMQDLQEVTQDLHYENFRSERLKRGGRKVENEDMNKDQ

ILLEKEAELRRMQEMIARMQAQMQMQGGDGDGGALGHHV
```

(human Septin-4)

SEQ ID NO: 16

```
MDRSLGWQGNSVPEDRTEAGIKRFLEDTTDDGELSKFVKDFSGNASCHPPEAKTWASRPQVPEP

RPQAPDLYDDDLEFRPPSRPQSSDNQQYFCAPAPLSPSARPRSPWGKLDPYDSSEDDKEYVGFA

TLPNQVHRKSVKKGFDFTLMVAGESGLGKSTLVNSLFLTDLYRDRKLLGAEERIMQTVEITKHA

VDIEEKGVRLRLTIVDTPGFGDAVNNTECWKPVAEYIDQQFEQYFRDESGLNRKNIQDNRVHCC

LYFISPFGHGLRPLDVEFMKALHQRVNIVPILAKADTLTPPEVDHKKRKIREEIEHFGIKIYQF

PDCDSDEDEDFKLQDQALKESIPFAVIGSNTVVEARGRRVRGRLYPWGIVEVENPGHCDFVKLR

TMLVRTHMQDLKDVTRETHYENYRAQCIQSMTRLVVKERNRNKLTRESGTDFPIPAVPPGTDPE

TEKLIREKDEELRRMQEMLHKIQKQMKENY
```

(human Septin-8)

SEQ ID NO: 17

```
MAATDLERFSNAEPEPRSLSLGGHVGFDSLPDQLVSKSVTQGFSFNILCVGETGIGKSTLMNTL

FNTTFETEEASHHEACVRLRPQTYDLQESNVQLKLTIVDAVGFGDQINKDESYRPIVDYIDAQF

ENYLQEELKIRRSLFDYHDTRIHVCLYFITPTGHSLKSLDLVTMKKLDSKVNIIPIIAKADTIS

KSELHKFKIKIMGELVSNGVQIYQFPTDDEAVAEINAVMNAHLPFAVVGSTEEVKVGNKLVRAR

QYPWGVVQVENENHCDFVKLREMLIRVNMEDLREQTHSRHYELYRRCKLEEMGFQDSDGDSQPF

SLQETYEAKRKEFLSELQRKEEEMRQMFVNKVKETELELKEKERELHEKFEHLKRVHQEEKRKV

EEKRRELEEETNAFNRRKAAVEALQSQALHATSQQPLRKDKDKKNRSDIGAHQPGMSLSSSKVM

MTKASVEPLNCSSWWPAIQCCSCLVRDATWREGFL
```

(human Septin-9)

SEQ ID NO: 18

```
MKKSYSGGTRTSSGRLRRLGDSSGPALKRSFEVEEVETPNSTPPRRVQTPLLRATVASSTQKFQ

DLGVKNSEPSARHVDSLSQRSPKASLRRVELSGPKAAEPVSRRTELSIDISSKQVENAGAIGPS
```

-continued

```
RFGLKRAEVLGHKTPEPAPRRTEITIVKPQESAHRRMEPPASKVPEVPTAPATDAAPKRVEIQM

PKPAEAPTAPSPAQTLENSEPAPVSQLQSRLEPKPQPPVAEATPRSQEATEAAPSCVGDMADTP

RDAGLKQAPASRNEKAPVDFGYVGIDSILEQMRRKAMKQGFEFNIMVVGQSGLGKSTLINTLFK

SKISRKSVQPTSEERIPKTIEIKSITHDIEEKGVRMKLTVIDTPGFGDHINNENCWQPIMKFIN

DQYEKYLQEEVNINRKKRIPDTRVHCCLYFIPATGHSLRPLDIEFMKRLSKVVNIVPVIAKADT

LTLEERVHFKQRITADLLSNGIDVYPQKEFDEDSEDRLVNEKFREMIPFAVVGSDHEYQVNGKR

ILGRKTKWGTIEVENTTHCEFAYLRDLLIRTHMQNIKDITSSIHFEAYRVKRLNEGSSAMANGM

EEKEPEAPEM
```

(human Septin-10)
SEQ ID NO: 19
```
MASSEVARHLLFQSHMATKTTCMSSQGSDDEQIKRENIRSLTMSGHVGFESLPDQLVNRSIQQG

FCFNILCVGETGIGKSTLIDTLFNTNFEDYESSHFCPNVKLKAQTYELQESNVQLKLTIVNTVG

FGDQINKEESYQPIVDYIDAQFEAYLQEELKIKRSLFTYHDSRIHVCLYFISPTGHSLKTLDLL

TMKNLDSKVNIIPVIAKADTVSKTELQKFKIKLMSELVSNGVQIYQFPTDDDTIAKVNAAMNGQ

LPFAVVGSMDSVKVGNKMVKARQYPWGVVQVENENHCDFVKLREMLICTNMEDLREQTHTRHYE

LYRRCKLEEMGFTDVGPENKPVSVQETYEAKRHEFHGERQRKEEEMKQMFVQRVKEKEAILKEA

ERELQAKFEHLKRLHQEERMKLEEKRRLLEEEIIAFSKKKATSEIFHSQSFLATGSNLRKDKDR

KNSNFL
```

(human Septin-12)
SEQ ID NO: 20
```
MDPLRRSPSPCLSSQPSSPSTPPCEMLGPVGIEAVLDQLKIKAMKMGFEFNIMVVGQSGLGKST

MVNTLFKSKVWKSNPPGLGVPTPQTLQLHSLTHVIEEKGVKLKLTVTDTPGFGDQINNDNCWDP

ILGYINEQYEQYLQEEILITRQRHIPDTRVHCCVYFVPPTGHCLRPLDIEFLQRLCRTVNVVPV

IARADSLTMEEREAFRRRIQQNLRTHCIDVYPQMCFDEDINDKILNSKLRDRIPFAVVGADQEH

LVNGRCVLGRKTKWGIIEVENMAHCEFPLLRDLLIRSHLQDLKDITHNIHYENYRVIRLNESHL

LPRGPGWVNLAPASPGQLTTPRTFKVCRGAHDDSDDEF
```

(human Septin-14)
SEQ ID NO: 21
```
MAERTMAMPTQIPADGDTQKENNIRCLTTIGHFGFECLPNQLVSRSIRQGFTFNILCVGETGIG

KSTLIDTLFNTNLKDNKSSHFYSNVGLQIQTYELQESNVQLKLTVVETVGYGDQIDKEASYQPI

VDYIDAQFEAYLQEELKIKRSLFEYHDSRVHVCLYFISPTGHSLKSLDLLTMKNLDSKVNIIPL

IAKADTISKNDLQTFKNKIMSELISNGIQIYQLPTDEETAAQANSSVSGLLPFAVVGSTDEVKV

GKRMVRGRHYPWGVLQVENENHCDFVKLRDMLLCTNMENLKEKTHTQHYECYRYQKLQKMGFTD

VGPNNQPVSFQEIFEAKRQEFYDQCQREEEELKQRFMQRVKEKEATFKEAEKELQDKFEHLKMI

QQEEIRKLEEEKKQLEGEIIDFYKMKAASEALQTQLSTDTKKDKHRKK
```

(human Septin-7, aa 1-51)
SEQ ID NO: 22
```
MSVSARSAAAEERSVNSSTMVAQQKNLEGYVGFANLPNQVYRKSVKRGFEF
```

(human Septin-7, aa 334-437)
SEQ ID NO: 23
```
SPLAQMEEERREHVAKMKKMEMEMEQVFEMKVKEKVQKLKDSEAELQRRHEQMKKNLEAQHKEL
EEKRRQFEDEKANWEAQQRILEQQNSSRTLEKNKKKGKIF
```

EXAMPLES

The present invention is further illustrated by the following non-limiting examples from which further features, embodiments, aspects and advantages of the present invention may be taken.

SUMMARY

Methods: Six patients (P1-P6) suffering from neurological conditions underwent serological investigation. For this purpose, all patient sera were subjected to autoantibody screening by indirect immunofluorescence assay (IFA) with hippocampal tissue sections and recombinant HEK cells expressing either a complex of Septin-3 (SEQ ID NO: 9), Septin-5 (SEQ ID NO: 10), Septin-6 (SEQ ID NO: 11), Septin-7 (SEQ ID NO8), and Septin-11 (SEQ ID NO: 11), or each Septin protein separately. All Septin proteins used were fused to a His tag. Furthermore, Septin complex variants missing one of the five Septin proteins were used in IFA. Additionally, HEK cells expressing the Septin complex or single Septin proteins were incubated with healthy control sera.

Results: IFA screening of sera from P1 to P4 revealed IgG reactivity with the outer molecular layer of rat hippocampus. With all sera IgG reactivity against Septin-7 and a complex of Septin-3, Septin-5, Septin-6, Septin-7, and Septin-11 was detected. Screening of healthy control sera without a specific reaction in IFA with neuronal tissues (n=50) revealed no anti-Septin 7 positive sample. Furthermore, all patient sera showed no reactivity against the Septin 3+5+6+11 complex lacking Septin-7, indicating that patients' sera bind specifically to Septin-7.

Clinical data from all of the patients with anti-Septin-7 autoantibodies was available. P1, P2, P4, and P5 suffered from peripheral neuropathy, P3 suffered on encephalopathy, and P6 was diagnosed with bilateral carpal tunnel syndrome and lumbosacral polyradiculopathies. In two of the six patients a tumour was detected (P4 ovarian cancer, P5 carcinoid of the lung).

Patients

Control collectives included 50 healthy donors.

Indirect Immunofluorescence Assay (IFA)

IFA was conducted using slides with a biochip array of hippocampal cryosections combined with recombinant HEK293 cells separately expressing different Septin complexes (3+5+6+7+11; 5+6+7+11; 3+6+7+11; 3+5+7+11; 3+5+6+11; 3+5+6+7) or each Septin protein separately.

Each biochip mosaic was incubated with 35 µL of 1:100 PBS-diluted sample at room temperature for 30 min, washed with PBS-Tween and immersed in PBS-Tween for 5 min. In the second step, fluorescein isothiocyanate (FITC)-labelled goat anti-human IgG (EUROIMMUN Medizinische Labordiagnostika AG, Lübeck) was applied and incubated at room temperature for 30 min. Slides were washed again with a flush of PBS-Tween (EUROIMMUN Medizinische Labordiagnostika AG, Lübeck) and then immersed in PBS-Tween for 5 min. Slides were embedded in PBS-buffered, DABCO containing glycerol ((EUROIMMUN Medizinische Labordiagnostika AG, Lübeck), approximately 10 µL per field) and examined by fluorescence microscopy. Positive and negative controls were included. Samples were classified as positive or negative based on fluorescence intensity of the transfected cells in direct comparison with non-transfected cells and control samples. Endpoint titers refer to the last dilution showing visible fluorescence. Further details and reagents are listed in the manual related to product FA_112d-1_A_UK_C13 by EUROIMMUN Medizinische Labordiagnostika AG.

Results were evaluated by two independent observers using a EUROStar II microscope (EUROIMMUN Medizinische Labordiagnostika AG, Lübeck, Germany). Reagents were obtained from Merck, Darmstadt, Germany or Sigma-Aldrich, Heidelberg, Germany if not specified otherwise.

Recombinant Expression of Septin Proteins in HEK293 Cells:

His-tagged Septin proteins were cloned into mammalian expression vector pTriEx-1 (Merck, Darmstadt, Germany) and the corresponding Septin proteins, as shown in SEQ ID NO: 8 (human Septin-7), SEQ ID NO: 9 (human Septin-3), SEQ ID NO: 10 (human Septin-5), SEQ ID NO: 11 (human Septin-6) and SEQ ID NO12 (human SEptin-11) were or Septin-7 alone (SEQ ID NO: 13) was transiently expressed in the human cell line HEK293 following PEI-mediated transfection (Exgene 500), according to the manufacturer's instructions (Biomol GmbH, Hamburg, Germany).

For the production of Immunofluorescence substrates, the cells were grown on cover slides in DMEM (Invitrogen, Karlsruhe, Germany) with 10% foetal calf serum in a $CO_2$ incubator at 37° C., 5% $CO_2$ and 95% humidity and acetone fixed two days after transfection.

Characterization of the Patients' Autoantibodies

Indirect immunofluorescence assays (IFA) of sera P1 to P4 using permeabilized cryosections of rat hippocampus showed granular staining of the molecular layer (FIG. 1). The outer molecular layer of the dentate gyrus ("sm" in FIG. 1) revealed a stronger reactivity compared to the inner molecular layer.

Identification of Septin as the Target Neuronal Autoantigen

Figure 2:
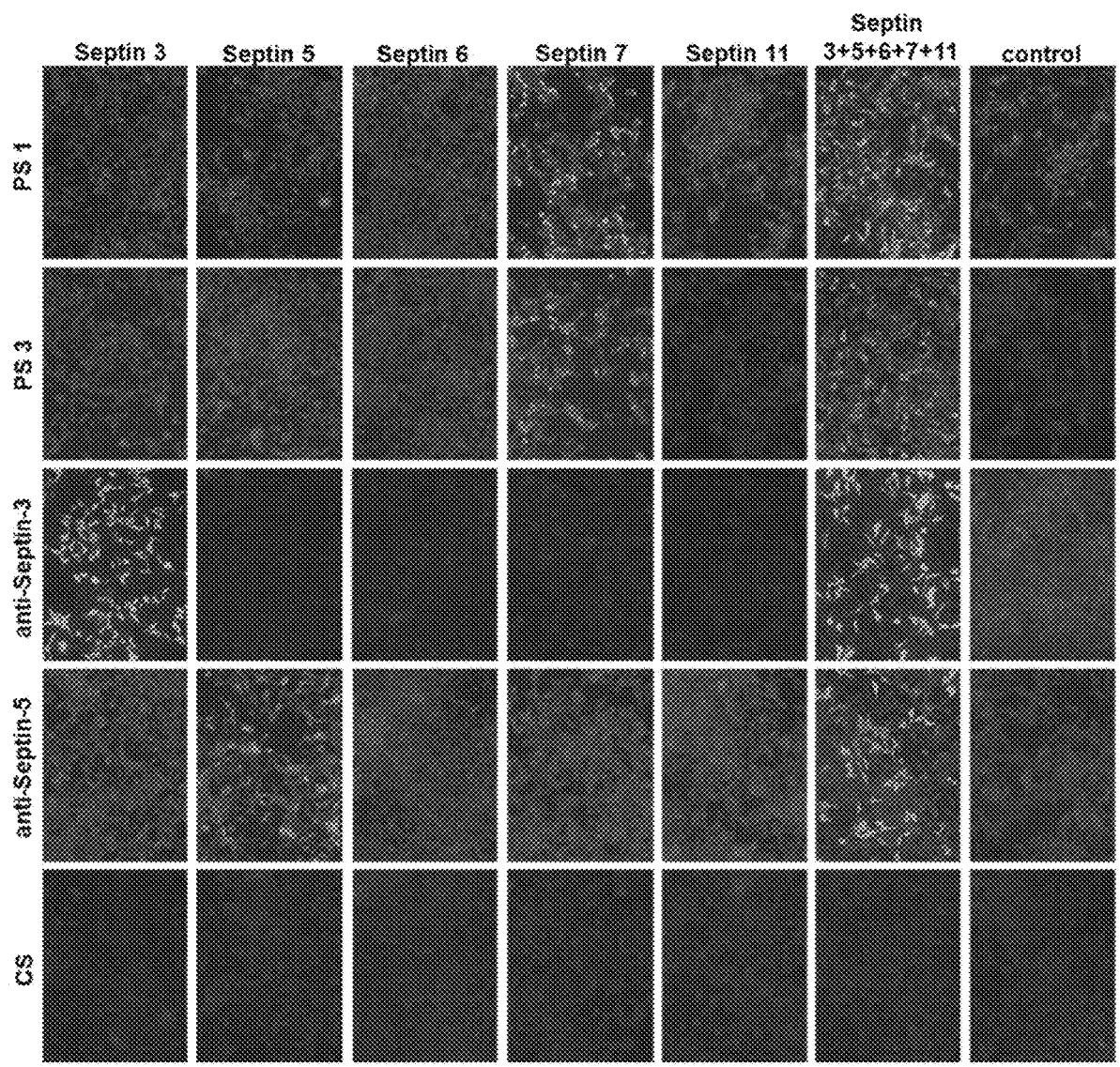
FIG. 2 shows the results of indirect immunofluorescence assays with two representative anti-Septin-7 positive patient sera (PS1 and PS3), a healthy control serum (CS), or sera comprising an autoantibody to Septin-3 or an autoantibody to Septin-5 as control (all 1:100) on HEK293 cells expressing a single Septin protein, a Septin-3+5+6+7+11 complex or mock-transfected control cells. Both patient sera (PS1, PS3) show a specific reaction with Septin-7 and Septin 3+5+6+7+11 complex expressing cells. With both patient sera, no reaction is observed with HEK cells expressing the single Septin-3, -5, -6 or -11 proteins or with mock-transfected control cells. The sera comprising an autoantibody to Septin-3 or Septin-5 only react with Septin-3 or Septin-5 expressing cells, respectively, and with cells expressing the Septin 3+5+6+7+11 complex. The healthy control serum shows no reactivity on all substrates.

The patients' samples were tested by IFA using transfected HEK293 cells overexpressing Septin-7 or co-overexpressing Septin-3, Septin-5, Septin-6, Septin-7 and Septin-11. Patients' sera (P1 to P6) reacted with cells expressing Septin-7 individually as well as with cells coexpressing Septin-3, Septin-5, Septin-6, Septin-7 and Septin-11 (FIG. 2). In contrast, mock-transfected cells did not demonstrate any specific antibody binding (FIG. 2). Patients' sera showed no positive signal if Septin-3, Septin-5, Septin-6, or Septin-11 was expressed individually. In contrast sera comprising an autoantibody to Septin-3 or Septin-5 did only react with the complex comprising Septin-3, Septin-5, Septin-6, Septin-7 and Septin-11, but no reactivity against Septin-7 expressing cells was observed.

Figure 3:
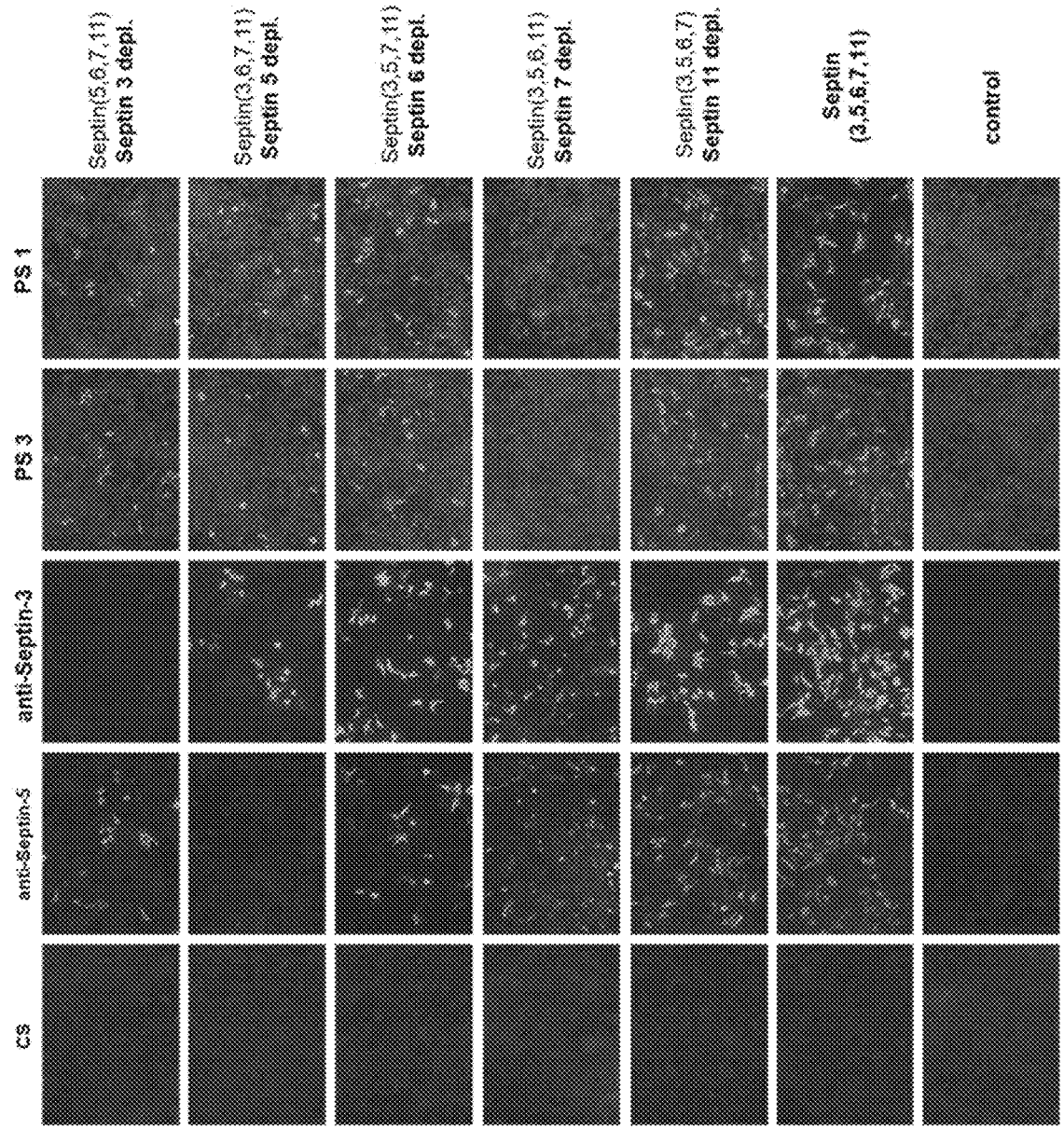
FIG. 3 shows the results of indirect immunofluorescence assays with two representative positive patient sera comprising an autoantibody to Septin-7 (PS1 and PS3), a healthy control serum (CS), or sera comprising an autoantibody to Septin-3 or an autoantibody to Septin-5 as controls (all 1:100) on HEK293 cells expressing the Septin 3+5+6+7+11 complex or different Septin depletion complexes lacking one of the five Septin proteins. Both patient sera do not react with the complex lacking Septin-7, but with all other complexes. In contrast, the sera comprising an autoantibody to Septin-3 or Septin-5 do not show a positive reaction with the complex lacking Septin-3 or Septin-5, respectively. The healthy control serum shows no reactivity on all substrates.

Further combinations of overexpressed Septin proteins (Septin 5+6+7+11; Septin 3+6+7+11; Septin 3+5+7+11; Septin 3+5+6+11; Septin 3+5+6+7) were analyzed by RC-IFA with the patients' sera (FIG. 3). All patient sera showed no reaction with cells expressing the Septin 3+5+6+11 complex lacking Septin-7, whereas the sera comprising an autoantibody to Septin-3 or to Septin-5 reacted with this complex (FIG. 3). These results indicate that the reactivity of the patients' sera depends on Septin-7.

Specificity of Anti-Septin-7 Auto-Antibodies

Up to 50 healthy control sera were analyzed by IFA with HEK293 cells overexpressing Septin-7 or HEK293 cells overexpressing the complex comprising Septin-3, Septin-5, Septin-6, Septin-7 and Septin-11 or other combinations in parallel to the samples of the patients. None of the control sera showed a positive reaction with HEK293 cells overexpressing Septin-7 or HEK293 cells overexpressing the complex comprising Septin-3, Septin-5, Septin-6, Septin-7 and Septin-11 in a 1:100 dilution.

Characterization of Septin-7 Epitope Recognized by Patient's Autoantibodies

For epitope mapping HEK239 cells expressing full-length Septin-7-His lysed as described above or E. coli expressing His-GST-Septin-7 fragments (aa 1-51, 40-203, 192-345, 334-437) in a pET24d vector (Merck, Germany) were incubated with NuPage LDS sample buffer (ThermoFisher Scientific, Germany) containing 25 mmol/L dithiothreitol at 70° C. for 10 min. Lysates were immunoblotted as described above. Briefly, membranes were incubated with anti-His mouse monoclonal antibody (Merck, Germany, 1:2000), patient or control sera (1:200) in Universal Blot Buffer plus (Euroimmun) for 3 hours, and for 30 min with anti-mouse- IgG-AP (Jackson ImmunoResearch, UK, 1:2000) or anti-human-IgG-AP (1:10) in Universal Blot Buffer plus.

Figure 4:
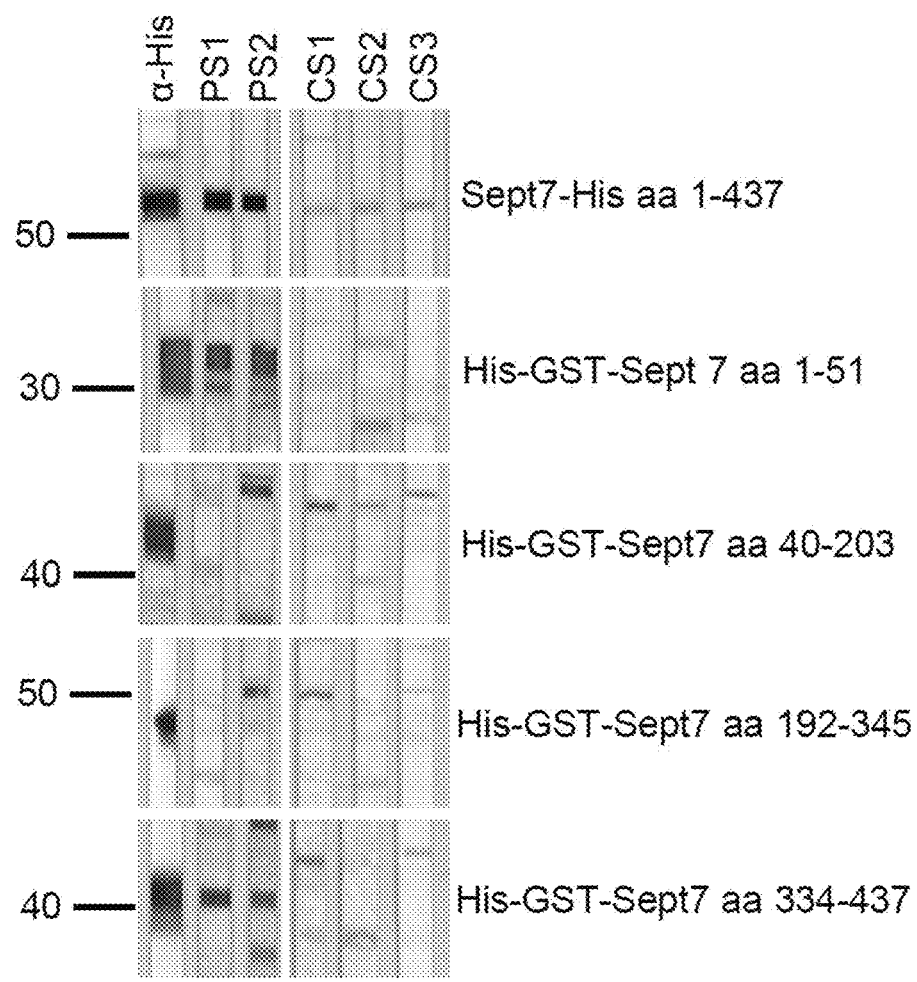
FIG. 4 shows a HEK293 lysate containing recombinant full length Septin-7 or *E. coli* lysates containing different recombinant Septin-7 fragments (aa 1-51, 40-203, 192-345, 334-437) which were analyzed by Western Blot incubated with anti-his-tag antibody, patient's sera (P1, P2), and control sera (CS1-CS3). The positions of the respective recombinant antigens are shown by positive anti-his-tag reactions. PS1 and PS2 show positive reactions with full length Septin-7, the N-terminal fragment (aa 1-51) and the C-terminal fragment (aa-334-437) while control sera did not show positive reactions with any fragment or the full-length protein. Molecular weights [kDa] are indicated.

The Septin-7 full-length protein, the N-terminal Septin-7 fragment (aa 1-51), and the C-terminal Septin-7 fragment (aa 334-437) were recognized by the patient's sera (P1 and P2 exemplary) but not by control sera (CS1, CS2, and CS3 exemplary) (FIG. 4), indicating that patient's autoantibodies recognize epitopes located in the first 51 aa and the last 103 aa of Septin-7. The presence of all fragments was confirmed by a positive anti-His tag reaction.

Studying a Second Cohort of Patients Having Septin-5 and/or Septin-7 Autoantibodies A second cohort of patients was used to distinguish Septin-7 specific autoantibodies from other Septin autoantibodies, especially from patients having Septin-5 autoantibodies. Nine of 17 patients were men. Median symptom onset age was 62 years (range, 40-85) (FIGS. 5A, 5B, and 5C).

Figure 6:
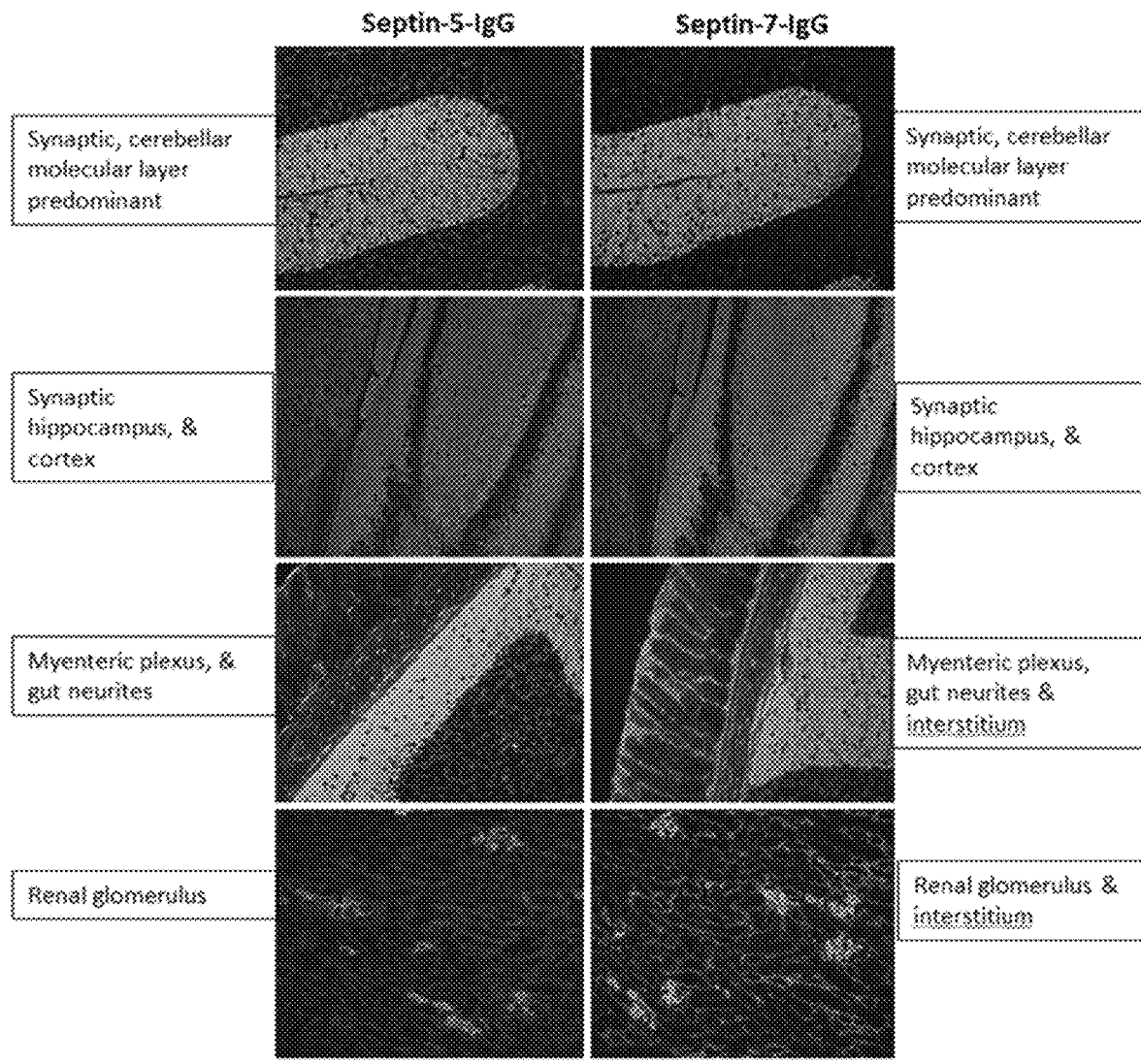
FIG. 6 shows the differential patterns of IgG staining of murine brain synapses, gut and kidney produced by CSF from Septin-5- and Septin-7-IgG positive patients.

Five of 17 patients, characterized as having Septin-5 autoimmunity, were previously described. Specimens from all 17 strongly stained synaptic regions (neuropil) of the mouse cerebrum and cerebellum (FIG. 6). The molecular layer of the cerebellum and the thalamus demonstrated stronger immunoreactivity than the midbrain, hippocampus, cortex, and basal ganglia. The myenteric plexus of the gastric mucosa and the renal glomeruli were also reactive in all cases. In addition, in the 12 new cases having Septin-7 autoimmunity, additional interstitial staining was identified in gastric mucosa and kidney. Thus, indicating that Septin-7 autoantibodies can be distinguished from Septin-5 autoantibodies by their binding pattern of gastric mucosa and kidney tissue.

Figure 7:
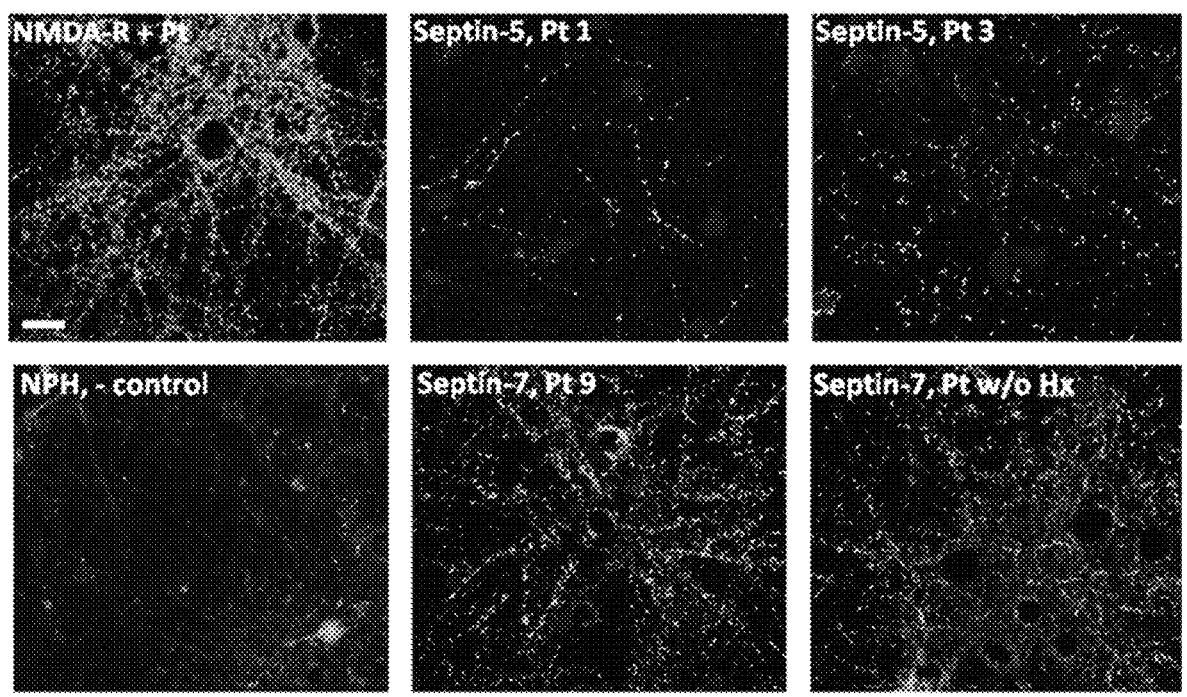
FIG. 7 shows a live hippocampal neuron assay of CSF. Diffuse membranous IgG staining of neurons produced by NMDA-R-IgG positive control, and no staining produced by CSF of a normal pressure hydrocephalus patient. In contrast, CSF from two Septin-7-IgG positive patients produces limited membranous staining, and CSF from two Septin-5-IgG positive patients produces even more limited punctal staining.

Septin-5- and -7 blots and CBAs yielded IgGs reactive with Septin-7 (11 patients), Septin-5 (4), or both (2). Supportive of IgG pathogenicity, all 4 CSF specimens tested were reactive with extracellular-facing plasma membrane surfaces of live hippocampal neurons. Staining was punctate, though was more restricted for Septin-5-IgG cases (FIG. 7) indicating that Septin-7 and Septin-5 autoantibodies can also be distinguished from each other by their IgG staining of neurons.

The invention claimed is:

1. A method, comprising:
   detecting, in a sample from a patient, an autoantibody binding to Septin-7, and an absence of the autoantibody binding to one or more of Septin-3, Septin-5, Septin-6, or Septin-11,
   wherein the patient has or is suspected of having a disease, wherein the disease is selected from the group consisting of paraneoplastic neurological syndrome (PNS), neuropathy, encephalopathy, encephalitis, encephalomyelopathy, myelopathy, episodic ataxia, bilateral carpal tunnel syndrome, and lumbosacral polyradiculopathy, or
   wherein the disease is a tumor selected from the group consisting of ovarian cancer, breast adenocarcinoma, Non-Hodgkin lymphoma, carcinoid, myelodysplastic syndrome, and carcinoid of the lung.

2. The method of claim 1, wherein the detecting is performed with a polypeptide comprising Septin-7.

3. The method according to claim 2, wherein the Septin-7 polypeptide is immobilized to a carrier.

4. The method according to claim 1, wherein the sample is selected from the group consisting of a bodily fluid comprising antibodies, whole blood, plasma, serum, cerebrospinal fluid, and saliva.

5. The method according of claim 1, wherein Septin-7 is part of a Septin complex comprising Septin-7 and at least one Septin selected from the group consisting of Septin-3, Septin-5, Septin-6, and Septin-11.

6. The method according to claim 1, wherein the Septin-7 is a polypeptide having a sequence having at least 95% identity to SEQ ID NO: 1, SEQ ID NO: 2, SEQ ID NO: 3, SEQ ID NO: 8, SEQ ID NO: 22, and/or SEQ ID NO: 23.

7. A method, comprising:
   contacting a sample from a patient, the sample comprising an autoantibody to Septin-7, with a polypeptide comprising Septin-7 and (1) a polypeptide or polypeptides to one or more of Septin-3, Septin-5, Septin-6, Septin-11, and/or (2) a complex containing the Septin-7 and one or more of Septin-3, Septin-5, Septin-6, Septin-11,
   wherein the patient has or is suspected of having a disease, wherein the disease is selected from the group consisting of paraneoplastic neurological syndrome (PNS), neuropathy, encephalopathy, encephalitis, encephalomyelopathy, myelopathy, episodic ataxia, bilateral carpal tunnel syndrome, and lumbosacral polyradiculopathy, or
   wherein the disease is a tumor selected from the group consisting of ovarian cancer, breast adenocarcinoma, Non-Hodgkin lymphoma, carcinoid, myelodysplastic syndrome, and carcinoid of the lung.

8. The method according to claim 7, wherein the polypeptide comprising Septin-7 is immobilized to a carrier.

9. The method according to claim 8, wherein the carrier is selected from the group consisting of paper, polystyrene, metal, silicon surface, glass surface, microfluidic channel, membrane, bead, column chromatography medium, biochip, polyacrylamide gel.

10. The method according to claim 7, wherein the Septin-7 is a polypeptide having a sequence having at least 95% identity to SEQ ID NO: 1, SEQ ID NO: 2, SEQ ID NO: 3, SEQ ID NO: 8, SEQ ID NO: 22, and/or SEQ ID NO: 23.

11. A method for isolating an autoantibody binding to Septin-7, comprising:
   contacting a sample comprising the autoantibody with a polypeptide comprising Septin-7 under conditions compatible with formation of a complex, wherein said autoantibody binds to said polypeptide, wherein the complex contains Septin-7 and at least one of Septin-3, Septin-5, Septin-6, Septin-7, Septin-11,
   isolating the complex, and
   detecting the complex, dissociating the complex and separating the autoantibody from the polypeptide.

12. The method according to claim 11, wherein the autoantibody or complex is detected using a technique selected from the group consisting of an immunodiffusion technique, an immunoelectrophoretic technique, a light scattering immunoassay, an agglutination technique, a labeled immunoassay, a radiolabeled immunoassay, an enzyme immunoassay, ELISA, a chemiluminescence immunoassay, an electrochemiluminescence immunoassay, immunofluorescence, and indirect immunofluorescence.

13. The method according to claim 11, wherein the Septin-7 is a polypeptide having a sequence having at least 95% identity to SEQ ID NO: 1, SEQ ID NO: 2, SEQ ID NO: 3, SEQ ID NO: 8, SEQ ID NO: 22, and/or SEQ ID NO: 23.

* * * * *

UNITED STATES PATENT AND TRADEMARK OFFICE
CERTIFICATE OF CORRECTION

PATENT NO. : 11,835,519 B2
APPLICATION NO. : 17/114984
DATED : December 5, 2023
INVENTOR(S) : Miske et al.

It is certified that error appears in the above-identified patent and that said Letters Patent is hereby corrected as shown below:

In the Specification

In Column 24, Line 6 of SEQ ID NO. 1 currently reads "RSHV" and should read "REHV";

In Column 24, Line 6 of SEQ ID NO. 2 currently reads "MSME" and should read "MEME";

In Column 24, Line 2 of SEQ ID NO. 3 currently reads "DMSN" and should read "DNSN";

In Column 24, Line 5 of SEQ ID NO. 3 currently reads "NTR" and should read "NYR";

In Column 24, Line 7 of SEQ ID NO. 3 currently reads "KNNL" and should read "KKNL";

In Column 24, Line 1 of SEQ ID NO. 4 currently reads "TRIDA" and should read "TRTDA";

In Column 24, Line 1 of SEQ ID NO. 4 currently reads "PFPR" and should read "PEPR".

In Column 25, Line 7 of SEQ ID NO. 6 currently reads "WLTE" and should read "WLCTE".

In Column 27, Line 2 of SEQ ID NO. 11 currently reads "GFPATH" and should read "GEPATH";

In Column 27, Line 7 of SEQ ID NO. 11 currently reads "TELEHHKH" and should read "TELEHHHH".

In Column 35, Line 5 of SEQ ID NO. 19 currently reads "VVGSMDS" and should read "VVGSMDE".

Signed and Sealed this
Fourth Day of June, 2024

Katherine Kelly Vidal
*Director of the United States Patent and Trademark Office*